United States Patent
Feinstein et al.

(10) Patent No.: US 9,611,474 B2
(45) Date of Patent: Apr. 4, 2017

(54) DOUBLE-STRANDED OLIGONUCLEOTIDE MOLECULES TO DDIT4 AND METHODS OF USE THEREOF

(71) Applicant: Quark Pharmaceuticals, Inc., Fremont, CA (US)

(72) Inventors: Elena Feinstein, Rehovot (IL); Sharon Avkin-Nachum, Nes Zionna (IL); Hagar Kalinski, Rishon-le-Zion (IL); Igor Mett, Rehovot (IL)

(73) Assignee: QUARK PHARMACEUTICALS, INC., Fremont, CA (US)

( * ) Notice: Subject to any disclaimer, the term of this patent is extended or adjusted under 35 U.S.C. 154(b) by 0 days.

(21) Appl. No.: 14/426,513

(22) PCT Filed: Sep. 12, 2013

(86) PCT No.: PCT/US2013/059341
§ 371 (c)(1),
(2) Date: Mar. 6, 2015

(87) PCT Pub. No.: WO2014/043289
PCT Pub. Date: Mar. 20, 2014

(65) Prior Publication Data
US 2015/0267194 A1    Sep. 24, 2015

Related U.S. Application Data

(60) Provisional application No. 61/699,884, filed on Sep. 12, 2012.

(51) Int. Cl.
*C07H 21/04* (2006.01)
*C12N 15/113* (2010.01)

(52) U.S. Cl.
CPC ........ *C12N 15/113* (2013.01); *C12N 15/1135* (2013.01); *C12N 15/1136* (2013.01); *C12N 2310/14* (2013.01); *C12N 2310/317* (2013.01); *C12N 2310/319* (2013.01); *C12N 2310/321* (2013.01); *C12N 2310/3521* (2013.01); *C12N 2320/30* (2013.01)

(58) Field of Classification Search
CPC ...................................................... C07H 21/04
See application file for complete search history.

(56) References Cited

U.S. PATENT DOCUMENTS 9,056,903 B2    6/2015 Feinstein et al.

FOREIGN PATENT DOCUMENTS

| WO | 2004/015107 A2 | 2/2004 |
|---|---|---|
| WO | 2007/084684 A2 | 7/2007 |
| WO | 2010/048352 A2 | 4/2010 |
| WO | 2011/066475 A1 | 6/2011 |
| WO | 2013/070821 A1 | 5/2013 |

OTHER PUBLICATIONS

International Search Report and Written Opinion for Application No. PCT/US2013/059341, mailed Apr. 24, 2014 (23 pages).
Weitzer et al., "The human RNA kinase hClp1 is active on 3' transfer RNA exons and short interfering RNAs". Nature, vol. 447, No. 7141, May 10, 2007: pp. 222-226.
Weitzer et al., "A kinase hClp1 is active on 3' transfer RNA exons and short interfering RNAs—Supplementary Information". Nature, vol. 447, No. 7141, May 10, 2007 (21 pages).
Nykanen et al., "ATP requirements and Small Interfering RNA Structure in the RNA Interference Pathway". Cell, vol. 107, No. 3, Nov. 2, 2001: pp. 309-321.
Pellino et al., "ATP modulates siRNA interactions with an endogenous human Dicer complex". RNA, vol. 11, No. 11, 2005: pp. 1719-1724.
International Preliminary Report on Patentability for Application No. PCT/US2013/059341, mailed Mar. 26, 2015 (14 pages).

*Primary Examiner* — Kimberly Chong
(74) *Attorney, Agent, or Firm* — Nutter McClennen & Fish LLP; Isaac A. Hubner; Konstantin Linnik

(57) ABSTRACT

Provided herein are double stranded nucleic acid molecules, compositions comprising same and methods of use thereof for the treatment of a subject wherein expression of DDIT4 is associated with the etiology or progression of a disease or disorder in the subject. The compounds are preferably chemically synthesized and modified dsRNA molecules.

20 Claims, 14 Drawing Sheets

DOUBLE-STRANDED OLIGONUCLEOTIDE MOLECULES TO DDIT4 AND METHODS OF USE THEREOF

SEQUENCE LISTING

This application incorporates-by-reference nucleotide and/or amino acid sequences which are present in the file named "232_PCT1_ST25.txt", which is 13 kilobytes in size, and which was created Sep. 12, 2013 in the IBM-PCT machine format, having an operating system compatibility with MS-Windows.

FIELD OF THE INVENTION

Provided herein are nucleic acid molecules, pharmaceutical compositions comprising same and methods of use thereof for the down-regulation of DDIT4 expression, the inhibition of which is useful for treating a patient suffering from or at risk for the development of a disease or a disorder associated with DDIT4 gene expression.

BACKGROUND OF THE INVENTION

DDIT4

The DDIT4 (RTP801, REDD1) gene was first reported by the assignee of the instant application. U.S. Pat. Nos. 6,455,674, 6,555,667, and 6,740,738, and related patents to the assignee of the instant application and hereby incorporated by reference in their entirety, disclose the RTP801 polynucleotide and polypeptide, and antibodies directed toward the polypeptide. RTP801 represents a unique gene target for hypoxia-inducible factor-1 (HIF-1) that may regulate hypoxia-induced pathogenesis independently of growth factors such as VEGF. Double stranded RNA molecules, which down regulate DDIT4 are disclosed in, inter alia, U.S. Pat. Nos. 7,741,299; 8,067,570; 7,872,119 and US Patent Publication No. 2011/0028531, to the Assignee of the present application and hereby incorporated by reference in their entirety. Additional molecules are disclosed in U.S. Pat. No. 7,655,788 and US Patent Publication No 2010/0285038.

US Application Publication Nos 2010/0292301 and 2011/0112168, and PCT Patent Publication Nos. WO 2011/066475, WO 2011/084193, WO 2011/085056 and WO 2012/078536 to the assignee of the present application and hereby incorporated by reference in their entirety, disclose nucleic acid sequences and modifications useful in generating dsRNA molecules.

US Application Publication Nos. 2011/0142917, 2011/0229557 and 2012/0141378 to the assignee of the present application and hereby incorporated by reference in their entirety, disclose compositions and methods of use comprising DDIT4 dsRNA.

A patent application disclosing phenyl hydrocarbyl moieties useful for covalently attaching to dsRNA, to the assignee of the present application, is filed concomitantly with the present application.

Molecules, compositions, methods and kits useful for the down regulation of DDIT4 and which exhibit at least one of increased bioavailability, improved biodistribution, increased serum circulation time, increased serum stability, decreased serum clearance, improved cellular uptake, reduced off target activity, reduced immunogenicity, improved endosomal release, improved specific delivery to target tissue or cell and increased knock down activity when compared to unmodified dsRNA counterparts are needed.

SUMMARY OF THE INVENTION

Nucleic acid molecules useful for down-regulating expression of DDIT4, compositions and kits comprising same and methods of use thereof are provided herein. The compositions, methods and kits may involve use of nucleic acid molecules (for example, short interfering nucleic acid (siNA), short interfering RNA (siRNA), double-stranded RNA (dsRNA), micro-RNA (miRNA), ssRNA (single stranded RNA), dicer substrate dsRNA, asymmetric siRNA, or short hairpin RNA (shRNA, synthetic or recombinantly expressed)) that bind a nucleotide sequence (such as an mRNA sequence) or portion thereof, encoding DDIT4, for example, the mRNA coding sequence (SEQ ID NO:1) for human DDIT4, encoding the polypeptide exemplified by SEQ ID NO:2. In certain preferred embodiments, the molecules, compositions, methods and kits disclosed herein down-regulate or inhibit expression of the DDIT4 gene. In various embodiments the nucleic acid molecule is an unmodified or chemically modified dsRNA compound such as a siRNA or shRNA that down-regulates DDIT4 expression.

The chemically modified nucleic acid molecules and compositions provided herein exhibit beneficial properties, including at least one of increased serum stability, improved cellular uptake, reduced off-target activity, reduced immunogenicity, improved endosomal release, improved specific delivery to target tissue or cell and increased knock down/down-regulation activity when compared to corresponding unmodified nucleic acid molecules.

Further disclosed herein are methods for treating or preventing the incidence or severity of a disorder, disease, injury or condition in a subject in need thereof wherein the disease or condition and/or a symptom or pathology associated therewith is associated with expression of the DDIT4 gene, such as a disorder, disease, injury, condition or pathology selected from respiratory disorders, eye diseases and conditions, hearing impairments (including hearing loss), neurodegenerative disorders, spinal cord injury, microvascular disorders, skin atrophy diseases and disorders, angiogenesis- and apoptosis-related conditions. In some embodiments the subject is a mammal. In a preferred embodiment the subject is a human subject.

Other conditions in which DDIT4 expression plays a role in disease etiology or disease progression, are encompassed by the methods and uses disclosed herein.

In one aspect, provided are nucleic acid molecules (e.g., dsRNA molecules) capable of targeting DDIT4 mRNA (SEQ ID NO:1); wherein (a) the nucleic acid molecule is a duplex which includes a sense strand and a complementary antisense strand; (b) each strand of the nucleic acid molecule is independently 18 to 49 nucleotides in length; (c) an 18 to 49 nucleotide sequence of the antisense strand is complementary to an 18 to 49 consecutive nucleotide sequence in the DDIT4 mRNA; and (d) the sense strand and antisense strand comprise oligonucleotide pairs set forth in any of SEQ ID NOS:3 and 12; SEQ ID NOS:4 and 13; SEQ ID NOS:5 and 14; SEQ ID NOS:6 and 15; SEQ ID NOS:7 and 16; SEQ ID NOS:8 and 17; SEQ ID NOS:9 and 18; SEQ ID NOS:10 and 19; or SEQ ID NOS:11 and 20; or a pharmaceutically acceptable salt of such molecule.

In some embodiments the nucleic acid molecule comprises unmodified ribonucleotides and/or modified ribonucleotides and/or unconventional moieties. In some embodiments, the nucleic acid molecule further comprises a vitamin, drug moiety, a capping moiety and/or 3' terminal overhangs.

In some embodiments, the nucleic acid molecule comprises a mismatch to the DDIT4 target mRNA at position 1 of the antisense strand (5' terminus). In other embodiments, the nucleic acid molecules comprise a DNA moiety in position 1 of the antisense strand. Such duplex structures are described herein as structure (A2), set forth below:

5' N1-(N)x-Z 3' (antisense strand)

3' Z'-N2-(N')y-z" 5' (sense strand) (A2)

wherein each N1, N2, N and N' is independently an unmodified or modified nucleotide, or an unconventional moiety;
wherein each of (N)x and (N')y is an oligonucleotide in which each consecutive N or N' is joined to the adjacent N or N' by a covalent bond;
wherein each of x and y is independently an integer between 17 and 39;
wherein N2 is covalently bound to (N')y;
wherein N1 is covalently bound to (N)x and is mismatched to DDIT4 mRNA or is a DNA nucleotide complementary to the DDIT4 mRNA and is
selected from the group consisting of natural or modified: uridine, deoxyribouridine, ribothymidine, deoxyribothymidine, adenosine or deoxyadenosine;
wherein z" may be present or absent, but if present is a capping moiety or a conjugate moiety covalently attached at the 5' terminus of N2-(N')y;
wherein each of Z and Z' is independently present or absent, but if present is independently 1-5 consecutive nucleotides, non-nucleotide moieties unconventional moieties or a combination thereof or a drug or vitamin moiety covalently attached at the 3' terminus of the strand in which it is present; wherein the sequence of (N')y is complementary to the sequence of (N)x; and wherein the sequence of (N')y comprises a sense strand and (N)x comprises an antisense strand set forth in any one of the oligonucleotide pairs SEQ ID NOS:3 and 12; SEQ ID NOS:4 and 13; SEQ ID NOS:5 and 14; SEQ ID NOS:6 and 15; SEQ ID NOS:7 and 16; SEQ ID NOS:8 and 17; SEQ ID NOS:9 and 18; SEQ ID NOS:10 and 19; or SEQ ID NOS:11 and 20.

Molecules encompassed by the description of Structure (A2) are also referred to herein as "18+1" or "18+1 mer". In preferred embodiments, N1 (nucleotide in position 1 of the antisense strand) is mismatched to the DDIT4 mRNA and the sense strand and antisense strand comprise sequence pairs set forth in any of SEQ ID NOS:21 and 30; SEQ ID NOS:22 and 31; SEQ ID NOS:23 and 32; SEQ ID NOS:24 and 33; SEQ ID NOS:25 and 34; SEQ ID NOS:26 and 35; SEQ ID NOS:27 and 36; SEQ ID NOS:28 and 37; or SEQ ID NOS:29 and 38.

In Structure A2, the antisense strand is shown in the 5'>3' orientation and the sense strand is shown in the 3'>5' orientation, whereas in the SEQ ID NO and tables the sequences are provided in the 5'>3' orientation.

In some embodiments, the sense strand (N')y and the antisense strand (N)x each of which is 18 nucleotides in length, useful in generating dsRNA compounds, are presented in Table 1. Preferred sense strands and complementary antisense strands, each of which is 19 nucleotides in length are shown in Table 2, infra.

In certain embodiments of Structure (A2), (N)x of a nucleic acid molecule (e.g., a dsRNA molecule) as disclosed herein includes a sequence corresponding to any one of the antisense sequences SEQ ID NO:12-20. In certain preferred embodiments, the nucleic acid molecule is a duplex of 19 nucleotides in length and (N)x and (N')y comprise the sequence pairs shown in Table 1. In certain preferred embodiments, the nucleic acid molecule is a duplex of 19 nucleotides in length and N1-(N)x and N2-(N')y comprise the sequence pairs shown in Table 2.

In some embodiments of Structure (A2), the sequence of (N')y is fully complementary to the sequence of (N)x. In various embodiments sequence of N2-(N')y is fully complementary to the sequence of N1-(N)x. In some embodiments (N)x comprises an antisense sequence that is fully complementary to about 17 to about 39 consecutive nucleotides in the DDIT4 mRNA set forth in SEQ ID NO:1. In other embodiments (N)x comprises an antisense sequence that is substantially complementary to about 17 to about 39 consecutive nucleotides in the DDIT4 mRNA set forth in SEQ ID NO:1.

In some embodiments of Structure (A2), N1 and N2 form a Watson-Crick base pair. In other embodiments N1 and N2 form a non-Watson-Crick base pair.

In some embodiments of Structure (A2), x=y=18, x=y=19 or x=y=20. In preferred embodiments, x=y=18. When x=18 in N1-(N)x, N1 refers to position 1 and positions 2-19 are included in (N)18 in the antisense strand. When y=18 in N2-(N')y, N2 refers to position 19 and positions 1-18 are included in (N')18 in the sense strand.

In some embodiments of Structure (A2), N1 is covalently bound to (N)x and is mismatched to the DDIT4 mRNA set forth in SEQ ID NO:1. In various embodiments N1 is covalently bound to (N)x and is a DNA moiety complementary to the DDIT4 mRNA set forth in SEQ ID NO:1. In some embodiments a base pair is formed between a deoxyribonucleotide and a ribonucleotide, for example between T and rA or between dU and rA.

In some embodiments of Structure (A2), the double stranded nucleic acid molecule is a siRNA, siNA or a miRNA. The double stranded nucleic acid molecules as provided herein are also referred to as "duplexes". In some embodiments of nucleic acid molecules (e.g., dsRNA molecules) according to Structure (A2) as disclosed herein, the double stranded nucleic acid molecule is a chemically modified siRNA.

In some embodiments, N1 is mismatched to the DDIT4 mRNA target sequence and is a natural uridine or a modified uridine (e.g. 2'OMe sugar modified). In some embodiments, N1 is mismatched to the DDIT4 mRNA target sequence and is a natural riboadenosine or a modified riboadenosine.

In some embodiments, x=y=18 and N1 is selected from a natural uridine, a modified uracil, a natural adenosine, a modified adenine.

In some embodiments, x=y=18 and N1 is an unmodified or modified (i.e. 2'O-methyl sugar modified) RNA nucleotide complementary to the DDIT4 mRNA target sequence.

In some embodiments, x=y=18 and N1 is a DNA nucleotide complementary to the DDIT4 mRNA target sequence and is a deoxyuridine, a deoxyadenosine or thymidine.

In some embodiments, N1 is an adenosine or deoxyadenosine and is mismatched to guanosine or cytosine in the target mRNA (SEQ ID NO:1).

In some embodiments, N1 is uridine or deoxyuridine and is mismatched to guanosine or cytosine in the target mRNA (SEQ ID NO:1).

In some embodiments, N1 is an adenosine or deoxyadenosine and is mismatched to adenosine in the target mRNA (SEQ ID NO:1).

In some embodiments, N1 is uridine or deoxyuridine and is mismatched to uridine in the target mRNA (SEQ ID NO:1).

In preferred embodiments, N2 is complementary to N1.

In some embodiments of Structure (A2), N1 is a 2'OMe sugar-modified uridine or a 2'OMe sugar-modified adenosine. In certain embodiments of structure (A2), N2 is a 2'OMe sugar modified ribonucleotide or a deoxyribonucleotide.

In some embodiments the double-stranded nucleic acid molecule comprises a sense strand and an antisense strand described as DDIT4_41a (SEQ ID NOS:21 and 30). In some embodiments the double-stranded nucleic acid molecule comprises a sense strand and an antisense strand described as DDIT4_43a (SEQ ID NOS:22 and 31). In some embodiments the double-stranded nucleic acid molecule comprises a sense strand and an antisense strand described as DDIT4_46a (SEQ ID NOS:23 and 32). In some embodiments the double-stranded nucleic acid molecule comprises a sense strand and an antisense strand described as DDIT4_55a (SEQ ID NOS:24 and 33). In some embodiments the double-stranded nucleic acid molecule comprises a sense strand and an antisense strand described as DDIT4_59a (SEQ ID NOS:25 and 34). In some embodiments the double-stranded nucleic acid molecule comprises a sense strand and an antisense strand described as DDIT4_60a (SEQ ID NOS:26 and 35). In some embodiments the double-stranded nucleic acid molecule comprises a sense strand and an antisense strand described as DDIT4_61a (SEQ ID NOS:27 and 36). In some embodiments the double-stranded nucleic acid molecule comprises a sense strand and an antisense strand described as DDIT4_62a (SEQ ID NOS:28 and 37). In some embodiments the double-stranded nucleic acid molecule comprises a sense strand and an antisense strand described as DDIT4_63u (SEQ ID NOS:29 and 38).

In some embodiments the dsRNA includes an antisense strand and a sense strand having a DDIT4 antisense and sense sequences selected from any one of the pairs set forth in Table 2. In some embodiments the antisense and sense strands are selected from the oligonucleotide pairs identified herein as DDIT4_41a (SEQ ID NOS: 21 and 30), DDIT4_43a (SEQ ID NOS: 22 and 31), DDIT4_46a (SEQ ID NOS: 23 and 32), DDIT4_55a (SEQ ID NOS: 24 and 33), DDIT4_59a (SEQ ID NOS: 25 and 34), DDIT4_60a (SEQ ID NOS: 26 and 35), DDIT4_61a (SEQ ID NOS: 27 and 36), DDIT4_62a (SEQ ID NOS: 28 and 37), and DDIT4_63u (SEQ ID NOS: 29 and 38).

In some embodiments the double stranded nucleic acid molecule includes the antisense strand set forth in SEQ ID NO:30 and sense strand set forth in SEQ ID NO:21; identified herein as DDIT4_41a. In some embodiments the double stranded nucleic acid molecule has the structure

```
5'   UAUGCUACAGUACUGAGGG-Z 3'   (antisense SEQ ID NO: 30)
     |||||||||||||||||||
3' Z'-AUACGAUGUCAUGACUCCC-z" 5' (sense SEQ ID NO: 21)
``` wherein each of A, C, G, U is independently an unmodified or modified ribonucleotide, or an unconventional moiety;

wherein each "|" represents base pairing between the ribonucleotides/unconventional moieties;

wherein each of Z and Z' is independently present or absent, but if present is independently 1-5 consecutive nucleotides, non-nucleotide moieties, unconventional moieties or a combination thereof or a conjugate moiety covalently attached at the 3' terminus of the strand in which it is present; and wherein z" may be present or absent, but if present is a capping moiety or a conjugate moiety covalently attached at the 5' terminus of N2-(N')y; or a pharmaceutically acceptable salt of such molecule.

In some embodiments provided is a double stranded nucleic acid molecule wherein the antisense strand (SEQ ID NO:30) includes one or more 2'OMe sugar modified pyrimidines and or purines, a 2'-5' ribonucleotide in position 5, 6, 7 or 8, and a 3' terminal (3'end) nucleotide or non-nucleotide overhang. In some embodiments the sense strand (SEQ ID NO:21) includes one or more 2'OMe sugar modified pyrimidines and or purines, optionally 4 or 5 consecutive 2'5' nucleotides at the 3' terminal or penultimate positions, a nucleotide or non-nucleotide moiety covalently attached at the 3' terminus and a cap moiety covalently attached at the 5' terminus (5' end). In other embodiments the sense strand (SEQ ID NO:21) includes one or more 2'OMe pyrimidine, a nucleotide or non-nucleotide moiety covalently attached at the 3' terminus and a cap moiety covalently attached at the 5' terminus.

In some embodiments provided is a double stranded nucleic acid molecule wherein the antisense strand (SEQ ID NO:30) includes 2'OMe sugar modified ribonucleotides at positions (5'>3') 1, 3, 8, 11, and 15, a 2'-5' ribonucleotide at position 6, and a C3Pi-C3OH or C3Pi-C3Pi moiety covalently attached to the 3' terminus; and the sense strand (SEQ ID NO:21) is selected from a sense strand which includes a) 2'OMe sugar modified ribonucleotides at positions (5'>3') 16 and 18 a C3OH or C3Pi moiety covalently attached at the 3' terminus; and an inverted abasic deoxyribonucleotide moiety covalently attached at the 5' terminus; or b) 2'OMe sugar modified ribonucleotides at positions (5'>3') 16 and 18 a C3OH or C3Pi moiety covalently attached at the 3' terminus; and an C6 amino moiety covalently attached at the 5' terminus; or c) 2'OMe sugar modified ribonucleotides at positions (5'>3') 16 and 18, a C3OH or C3Pi moiety covalently attached at the 3' terminus; and an THNB moiety covalently attached at the 5' terminus; or d) 2'-5' linked ribonucleotides at positions 15, 16, 17, 18 and 19, a C3OH or C3Pi moiety covalently attached at the 3' terminus and optionally a capping moiety (i.e. inverted abasic deoxyribonucleotide moiety) covalently attached at the 5' terminus.

Such molecules optionally include a Pi (inorganic phosphate) or a conjugate moiety covalently attached to the 5' terminus of the sense strand instead of a capping moiety Provided herein is a double stranded nucleic acid molecule wherein the antisense strand (SEQ ID NO:30) includes 2'OMe sugar modified ribonucleotides at positions (5'>3') 1, 3, 8, 11, and 15, a 2'-5' ribonucleotide at position 6, and a C3Pi-C3Pi moiety covalently attached to the 3' terminus; and the sense strand (SEQ ID NO:21) having 2'OMe sugar modified ribonucleotides at positions (5'>3') 16 and 18, a C3Pi 3' terminal overhang; and an inverted abasic deoxyribonucleotide moiety covalently attached at the 5' terminus.

Provided herein is a double stranded nucleic acid molecule wherein the antisense strand (SEQ ID NO:30) includes 2'OMe sugar modified ribonucleotides at positions (5'>3') 1, 3, 8, 11, and 15, a 2'-5' ribonucleotide at position 6, and a C3Pi-C3Pi moiety covalently attached to the 3' terminus; and the sense strand (SEQ ID NO:21) having 2'OMe sugar modified ribonucleotides at positions (5'>3') 16 and 18, a C3Pi 3' terminal overhang; and an C6 amino moiety covalently attached at the 5' terminus.

In some embodiments, the double stranded nucleic acid molecule includes the antisense strand set forth in SEQ ID NO:31 and sense strand set forth in SEQ ID NO:22; identified herein as DDIT4_43a. In some embodiments the double stranded nucleic acid molecule has the structure

```
5'    UGUCUGUAAGAUAGCUGCC-Z 3'    (antisense SEQ ID NO: 31)
      ||||||||||||||||||
3' Z'-ACAGACAUUCUAUCGACGG-z" 5'   (sense SEQ ID NO: 22)
``` wherein each of A, C, G, U is independently an unmodified or modified ribonucleotide, or an unconventional moiety;

wherein each "|" represents base pairing between the ribonucleotides/unconventional moieties;

wherein each of Z and Z' is independently present or absent, but if present is independently 1-5 consecutive nucleotides, non-nucleotide moieties, unconventional moieties or a combination thereof or a conjugate moiety covalently attached at the 3' terminus of the strand in which it is present; and wherein z" may be present or absent, but if present is a capping moiety or a conjugate moiety covalently attached at the 5' terminus of N2-(N')y; or a pharmaceutically acceptable salt of such molecule.

In some embodiments, the double stranded nucleic acid molecule includes the antisense strand set forth in SEQ ID NO:32 and sense strand set forth in SEQ ID NO:23; identified herein as DDIT4_46a. In some embodiments the double stranded nucleic acid molecule has the structure

```
5'    UACUCGCAGUCCGAGCUCU-Z 3'    (antisense SEQ ID NO: 32)
      ||||||||||||||||||
3' Z'-AUGAGCGUCAGGCUCGAGA-z" 5'   (sense SEQ ID NO: 23)
``` wherein each of A, C, G, U is independently an unmodified or modified ribonucleotide, or an unconventional moiety;

wherein each "|" represents base pairing between the ribonucleotides/unconventional moieties;

wherein each of Z and Z' is independently present or absent, but if present is independently 1-5 consecutive nucleotides, non-nucleotide moieties, unconventional moieties or a combination thereof or a conjugate moiety covalently attached at the 3' terminus of the strand in which it is present; and wherein z" may be present or absent, but if present is a capping moiety or a conjugate moiety covalently attached at the 5' terminus of N2-(N')y; or a pharmaceutically acceptable salt of such molecule.

In some embodiments, the double stranded nucleic acid molecule includes the antisense strand set forth in SEQ ID NO:33 and sense strand set forth in SEQ ID NO:24; identified herein as DDIT4_55a. In some embodiments the double stranded nucleic acid molecule has the structure

```
5'    UGUUCUAGAUGGAAGACCC-Z 3'    (antisense SEQ ID NO: 33)
      ||||||||||||||||||
3' Z'-ACAAGAUCUACCUUCUGGG-z" 5'   (sense SEQ ID NO: 24)
``` wherein each of A, C, G, U is independently an unmodified or modified ribonucleotide, or an unconventional moiety;

wherein each "|" represents base pairing between the ribonucleotides/unconventional moieties;

wherein each of Z and Z' is independently present or absent, but if present is independently 1-5 consecutive nucleotides, non-nucleotide moieties, unconventional moieties or a combination thereof or a conjugate moiety covalently attached at the 3' terminus of the strand in which it is present; and wherein z" may be present or absent, but if present is a capping moiety or a conjugate moiety covalently attached at the 5' terminus of N2-(N')y; or a pharmaceutically acceptable salt of such molecule.

In some embodiments, the double stranded nucleic acid molecule includes the antisense strand set forth in SEQ ID NO:34 and sense strand set forth in SEQ ID NO:25; identified herein as DDIT4_59a. In some embodiments the double stranded nucleic acid molecule has the structure

```
5'     UCUGCCUCUAGUCUCCACC-Z 3'    (antisense SEQ ID NO: 34)
       |||||||||||||||||||
3' Z'-AGACGGAGAUCAGAGGUGG-z" 5'    (sense SEQ ID NO: 25)
``` wherein each of A, C, G, U is independently an unmodified or modified ribonucleotide, or an unconventional moiety;

wherein each "|" represents base pairing between the ribonucleotides/unconventional moieties;

wherein each of Z and Z' is independently present or absent, but if present is independently 1-5 consecutive nucleotides, non-nucleotide moieties, unconventional moieties or a combination thereof or a conjugate moiety covalently attached at the 3' terminus of the strand in which it is present; and wherein z" may be present or absent, but if present is a capping moiety or a conjugate moiety covalently attached at the 5' terminus of N2-(N')y; or a pharmaceutically acceptable salt of such molecule.

In some embodiments, the double stranded nucleic acid molecule includes the antisense strand set forth in SEQ ID NO:35 and sense strand set forth in SEQ ID NO:26; identified herein as DDIT4_60a. In some embodiments the double stranded nucleic acid molecule has the structure

```
5'     UUCGUCUCUGUCUUGGAGG-Z 3'    (antisense SEQ ID NO: 35)
       |||||||||||||||||||
3' Z'-AAGCAGAGACAGAACCUCC-z" 5'    (sense SEQ ID NO: 26)
``` wherein each of A, C, G, U is independently an unmodified or modified ribonucleotide, or an unconventional moiety;

wherein each "|" represents base pairing between the ribonucleotides/unconventional moieties;

wherein each of Z and Z' is independently present or absent, but if present is independently 1-5 consecutive nucleotides, non-nucleotide moieties, unconventional moieties or a combination thereof or a conjugate moiety covalently attached at the 3' terminus of the strand in which it is present; and wherein z" may be present or absent, but if present is a capping moiety or a conjugate moiety covalently attached at the 5' terminus of N2-(N')y; or a pharmaceutically acceptable salt of such molecule.

In some embodiments, the double stranded nucleic acid molecule includes the antisense strand set forth in SEQ ID NO:36 and sense strand set forth in SEQ ID NO:27; identified herein as DDIT4_61a. In some embodiments the double stranded nucleic acid molecule has the structure

```
5'     UACAACUCAAUGAGCUUCC-Z 3'    (antisense SEQ ID NO: 36)
       |||||||||||||||||||
3' Z'-AUGUUGAGUUACUCGAAGG-z" 5'    (sense SEQ ID NO: 27)
``` wherein each of A, C, G, U is independently an unmodified or modified ribonucleotide, or an unconventional moiety;

wherein each "|" represents base pairing between the ribonucleotides/unconventional moieties;

wherein each of Z and Z' is independently present or absent, but if present is independently 1-5 consecutive nucleotides, non-nucleotide moieties, unconventional moieties or a combination thereof or a conjugate moiety covalently attached at the 3' terminus of the strand in which it is present; and wherein z" may be present or absent, but if present is a capping moiety or a conjugate moiety covalently attached at the 5' terminus of N2-(N')y; or a pharmaceutically acceptable salt of such molecule.

In some embodiments, the double stranded nucleic acid molecule includes the antisense strand set forth in SEQ ID NO:37 and sense strand set forth in SEQ ID NO:28; identified herein as DDIT4_62a. In some embodiments the double stranded nucleic acid molecule has the structure

```
5'    UAGGCUUAAACGCAGCUGC-Z  3'    (antisense SEQ ID NO: 37)
      ||||||||||||||||||
3' Z'-AUCCGAAUUUGCGUCGACG-z" 5'    (sense SEQ ID NO: 28)
``` wherein each of A, C, G, U is independently an unmodified or modified ribonucleotide, or an unconventional moiety;

wherein each "|" represents base pairing between the ribonucleotides/unconventional moieties;

wherein each of Z and Z' is independently present or absent, but if present is independently 1-5 consecutive nucleotides, non-nucleotide moieties, unconventional moieties or a combination thereof or a conjugate moiety covalently attached at the 3' terminus of the strand in which it is present; and Wherein z" may be present or absent, but if present is a capping moiety or a conjugate moiety covalently attached at the 5' terminus of N2-(N')y; or A pharmaceutically acceptable salt of such molecule.

In some embodiments the double stranded nucleic acid molecule includes the antisense strand set forth in SEQ ID NO:38 and sense strand set forth in SEQ ID NO:29; identified herein as DDIT4_63u. In some embodiments the double stranded nucleic acid molecule has the structure

```
5'    AUUUCAUGCUACAGUACUG-Z  3'    (antisense SEQ ID NO: 38)
      ||||||||||||||||||
3' Z'-UAAAGUACGAUGUCAUGAC-z" 5'    (sense SEQ ID NO: 29)
``` wherein each "|" represents base pairing between the ribonucleotides;

wherein each of A, C, G, U is independently an unmodified or modified ribonucleotide, or an unconventional moiety;

wherein each "|" represents base pairing between the ribonucleotides/unconventional moieties; wherein each of Z and Z' is independently present or absent, but if present is independently 1-5 consecutive nucleotides, non-nucleotide moieties, unconventional moieties or a combination thereof or a conjugate moiety covalently attached at the 3' terminus of the strand in which it is present; and wherein z" may be present or absent, but if present is a capping moiety or a conjugate moiety covalently attached at the 5' terminus of N2-(N')y; or a pharmaceutically acceptable salt of such molecule.

In preferred embodiments, the sense strand and antisense strand are each 19 nucleotides in length and the nucleic acid molecule comprises a sequence pair selected from any of SEQ ID NOS:21 and 30; SEQ ID NOS:22 and 31; SEQ ID NOS:23 and 32; SEQ ID NOS:24 and 33; SEQ ID NOS:25 and 34; SEQ ID NOS:26 and 35; SEQ ID NOS:27 and 36; SEQ ID NOS:28 and 37; or SEQ ID NOS:29 and 38.

The nucleic acids provided herein are preferably dsRNA molecules that possess modifications which may increase activity, increase stability, facilitate cellular uptake and endosomal release, enhance plasma retention, and/or minimize toxicity when compared to the corresponding unmodified dsRNA compound. These molecules, when admixed with a pharmaceutical vehicle provide effective, safe and patient compliant therapeutic compounds useful in treating a variety of diseases disorders.

The dsRNA molecules provided herein are double-stranded chemically modified oligonucleotides. In some embodiments the sense oligonucleotide and the antisense oligonucleotide useful in generating the chemically modified dsRNA molecules RNAs are selected from sense strand oligonucleotides set forth in SEQ ID NOS:3-11 and corresponding antisense strand oligonucleotide set forth in SEQ ID NOS:12-20. In preferred embodiments the antisense strand is complementary to a 18 nucleotide contiguous sequence in the DDIT4 mRNA and the 3' terminal ribonucleotide of the antisense strand (i.e. position 19 in a 19-mer) is mismatched to the DDIT4 mRNA. In preferred embodiments a G or C in the target DDIT4 mRNA is mismatched to a U, A or T at the 5' terminus of the antisense strand (position 1 of AS). In preferred embodiments the sense strand and antisense strand comprise sequence pairs set forth in any of SEQ ID NOS:21 and 30; SEQ ID NOS:22 and 31; SEQ ID NOS:23 and 32; SEQ ID NOS:24 and 33; SEQ ID NOS:25 and 34; SEQ ID NOS:26 and 35; SEQ ID NOS:27 and 36; SEQ ID NOS:28 and 37; or SEQ ID NOS:29 and 38.

In various embodiments, in a nucleic acid molecule (e.g., dsRNA molecule) as disclosed herein, the antisense strand may be 18 to 49 nucleotides in length (e.g., 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 nucleotides in length); or 18-35 nucleotides in length; or 18-30 nucleotides in length; or 18-25 nucleotides in length; or 18-23 nucleotides in length; or 19-21 nucleotides in length; or 25-30 nucleotides in length; or 26-28 nucleotides in length. In some embodiments, the dsRNA is an asymmetrical molecule, for example 15 nucleotides on the sense strand and 18-25 nucleotide on the antisense strand. In some embodiments, the dsRNA is a tandem or RNAstar molecule with three dsRNA arms. In some embodiments, the dsRNA is a dicer substrate, for example 27 to 49 nucleotides in length. In some embodiments of a nucleic acid molecule (e.g., dsRNA molecule) as disclosed herein, the antisense strand is 19 nucleotides in length. Similarly the sense strand of a nucleic acid molecule (e.g., dsRNA molecule) as disclosed herein may be 15 to 49 nucleotides in length (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 nucleotides in length); or 15-35 nucleotides in length; or 15-30 nucleotides in length; or 15-25 nucleotides in length; or 18-23 nucleotides in length; or 19-21 nucleotides in length; or 25-30 nucleotides in length; or 26-28 nucleotides in length. In some embodiments of a nucleic acid molecule (e.g., dsRNA molecule) as disclosed herein, the sense strand is 19 nucleotides in length. In some embodiments of a nucleic acid molecule (e.g., dsRNA molecule) as disclosed herein, each of the antisense strand and the sense strand are 19 nucleotides in length. The duplex region of a nucleic acid molecule (e.g., dsRNA molecule) as disclosed herein may be 18-49 nucleotides in length (e.g., about 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 nucleotides in length), 18-35 nucleotides in length; or 18-30 nucleotides in length; or 18-25 nucleotides in length; or 18-23 nucleotides in length; or 18-21 nucleotides in length; or 25-30 nucleotides in length; or 25-28 nucleotides in length. In various embodiments of a nucleic acid molecule (e.g., dsRNA molecule) as disclosed herein, the duplex region is 19 nucleotides in length. In some embodiments a short asymmetric siRNA is preferred (as described in Chu and Rana, 2008).

In certain embodiments, the sense strand and the antisense strand of a nucleic acid (e.g., a dsRNA nucleic acid molecule) as provided herein are separate oligonucleotide strands. In some embodiments, the separate sense strand and antisense strand form a double stranded structure, also known as a duplex, via hydrogen bonding, for example, Watson-Crick base pairing. In some embodiments one or more nucleotide pairs form non-Watson-Crick base pairing. In some embodiments the sense strand and the antisense strand are two separate strands that are covalently linked to each other. In other embodiments, the sense strand and the antisense strands are part of a single oligonucleotide having both a sense and antisense region; in some preferred embodiments the oligonucleotide has a hairpin structure.

In certain embodiments, the nucleic acid molecule is a double stranded nucleic acid (dsRNA) molecule that is symmetrical with regard to overhangs, and has a blunt end on both ends. In other embodiments the nucleic acid molecule is a dsRNA molecule that is symmetrical with regard to overhangs, and has a nucleotide or a non-nucleotide overhang or a combination of a nucleotide and non-nucleotide overhang on both ends of the dsRNA molecule. In certain preferred embodiments, the nucleic acid molecule is a dsRNA molecule that is asymmetrical with regard to overhangs, and has a blunt end on one end of the molecule and an overhang on the other end of the molecule. In some embodiments an asymmetrical dsRNA molecule has a 3'-overhang on one side of a duplex occurring on the sense strand; and a blunt end on the other side of the molecule occurring on both the 5'-end of the sense strand and the 5'-end of the antisense strand. In some embodiments an asymmetrical dsRNA molecule has a 5'-overhang on one side of a duplex occurring on the sense strand; and a blunt end on the other side of the molecule occurring on both the 3'-end of the sense strand and the 3'-end of the antisense strand. In other embodiments an asymmetrical dsRNA molecule has a 3'-overhang on one side of a duplex occurring on the antisense strand; and a blunt end on the other side of the molecule occurring on both the 5'-end of the sense strand and the 5'-end of the antisense strand. In some embodiments an asymmetrical dsRNA molecule has a 5'-overhang on one side of a duplex occurring on the antisense strand; and a blunt end on the other side of the molecule occurring on both the 3'-end of the sense strand and the 3'-end of the antisense strand. In some embodiments the overhangs are nucleotide overhangs, in other embodiments the overhangs are non-nucleotide overhangs. In some embodiments the overhangs are 5' overhangs; in alternative embodiments the overhangs are 3' overhangs.

In some embodiments, the sense strand includes a capping moiety or a conjugate moiety (z")

In some embodiments, the nucleic acid molecule has a hairpin structure (having the sense strand and antisense strand on one oligonucleotide), with a loop structure on one end and a blunt end on the other end. In some embodiments, the nucleic acid molecule has a hairpin structure, with a loop structure on one end and an overhang end on the other end; in certain embodiments, the overhang is a 3'-overhang; in certain embodiments the overhang is a 5'-overhang; in certain embodiments the overhang is on the sense strand; in certain embodiments the overhang is on the antisense strand.

The nucleic acid molecule (e.g., dsRNA molecule) disclosed herein may include one or more modifications or modified nucleotides such as described herein. For example, a nucleic acid molecule (e.g., dsRNA molecule) as provided herein may include a modified nucleotide having a modified sugar; a modified nucleotide having a modified nucleobase; or a modified nucleotide having a modified phosphate group. Similarly, a nucleic acid molecule (e.g., dsRNA molecule) as provided herein may include a modified phosphodiester backbone and/or may include a modified terminal phosphate group.

A nucleic acid molecule (e.g., dsRNA molecules) as provided herein may have one or more ribonucleotides that include a modified sugar moiety, for example as described herein. A non-limiting example of a modified sugar moiety is a 2'alkoxy modified sugar moiety. In some preferred embodiments the nucleic acid comprises at least one 2'-O-methyl sugar modified ribonucleotide.

A nucleic acid molecule (e.g., dsRNA molecule) as provided herein may have one or more modified nucleobase(s), for example as described herein.

A nucleic acid molecule (e.g., dsRNA molecule) as provided herein may have one or more modifications to the phosphodiester backbone, for example as described herein.

A nucleic acid molecule (e.g., dsRNA molecule) as provided herein may have one or more modified phosphate group(s), for example as described herein.

In various embodiments, the provided nucleic acid molecule (e.g., dsRNA molecule) may include an unmodified antisense strand and a sense strand having one or more modifications. In some embodiments the provided nucleic acid molecule (e.g., dsRNA molecule) may include an unmodified sense strand and an antisense strand having one or more modifications. In preferred embodiments the provided nucleic acid molecule (e.g., dsRNA molecule) may include one or more modified nucleotides in the both the sense strand and the antisense strand.

A nucleic acid molecule (e.g., dsRNA molecules) as provided herein may include a cleavable or non-cleavable phosphate group at the 5' end of the sense and/or the antisense strand (i.e. a 5'-terminal phosphate group). In some embodiments a dsRNA molecule disclosed herein may include a phosphate group at the 5' terminus of the antisense strand.

A nucleic acid molecule (e.g., dsRNA molecules) as provided herein may include a phosphate group at the 3' end of the sense and/or the antisense strand (i.e. a 3'-terminal phosphate group). In some embodiments a dsRNA molecule disclosed herein may include a phosphate group at the 3' terminus of the antisense strand.

In some embodiments a nucleic acid molecule (e.g., dsRNA molecules) disclosed herein may include a phosphate group at the 3' terminus of the antisense strand and the sense strand.

In some embodiments a nucleic acid molecule (e.g., dsRNA molecules) disclosed herein the antisense strand and the sense strand of the nucleic acid molecule are non-phosphorylated at both the 3' terminus and at the 5' terminus.

In some embodiments provided is a double-stranded nucleic acid molecule wherein the antisense strand is selected from any one of SEQ ID NOS:30-38 and includes a mirror nucleotide or a 2'-5' linked ribonucleotide in one or more of positions 5, 6, 7 or 8 (5'-3'), and a nucleotide or non-nucleotide moiety covalently attached at the 3' terminus. In some embodiments the antisense strand further includes one or more 2'OMe sugar modified ribonucleotides. In some embodiments 1, 2, 3, 4, 5, 6 or 7 pyrimidine ribonucleotides in the antisense strand are 2'OMe sugar modified pyrimidine ribonucleotides. In some embodiments the sense strand is selected from the complementary sequences set forth in SEQ ID NOS; 21-29 and includes 4 or 5 consecutive 2'-5' linked nucleotides at the 3' terminal or penultimate positions, a nucleotide or non-nucleotide moiety covalently attached at the 3' terminus, one or more 2'OMe sugar modified ribonucleotides, and a capping moiety covalently attached at the 5' terminus. The dsRNA molecule may include a 5' phosphate on the antisense strand.

In some embodiments provided is a double-stranded nucleic acid molecule wherein the sense strand is set forth in SEQ ID NO:21 and includes (5'>3') 2'OMe sugar modified ribonucleotides at positions 16 and 18, and a 3' terminal nucleotide or non-nucleotide overhang covalently attached to the 3' terminus; and the antisense strand is set forth in SEQ ID NO:30 includes (5'>3') 2'OMe sugar modified ribonucleotides at positions 1, 3, 8, 11, and 15, a 3' terminal nucleotide or non-nucleotide overhang; and a capping moiety covalently attached at the 5' terminus. In some embodiments the antisense strand further includes a 2'-5' linked ribonucleotide at position 6, at position 7 or at positions 6 and 7. In some embodiments the capping moiety is selected from an inverted deoxyabasic moiety, a c6 amino moiety and THNB. In some embodiments the sense strand comprises a 3' terminal dTdT overhang or a C3Pi or C3OH non-nucleotide overhang. In some embodiments the sense strand further includes 2'-O'methyl sugar modified ribonucleotides at one or more of positions 5, 8, 11 or 13.

In some embodiments provided is a double-stranded nucleic acid molecule wherein the sense strand is set forth in SEQ ID NO:21 and includes (5'>3') 2'OMe sugar modified ribonucleotides at positions 16 and 18, and a 3' terminal non-nucleotide C3Pi overhang covalently attached to the 3' terminus; and the antisense strand is set forth in SEQ ID NO:30 includes (5'>3') 2'OMe sugar modified ribonucleotides at positions 1, 3, 8, 11, and 15, a 3' terminal non-nucleotide C3Pi-C3OH overhang; and a capping moiety covalently attached at the 5' terminus. In some embodiments the capping moiety is selected from an inverted deoxyabasic moiety, a c6 amino moiety and THNB. In some embodiments the sense strand further includes 2'-O'methyl sugar modified ribonucleotides at positions 5, 8, 11 or 13.

In some embodiments provided is a double-stranded nucleic acid molecule wherein the sense strand is set forth in SEQ ID NO:29 and includes (5'>3') 2'OMe sugar modified ribonucleotides at positions 1, 4, 7, 9, 12 and 14, and a 3' terminal nucleotide or non-nucleotide overhang covalently attached to the 3' terminus; and the antisense strand is set forth in SEQ ID NO:38 includes (5'>3') 2'OMe sugar modified ribonucleotides at positions 3, 5 and 18, a 3' terminal nucleotide or non-nucleotide overhang; and a capping moiety covalently attached at the 5' terminus. In some embodiments the antisense strand further includes a 2'-5' linked ribonucleotide at position 6, at position 7 or at positions 6 and 7. In some embodiments the capping moiety is selected from an inverted deoxyabasic moiety, a c6 amino moiety and THNB. In some embodiments the sense strand comprises a 3' terminal dTdT overhang or a C3Pi or C3OH non-nucleotide overhang. In some embodiments the antisense strand further includes 2'-O'methyl sugar modified ribonucleotides at one or more of positions 10, 11, 12 or 13.

In some embodiments provided is a double-stranded nucleic acid molecule wherein the sense strand is set forth in SEQ ID NO:29 and includes (5'>3') 2'OMe sugar modified ribonucleotides at positions 3, 5 and 18, a 3' terminal non-nucleotide C3Pi overhang covalently attached to the 3' terminus; and the antisense strand is set forth in SEQ ID NO:38 includes (5'>3') 2'OMe sugar modified ribonucleotides at positions 1, 3, 8, 11, and 15, a 3' terminal non-nucleotide C3Pi-C3OH overhang; and a capping moiety covalently attached at the 5' terminus. In some embodiments the capping moiety is selected from an inverted deoxyabasic moiety, a c6 amino moiety and THNB. In some embodiments the sense strand further includes 2'-O'methyl sugar modified ribonucleotides at positions 10 and 12 or 11 and 13.

In some embodiments of Structure (A2), each N in (N)x of SEQ ID NOS:30-38 consists of an unmodified ribonucleotide. In some embodiments of Structure (A2) each N' in (N')y of SEQ ID NOS:22-29 consists of an unmodified ribonucleotide. In preferred embodiments at least one of N and/or N' comprises a chemically modified ribonucleotide, or an unconventional moiety. In some embodiments the unconventional moiety is selected from a mirror nucleotide, a 2'5' linked nucleotide, an abasic ribose moiety a deoxyribonucleotide, a threose nucleic acid (TNA), a pyrazolotriazine base modified nucleic acid analogue and an abasic deoxyribose moiety. In some embodiments the unconventional moiety is 2'5' linked ribonucleotide, a TNA or a mirror nucleotide (i.e.an L-DNA moiety). In some embodiments at least one of N or N' comprises a 2'OMe sugar-modified ribonucleotide. In some embodiments at least one of N or N' which is a pyrimidine ribonucleotide comprises a 2'OMe sugar-modified ribonucleotide In some embodiments of Structure (A2), the dsRNA compound is blunt ended, for example, wherein each of z", Z and Z' is absent. In an alternative embodiment, at least one of z", Z or Z' is present.

In various embodiments Z and Z' independently include one or more covalently linked modified and or unmodified nucleotides, including deoxyribonucleotides and ribonucleotides, or one or more unconventional moieties for example inverted abasic deoxyribose moiety, abasic ribose moiety, a mirror nucleotide or a pyrazolotriazine nucleotide analogue ; one or more non-nucleotide C3 moiety or a derivative thereof, non-nucleotide C4 moiety or a derivative thereof or non-nucleotide C5 moiety or a derivative thereof, an non-nucleotide amino-C6 moiety or a derivative thereof, as defined herein, and the like or a conjugate moiety. In some embodiments Z' is absent and Z is present and includes one or more non-nucleotide C3 moieties. In some embodiments Z is absent and Z' is present and includes one or more non-nucleotide C3 moieties. In some embodiments each of Z and Z' independently comprises one or more dT, non-nucleotide C3 moieties, or a conjugate moiety. In some embodiments, Z and/or Z' is a conjugate moiety selected from a vitamin, a drug, a lipid, a polyalkylamine, a peptide or a fluorophore covalently attached to the terminus at which it is present.

In some embodiments, z" is present and is a capping moiety selected from a mirror nucleotide, an abasic moiety, an amino C6 moiety, a phenyl hydrocarbyl moiety and an inverted abasic moiety or is a conjugate moiety. In some embodiments of Structure (A2) each of Z and Z' includes an abasic moiety, for example a deoxyriboabasic moiety (referred to herein as "dAb") or riboabasic moiety (referred to herein as "rAb"). In some embodiments each of Z and/or Z' comprises two covalently linked abasic moieties and is for example dAb-dAb or rAb-rAb or dAb-rAb or rAb-dAb, wherein each moiety is covalently attached to an adjacent moiety, preferably via a phospho-based bond. In some embodiments the phospho-based bond includes a phosphorothioate, a phosphonoacetate or a phosphodiester bond. In preferred embodiments the phospho-based bond is a phosphodiester bond.

In some embodiments each of Z and/or Z' independently includes an alkyl moiety, optionally propane [$(CH2)_3$] moiety (C3) or a derivative thereof including propanol (C3OH)

and phospho derivative of propanediol ("C3Pi"). In some embodiments each of Z and/or Z' includes two alkyl moieties and in some examples is C3Pi-C3OH or C3Pi-C3Pi. In the example of C3Pi-C3OH, the 3' terminus of the antisense strand and/or the 3' terminus of the sense strand is covalently attached to a C3 moiety via a phospho-based bond and the C3 moiety is covalently bound to a C3OH moiety via a phospho-based bond. In some embodiments the phospho-based bonds include a phosphorothioate, a phosphonoacetate or a phosphodiester bond. In preferred embodiments the phospho-based bond is a phosphodiester bond.

In specific embodiments of Structure (A2), Z comprises C3Pi-C3OH or C3Pi-C3Pi. In specific embodiments of Structure (A2), Z' comprises C3Pi or C3OH. In some embodiments of Structure (A2), a double stranded nucleic acid molecule includes a C3Pi-C3Pi moiety covalently attached to the 3' terminus of the antisense strand and a C3Pi or C3OH moiety covalently attached to the 3' terminus of the sense strand.

In other embodiments a compound of Structure (A2) includes at least one ribonucleotide modified in its sugar residue. In some embodiments the compound comprises a modification at the 2' position of the sugar residue. In some embodiments the modification in the 2' position comprises the presence of an amino, a fluoro, an alkoxy or an alkyl moiety. In certain embodiments the 2' modification includes an alkoxy moiety. In preferred embodiments the alkoxy moiety is a methoxy moiety (also referred to as 2'-O-methyl; 2'OMe; 2'OMe; 2'-OCH$_3$). In some embodiments a nucleic acid compound includes 2'OMe sugar modified alternating ribonucleotides in one or both of the antisense strand and the sense strand. In other embodiments a compound includes 2'OMe sugar modified ribonucleotides in the antisense strand, N$^1$—(N)x, only. In some embodiments, the 2'OMe sugar modified ribonucleotides alternate with unmodified nucleotides. In certain embodiments the middle ribonucleotide of the antisense strand; e.g. ribonucleotide in position 10 in a 19-mer strand, is unmodified. In various embodiments the nucleic acid compound includes at least 5 alternating 2'OMe sugar modified ribonucleotides and unmodified ribonucleotides. In additional embodiments a compound of Structure (A2) includes modified ribonucleotides in alternating positions wherein each ribonucleotide at the 5' terminus and at the 3' terminus of N$^1$—(N)x is modified in its sugar residue, and each ribonucleotide at the 5' terminus and at the 3' terminus of or N$^2$—(N)y is unmodified in its sugar residue. In various embodiments the ribonucleotides in alternating positions are modified at the 2' position of the sugar residue.

In some embodiments, the nucleic acid molecule comprises unmodified ribonucleotides, modified ribonucleotides and unconventional moieties. In some embodiments, (N)x (SEQ ID NOS:30-38) comprises unmodified and 2'-O-methyl (2'OMe) sugar modified ribonucleotides, and optionally a 2'-5' ribonucleotide in at least one of positions 5, 6, or 7; and (N')y (SEQ ID NOS:22-29) comprises unmodified ribonucleotides, at least one 2'5' ribonucleotide and/or 2'OMe modified ribonucleotide; z" is present; and each of Z and Z' is present and consists of a non-nucleotide moiety or a conjugate moiety covalently attached to the 3' terminus of the strand in which it is present. In preferred embodiments (N)x comprises 2'OMe sugar modified pyrimidine ribonucleotides; and (N')y comprises 2'OMe sugar modified pyrimidine ribonucleotides. In preferred embodiments, z" comprises an inverted abasic moiety, an amino C6 moiety or a THNB moiety; Z' comprises a C3Pi moiety; and Z comprises a C3Pi-C3OH or C3Pi-C3Pi moiety.

In some embodiments the nucleic acid compound includes at least 5 alternating 2'OMe sugar modified ribonucleotides and unmodified ribonucleotides, for example at positions 1, 3, 5, 7 and 9 or at positions 11, 13, 15, 17, 19 (5'>3'). In some embodiments, N1-(N)x of Structure (A2) includes 2'OMe sugar modified ribonucleotides in positions 2, 4, 6, 8, 11, 13, 15, 17 and 19. In some embodiments, N1-(N)x of Structure (A2) includes 2'OMe sugar modified ribonucleotides in positions 1, 3, 5, 7, 9, 11, 13, 15, 17 and 19. In some embodiments, N1-(N)x of Structure (A2) includes 2'OMe sugar modified ribonucleotides in one or more pyrimidines.

In some embodiments of Structure (A2), neither of the sense strand nor the antisense strand is phosphorylated at the 3' terminus and at the 5' terminus. In other embodiments one or both of the sense strand and/or the antisense strand are phosphorylated at the 3' termini. In other embodiments one or both of the sense strand and/or the antisense strand are phosphorylated at the 5' terminus.

In some embodiments the double stranded molecule disclosed herein includes one or more of the following modifications, in particular for a 19 mer duplex:

N in at least one of positions 5, 6, 7, 8, or 9 from the 5' terminus of the antisense strand is selected from a DNA, TNA, a 2'5' nucleotide or a mirror nucleotide;

N' in at least one of positions 9 or 10 from the 5' terminus of the sense strand is selected from a TNA, 2'5' nucleotide and a pseudouridine;

N' in 4, 5, or 6 consecutive positions at the 3' terminus of (N')y comprises a 2'5' ribonucleotide;

one or more pyrimidine ribonucleotides are 2' sugar modified in the sense strand, the antisense strand or both the sense strand and the antisense strand;

1, 2, 3, 4, 5, 6, 7, 8, 9, 10, 11, 12, 13, 14, 15, 16, 17, 18, or 19 N' is a TNA;

1, 2, or 3 N' is a pyrazolotriazine base modified nucleotide analogue.

In some embodiments the double stranded molecule disclosed herein includes a combination of the following modifications the antisense strand includes a DNA, TNA, a 2'5' nucleotide or a mirror nucleotide in at least one of positions 5, 6, 7, 8, or 9 from the 5' terminus;

the sense strand includes at least one of a TNA, a 2'5' nucleotide and a pseudouridine in positions 9 or 10 from the 5' terminus; and one or more pyrimidine ribonucleotides are 2' modified in the sense strand, the antisense strand or both the sense strand and the antisense strand.

In some embodiments the double stranded molecule disclosed herein includes a combination of the following modifications the antisense strand includes a DNA, 2'5' nucleotide or a mirror nucleotide in at least one of positions 5, 6, 7, 8, or 9 from the 5' terminus;

the sense strand includes 4, 5, or 6 consecutive 2'5' nucleotides at the 3' penultimate or 3' terminal positions; and one or more pyrimidine ribonucleotides are 2' sugar modified in the sense strand, the antisense strand or both the sense strand and the antisense strand.

In some embodiments of Structure (A2) (N)y includes at least one unconventional moiety selected from a mirror nucleotide, a 2'5' linked ribonucleotide and a TNA. In some embodiments the unconventional moiety is a mirror nucleotide. In various embodiments the mirror nucleotide is selected from an L-ribonucleotide (L-RNA) and an L-deoxyribonucleotide (L-DNA). In preferred embodiments the mirror nucleotide is L-DNA. In certain embodiments the sense strand comprises an unconventional moiety in position 9 or 10 (from the 5' terminus). In preferred embodiments the sense strand includes an unconventional moiety in position 9 (from the 5' terminus). In some embodiments the sense strand is 19 nucleotides in length and comprises 4, 5, or 6 consecutive unconventional moieties in positions 15 (from the 5' terminus). In some embodiments the sense strand includes 4 consecutive 2'5' ribonucleotides in positions 15, 16, 17, and 18. In some embodiments the sense strand includes 5 consecutive 2'5' ribonucleotides in positions 15, 16, 17, 18 and 19. In various embodiments the sense strand further comprises Z'. In some embodiments Z' includes a C3OH moiety or a C3Pi moiety.

In some embodiments of Structure (A2) (N)y comprises at least one unconventional moiety selected from a mirror nucleotide and a nucleotide joined to an adjacent nucleotide by a 2'-5' internucleotide phosphate bond (2'5' linked). In some embodiments the unconventional moiety is a mirror nucleotide. In various embodiments the mirror nucleotide is selected from an L-ribonucleotide (L-RNA) and an L-deoxyribonucleotide (L-DNA). In preferred embodiments the mirror nucleotide is L-DNA.

In some embodiments of Structure (A2), (N)y comprises at least one L-DNA moiety. In some embodiments x=y=18 and $N^2$—(N')y, consists of unmodified ribonucleotides at positions 1-17 and 19 and one L-DNA at the 3' penultimate position (position 18). In other embodiments x=y=18 and $N^2$—(N')y consists of unmodified ribonucleotides at position 1-16 and 19 and two consecutive L-DNA at the 3' penultimate position (positions 17 and 18). In various embodiments the unconventional moiety is a nucleotide joined to an adjacent nucleotide by a 2'-5' internucleotide phosphate linkage. According to various embodiments $N^2$—(N')y comprises 2, 3, 4, 5, or 6 consecutive ribonucleotides at the 3' terminus linked by 2'-5' internucleotide linkages. In one embodiment, four consecutive ribonucleotides at the 3' terminus of $N^2$—(N')y are joined by three 2'-5' phosphodiester bonds, wherein one or more of the 2'-5' ribonucleotides which form the 2'-5' phosphodiester bonds further comprises a 3'-O-methyl (3'OMe) sugar modification. In some embodiments the 3' terminal ribonucleotide of $N^2$—(N')y comprises a 2'OMe sugar modification. In certain embodiments x=y=18 and $N^2$—(N')y comprises two or more consecutive nucleotides at positions 15, 16, 17, 18 and 19 joined to an adjacent nucleotide by a 2'-5' internucleotide bond. In various embodiments the nucleotide forming the 2'-5' internucleotide bond comprises a 3' deoxyribose nucleotide or a 3' methoxy nucleotide. In various embodiments, the ribonucleotide forming the 2'-5' internucleotide bond comprises a 3' deoxyribose ribonucleotide or a 3' methoxy ribonucleotide. In some embodiments x=y=18 and $N^2$—(N')y comprises nucleotides joined to the adjacent nucleotide by a 2'-5' internucleotide bond between positions 16-17 and 17-18 or between positions 17-18 and 18-19 or between positions 15-16 and 17-18. In various embodiments, the nucleotides forming the 2'-5' internucleotide bond comprise ribonucleotides. In various embodiments, the nucleotides forming the 2'-5' internucleotide bond are ribonucleotides. In other embodiments a pyrimidine ribonucleotide (rU, rC) in (N')y comprises a ribonucleotide joined to the adjacent ribonucleotide by a 2'-5' internucleotide bond.

In further embodiments of Structure (A2) (N')y comprises 1-8 modified ribonucleotides wherein the modified ribonucleotide is a deoxyribose (DNA) nucleotide. In certain embodiments (N')y comprises 1, 2, 3, 4, 5, 6, 7, or up to 8 DNA moieties.

In some embodiments the antisense and sense strands comprise the oligonucleotide pairs identified herein as DDIT4_41 (SEQ ID NOS:3 and 12), DDIT4_43 (SEQ ID NOS:4 and 14), DDIT4_46 (SEQ ID NOS:5 and 14), DDIT4_55 (SEQ ID NOS:6 and 15), DDIT4_59 (SEQ ID NOS:7 and 16), DDIT4_60 (SEQ ID NOS:8 and 17), DDIT4_61 (SEQ ID NOS:9 and 18), DDIT4_62 (SEQ ID NOS:10 and 19), and DDIT4_63 (SEQ ID NOS:11 and 20). Preferably, the antisense and sense strands comprise the oligonucleotide pairs identified herein as DDIT4_41 (SEQ ID NOS:3 and 12) or DDIT4_63 (SEQ ID NOS:11 and 20).

Certain preferred chemically modified duplexes are set forth herein below in Table In a second aspect provided are compositions comprising one or more such nucleic acid compounds disclosed herein; and a pharmaceutically acceptable carrier or excipient. In some embodiments the dsRNA molecule is administered as naked dsRNA. In other embodiments the dsRNA molecule is admixed with a pharmaceutically acceptable carrier. In yet other embodiments the dsRNA is encapsulated in a drug carrier.

In a third aspect provided is use of the molecules disclosed herein in treating a subject suffering from disease or disorder associated with DDIT4 expression. Such methods involve administering to a mammal in need of such treatment a prophylactically or therapeutically effective amount of one or more such molecules, which inhibit or reduce expression or activity of DDIT4.

In another aspect provided are methods for treating, including preventing, the incidence or severity of a disease or disorder in which the expression of DDIT4 is associated with the etiology or progression of said disease or disorder.

In one embodiment, provided are methods for treating, including preventing, the incidence or severity of hearing loss in which expression of the DDIT4 is associated with the etiology or progression of the hearing disorder/hearing loss.

In another embodiment, provided are methods for treating, including preventing, the incidence or severity of a respiratory disorder which expression of the DDIT4 is associated with the etiology or progression of the respiratory disorder.

In another embodiment, provided are methods for treating, including preventing, the incidence or severity of eye diseases and conditions in which expression of the DDIT4 is associated with the etiology or progression of the eye diseases and conditions.

In yet another embodiment, provided are methods for treating, including preventing, the incidence or severity of a neurodegenerative disorder which expression of the DDIT4 is associated with the etiology or progression of the neurodegenerative disorder.

In one embodiment, provided are methods for treating, including preventing, the incidence or severity of muscle atrophy or skin atrophy which expression of the DDIT4 is associated with the etiology or progression of the skin atrophy or muscle atrophy.

In another embodiment, provided are methods for providing neuroprotection to a neuron, in which expression of the DDIT4 is associated with neuron death or degeneration.

Further provided herein is method of treating a disease or disorder in a subject whereby expression of the DDIT4 gene is associated with the etiology or progression of the disease or disorder, comprising administering to the subject a therapeutically effective amount of molecule or composition disclosed herein, thereby treating the disease or disorder in the subject.

Further provided is a method of down-regulating the expression of a DDIT4 in a cell, comprising introducing into the cell the molecule or composition disclosed herein in an amount effective to down-regulate expression of DDIT4. In some embodiments, the cell is a skin cell, a kidney cell or an eye cell.

Additionally provided is a method of providing neuroprotection to a neuron, comprising introducing into the neuron a molecule or composition disclosed herein in an amount effective to down-regulate expression of DDIT4. In some embodiments, the neuron is an optic nerve cell or a retinal ganglion cell.

The preferred methods, materials, and examples that will now be described are illustrative only and are not intended to be limiting; materials and methods similar or equivalent to those described herein can be used in practice or testing the embodiments of the disclosure. Other features and advantages will be apparent from the following figures, detailed description, and from the claims.

BRIEF DESCRIPTION OF THE FIGURES

FIG. 1A shows that DDIT4_41a_S2012 and _S2013 exhibit better knockdown activity than the DDIT2 molecule in 293 cells at all concentrations. FIG. 1B shows that DDIT4_41a_S2012 and _S2013 exhibit better knockdown activity than the DDIT4_2 molecule at clinically relevant concentrations between 3.7 nM-0.045 nM in B22C cells. FIG. 1C shows that DDIT4_63u activity compared to the DDIT4_2 molecule in Be2C cells. FIGS. 1D and 1E show that DDIT4_41a activity compared to the DDIT4_2 molecule in Be2C cells. FIG. 1F shows that DDIT4_41_S2071 exhibits better knockdown activity than the DDIT4_1 molecule in Be2C cells at all concentrations.

FIG. 3A shows stability of DDIT4_41a_S2012 and 52013 in human plasma (h-plasma) and rabbit vitreous fluid (Rab vitreous) at 3 hr., 8 hr. and 24 hr. compared to control ("box"), FIG. 3B shows Stability of DDIT4_41a_S2071 and _S2072 in human plasma (h-plasma) and rabbit vitreous fluid (Rab vitreous) at 3 hr., 8 hr. and 24 hr. compared to control ("box"). FIG. 3C shows stability of DDIT4_41a_S2073 in human plasma (h-plasma) and rabbit vitreous fluid (Rab vitreous) at 3 hr., 8 hr. and 24 hr. compared to control ("box"). FIG. 3D shows stability of DDIT4_41a_S2071 sense strand in HCT116 cytosolic extract at 3 hr., 8 hr. and 24 hr. compared to control ("box").

FIG. 4A shows on target activity of antisense strand and FIG. 4B shows off-target activity of sense strand (Psi-CHECK). The difference between the three molecules is in the capping moiety on the sense strand. _S2071 includes an inverted deoxyabasic capping moiety, _S2072 includes an amino C6 moiety and _S2073 includes a THNB moiety. 12 and 13 refer to DDIT4_41a_S2012 and S2013, respectively

DETAILED DESCRIPTION OF THE INVENTION

Figure 1A:
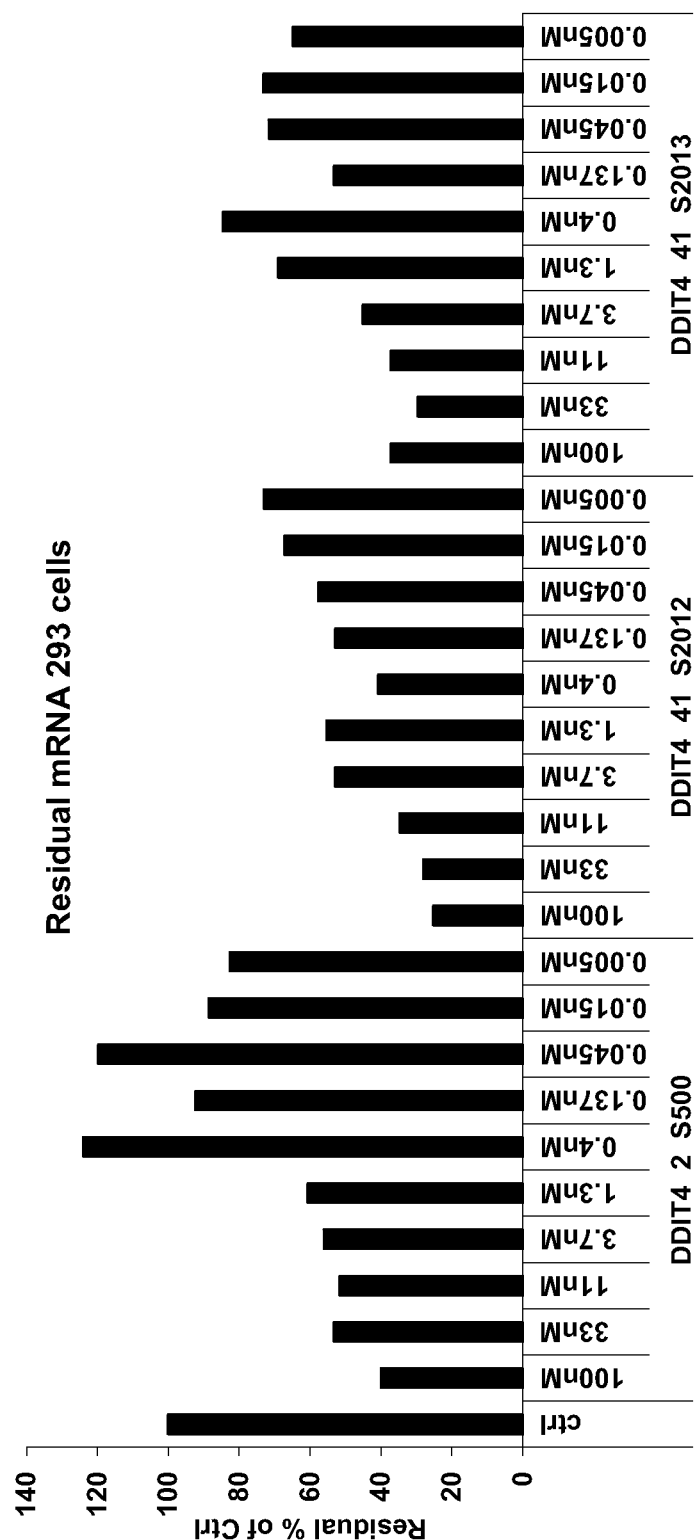
FIGS. 1A-1F show on-target knock down activity (% residual mRNA) of DDI4_41a and DDIT4_63u chemically modified dsRNA molecules compared to DDIT4_2 dsRNA molecules in 293 (1A) and Be2C (1B-1E) cells. The X axis in FIGS. 1A and 1B shows decreasing concentration of the dsRNA molecules, from right to left 100 nM, 33 nM, 11 nM, 3.7 nM, 1,3 nM, 0.4 nM, 0.137 nM, 0.045 nM, 0.015 nM and in some 0.005 nM. The X-axis in FIGS. 1C, 1D and 1E show decreasing concentration of dsRNA molecules at 20 nM, 5 nM and 0.5 nM.
Figure 1B:
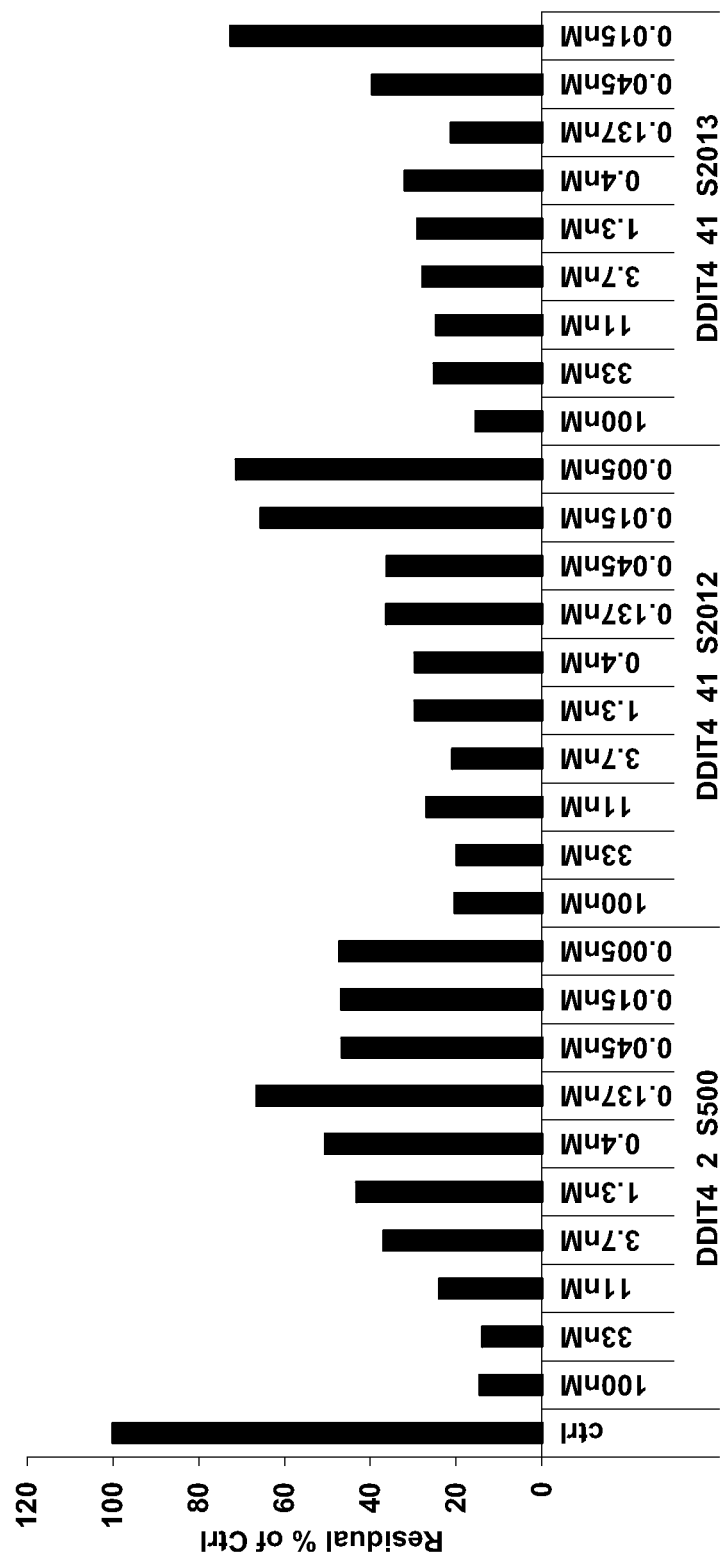
Figure 1C:
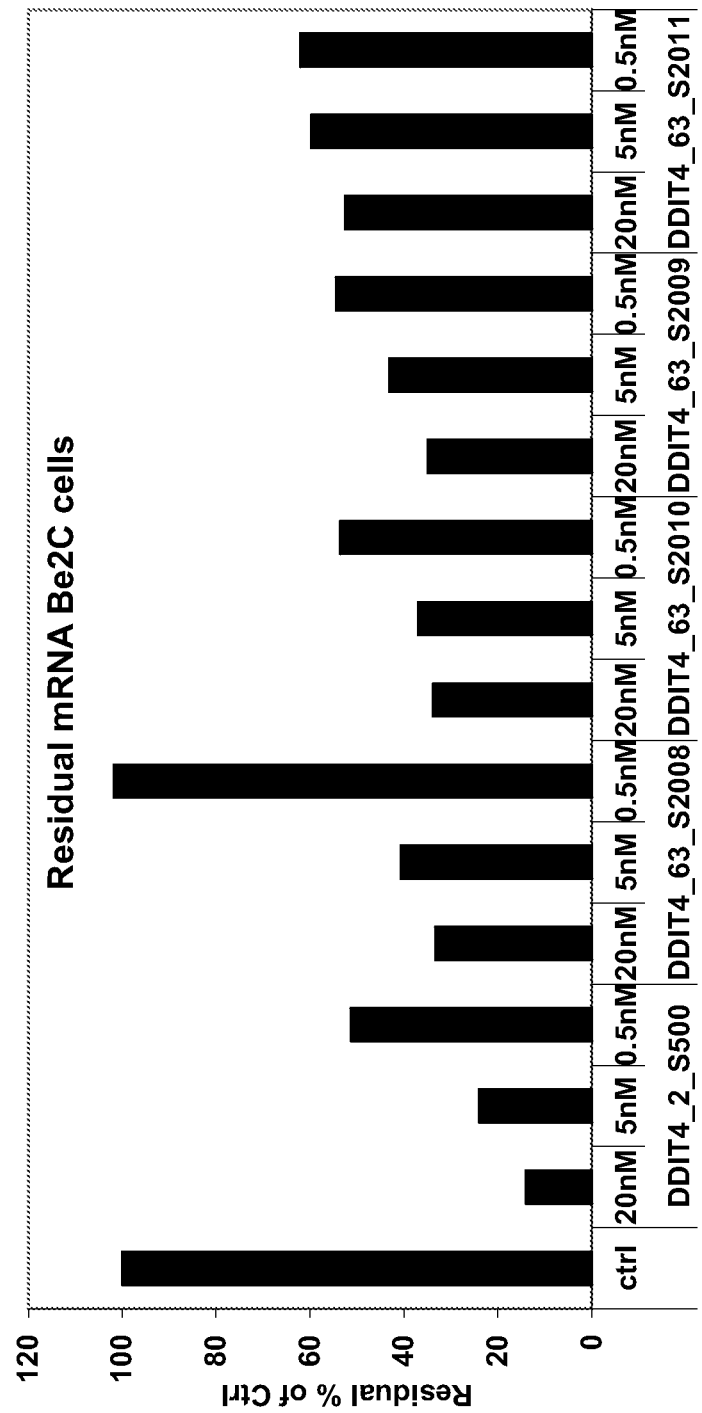
Figure 1D:
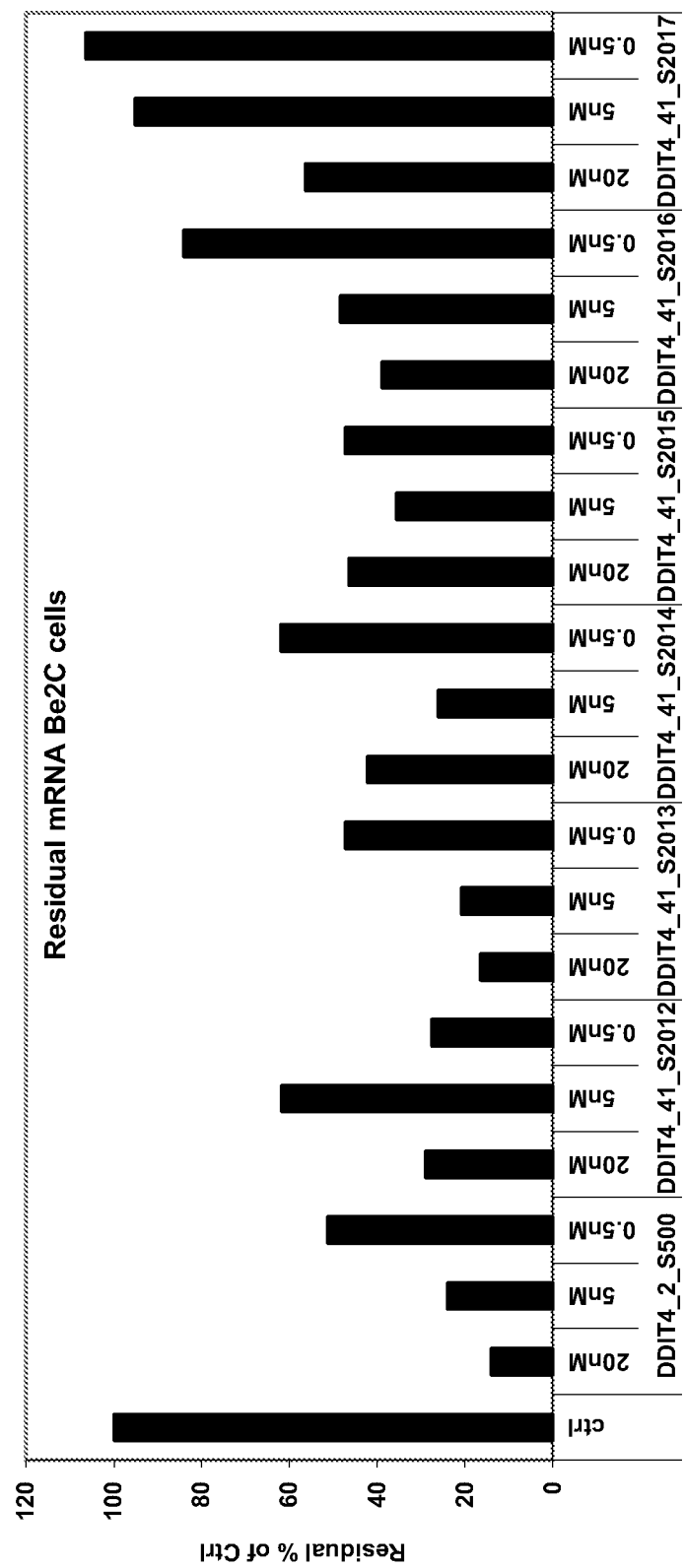
Figure 1E:
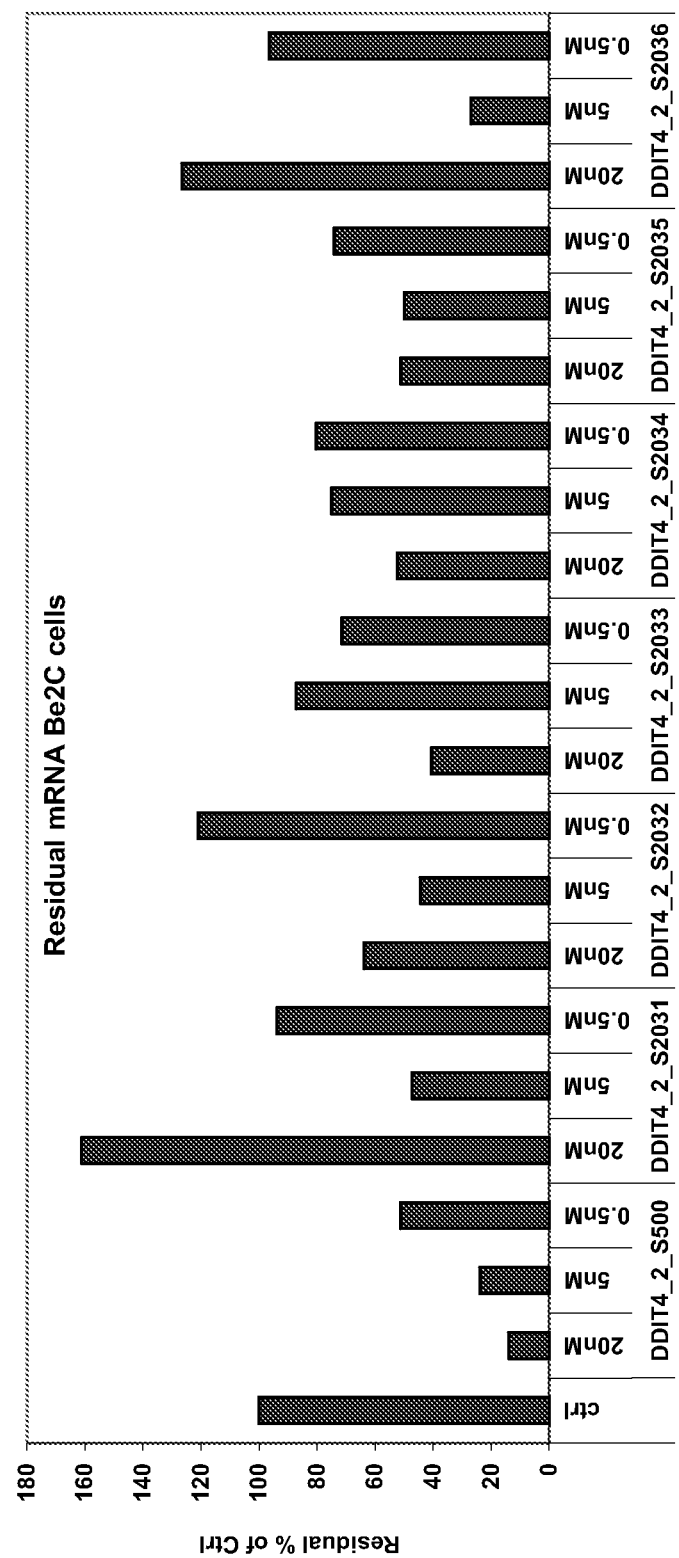
Figure 1F:
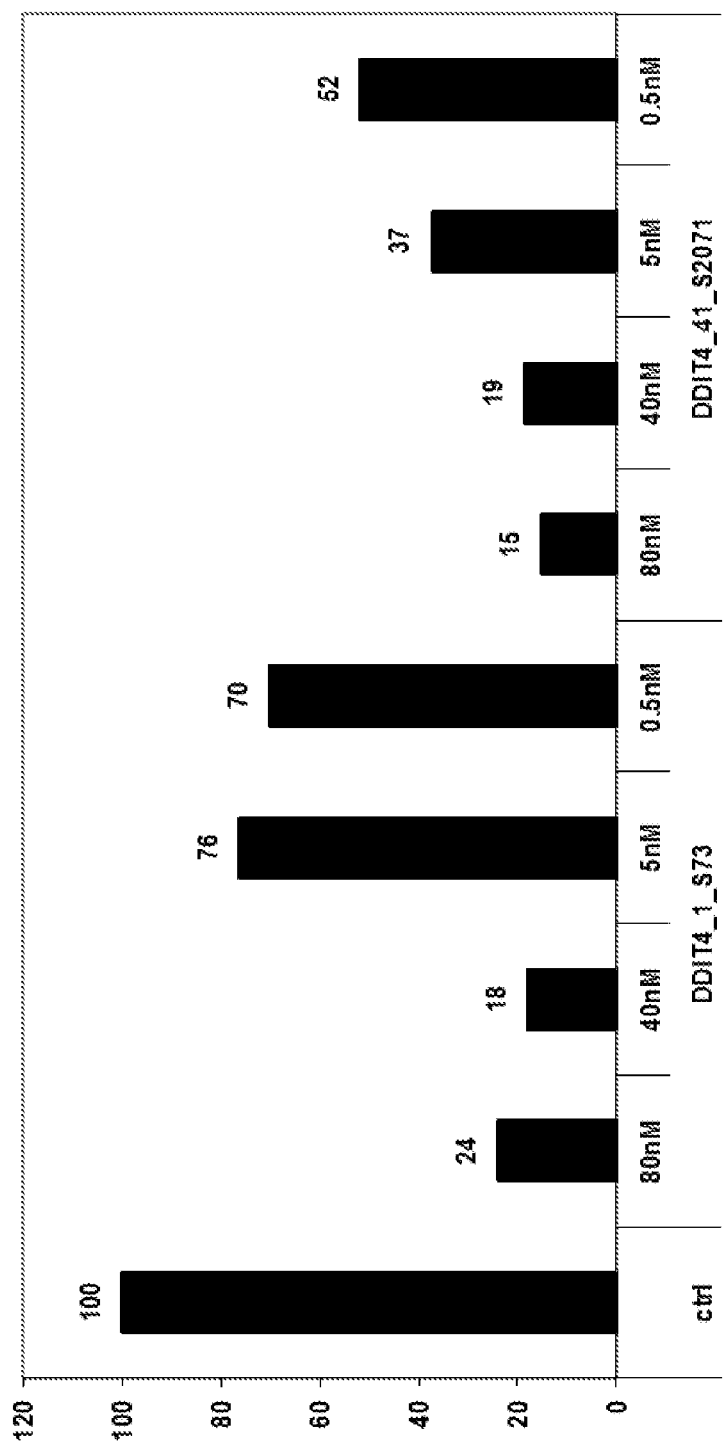

Provided herein are double stranded nucleic acid molecules that target DDIT4, compositions comprising those molecules their use in treating a subject suffering from diseases and disorders. Inhibition of DDIT4 expression was shown to be beneficial in the treatment of many diseases and disorders in which DDIT4 expression is associated with the etiology or progression of the disease or disorder.

Provided herein are dsRNA molecules, methods and compositions for inhibiting expression of a target DDIT4 gene in vitro and in vivo. In general, the methods include administering oligoribonucleotides, such as dsRNA molecules including small interfering RNAs (i.e., dsRNAs) that target DDIT4 and hybridize to, or interact with, the mRNA under biological conditions (within the cell), or a nucleic acid material that can produce siRNA in a cell, in an amount sufficient to down-regulate expression of DDIT4 expression. Without wishing to be bound to theory, the down regulation may be regulated by an RNA interference mechanism.

The dsRNAs disclosed herein possess structures and modifications which may, for example increase activity, increase stability, and or minimize toxicity; the chemically modified dsRNAs molecules disclosed herein are useful in preventing or attenuating target gene expression, in particular the target genes discussed herein.

In some embodiments the double stranded nucleic acid molecules comprise a DNA moiety or a mismatch to the target at position 1 of the antisense strand (5' terminus). Such a duplex structure is described herein. According to one embodiment provided are double stranded dsRNA molecules having a structure (A2) set forth below:

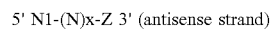

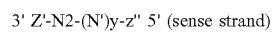
(A2)

wherein each N1, N2, N and N' is independently an unmodified or modified nucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 39;

wherein N2 is covalently bound to (N')y;

wherein N1 is covalently bound to (N)x and is mismatched to the target mRNA (SEQ ID NO:1-11) or is a complementary DNA moiety to the target mRNA;

wherein N1 is a moiety selected from the group consisting of natural or modified: uridine, deoxyribouridine, ribothymidine, deoxyribothymidine, adenosine or deoxyadenosine;

wherein z" may be present or absent, but if present is a capping moiety or a conjugate moiety covalently attached at the 5' terminus of N2-(N')y;

wherein each of Z and Z' is independently present or absent, but if present is independently 1-5 consecutive nucleotides, consecutive non-nucleotide moieties, consecutive unconventional moieties or a combination thereof or a conjugate moiety covalently attached at the 3' terminus of the strand in which it is present; and wherein the sequence of (N')y is complementary to the sequence of (N)x; and wherein the sequence of (N)x comprises an antisense sequence and (N')y comprises a sense sequence set forth in SEQ ID NOS:3 and 12; SEQ ID NOS:4 and 13; SEQ ID NOS:5 and 14; SEQ ID NOS:6 and 15; SEQ ID NOS:7 and 16; SEQ ID NOS:8 and 17; SEQ ID NOS:9 and 18; SEQ ID NOS:10 and 19; or SEQ ID NOS:11 and 20. In preferred embodiments the sense strand and antisense strand comprise sequence pairs set forth in any of SEQ ID NOS:21 and 30; SEQ ID NOS:22 and 31; SEQ ID NOS:23 and 32; SEQ ID NOS:24 and 33; SEQ ID NOS:25 and 34; SEQ ID NOS:26 and 35; SEQ ID NOS:27 and 36; SEQ ID NOS:28 and 37; or SEQ ID NOS:29 and 38.

Definitions

For convenience certain terms employed in the specification, examples and claims are described herein.

It is to be noted that, as used herein, the singular forms "a", "an" and "the" include plural forms unless the content clearly dictates otherwise.

Where aspects or embodiments of the invention are described in terms of Markush groups or other grouping of alternatives, those skilled in the art will recognize that the invention is also thereby described in terms of any individual member or subgroup of members of the group.

An "inhibitor" is a compound, which is capable of reducing (partially or fully) the expression of a gene or the activity of the product of such gene to an extent sufficient to achieve a desired biological or physiological effect. The term "inhibitor" as used herein refers to one or more of an oligonucleotide inhibitor, including siRNA, shRNA, synthetic shRNA; miRNA, ssRNA, antisense RNA and DNA and ribozymes.

A "dsRNA molecule" or "dsRNA inhibitor" is a compound which is capable of down-regulating or reducing the expression of a gene or the activity of the product of such gene to an extent sufficient to achieve a desired biological or physiological effect and includes one or more of a siRNA, shRNA, synthetic shRNA; miRNA. Inhibition may also be referred to as down-regulation or, for RNAi, silencing.

The term "inhibit" as used herein refers to reducing the expression of a gene or the activity of the product of such gene to an extent sufficient to achieve a desired biological or physiological effect. Inhibition is either complete or partial.

As used herein, the term "inhibition" of a target gene means inhibition of the gene expression (transcription or translation) or polypeptide activity of the DDIT4 gene wherein or an SNP (single nucleotide polymorphism) or other variants thereof. The terms "mRNA polynucleotide sequence", "mRNA sequence" and "mRNA" are used interchangeably.

As used herein, the terms "polynucleotide" and "nucleic acid" may be used interchangeably and refer to nucleotide sequences comprising deoxyribonucleic acid (DNA), and ribonucleic acid (RNA). The terms are to be understood to include, as equivalents, analogs of either RNA or DNA made from nucleotide analogs. Throughout this application, mRNA sequences are set forth as representing the corresponding genes.

"Oligonucleotide" or "oligomer" refers to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The compounds of the present invention encompass molecules comprising deoxyribonucleotides, ribonucleotides, modified deoxyribonucleotides, modified ribonucleotides and combinations thereof "Substantially complementary" refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

"Nucleotide" is meant to encompass deoxyribonucleotides and ribonucleotides, which may be natural or synthetic, and or modified or unmodified. Modifications include changes to the sugar moiety, the base moiety and or the linkages between ribonucleotides in the oligoribonucleotide. As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide.

The nucleotides can be selected from naturally occurring or synthetic modified bases. Naturally occurring bases include adenine, guanine, cytosine, thymine and uracil. Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil, pyrazolotriazine base nucleic acid analogs, and 5-trifluoro cytosine. In some embodiments one or more nucleotides in an oligomer is substituted with inosine.

According to some embodiments the present invention provides inhibitory oligonucleotide compounds comprising unmodified and modified nucleotides and or unconventional moieties. The compound comprises at least one modified nucleotide selected from the group consisting of a sugar modification, a base modification and an internucleotide linkage modification and may contain DNA, and modified nucleotides such as LNA (locked nucleic acid), ENA (ethylene-bridged nucleic acid), PNA (peptide nucleic acid), arabinoside, phosphonocarboxylate or phosphinocarboxylate nucleotide (PACE nucleotide), mirror nucleotide, or nucleotides with a 6 carbon sugar.

All analogs of, or modifications to, a nucleotide/oligonucleotide are employed with the present invention, provided that said analog or modification does not substantially adversely affect the function of the nucleotide/oligonucleotide. Acceptable modifications include modifications of the sugar moiety, modifications of the base moiety, modifications in the internucleotide linkages and combinations thereof.

A sugar modification includes a modification on the 2' moiety of the sugar residue and encompasses amino, fluoro, alkoxy e.g. methoxy, alkyl, amino, fluoro, chloro, bromo, CN, CF, imidazole, carboxylate, thioate, $C_1$ to $C_{10}$ lower alkyl, substituted lower alkyl, alkaryl or aralkyl, $OCF_3$, OCN, O—, S—, or N-alkyl; O—, S, or N-alkenyl; $SOCH_3$; $SO_2CH_3$; $ONO_2$; $NO_2$, $N_3$; heterozycloalkyl; heterozycloalkaryl; aminoalkylamino; polyalkylamino or substituted silyl, as, among others, described in European patents EP 0 586 520 B1 or EP 0 618 925 B1.

In one embodiment the dsRNA molecule comprises at least one ribonucleotide comprising a 2' modification on the sugar moiety ("2' sugar modification"). In certain embodiments the compound comprises 2'O-alkyl or 2'-fluoro or 2'O-allyl or any other 2' modification, optionally on alternate positions. Other stabilizing modifications are also possible (e.g. terminal modifications). In some embodiments a preferred 2'O-alkyl is 2'O-methyl (methoxy) sugar modification.

[1] In some embodiments the backbone of the oligonucleotides is modified and comprises phosphate-D-ribose entities but may also contain thiophosphate-D-ribose entities, triester, thioate, 2'-5' bridged backbone (also may be referred to as 5'-2'), PACE and the like. Additional internucleotide linkage modifications include reversible or labile phosphotriester linkages such as those disclosed in US20090093425 and US20110294869, respectively.

As used herein, the terms "non-pairing nucleotide analog" means a nucleotide analog which comprises a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide. In addition, analogues of polynucleotides may be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA) is replaced with a polyamide backbone which is similar to that found in peptides. PNA analogues have been shown to be resistant to enzymatic degradation and to have extended stability in vivo and in vitro. Other modifications that can be made to oligonucleotides include polymer backbones, cyclic backbones, acyclic backbones, thiophosphate-D-ribose backbones, triester backbones, thioate backbones, 2'-5' bridged backbone, artificial nucleic acids, morpholino nucleic acids, glycol nucleic acid (GNA), threose nucleic acid (TNA), arabinoside, and mirror nucleoside (for example, beta-L-deoxyribonucleoside instead of beta-D-deoxyribonucleoside). Examples of dsRNA molecules comprising LNA nucleotides are disclosed in Elmen et al., (NAR 2005, 33(1):439-447).

Preferred modifications, include incorporation of TNA moieties in the sense strand and or antisense strand. Examples of dsRNA comprising TNA moieties are disclosed in PCT/US11/063365, to the assignee of the present invention. In some embodiments, 1-19 ribonucleotides in the sense strand may be substituted with TNA.

Preferred modifications, include incorporation of pyrazolotriazine base-modified nucleotide moieties in the sense strand and or antisense strand. Examples of pyrazolotriazine moieties and dsRNA comprising pyrazolotriazine moieties are disclosed in PCT/IL2013/050465, co-assigned to the assignee of the present invention. Pyrazolotriazine DNA or RNA analogues are preferably incorporated into a 19-mer antisense strand in positions 1, 5, 6 or 7 (5'>3'). In some embodiments, pyrazolotriazine RNA analogues are preferred. Pyrazolotriazine DNA or RNA analogues may also be covalently attached to the 3' terminus of the sense strand or antisense strand, as 3' terminal overhangs.

The term "conjugate moiety" as used herein refers to a moiety including a peptide, lipid, drug, vitamin, mineral, fluorophore that is capable of being covalently attached to the nucleic acid molecule, preferably at one or more of the 5' terminus or 3' terminus. Without wishing to be bound to theory, the conjugate moiety alters the biodistribution, endosomal escape, cell uptake, plasma retention, targeting of the molecule, without adversely affecting the activity of the nucleic acid molecule. For example, a preferred vitamin is a Vitamin D, Vitamin A or Vitamin E moiety; a preferred lipid is a sphingolipid or cholesterol or cholesterol derivative.

The compounds of the present invention can be synthesized using one or more inverted nucleotides, for example inverted thymidine or inverted adenine (see, for example, Takei, et al., 2002, JBC 277(26):23800-06).

A "mirror" nucleotide is a nucleotide with reversed chirality to the naturally occurring or commonly employed nucleotide, i.e., a mirror image (L-nucleotide) of the naturally occurring (D-nucleotide), also referred to as L-RNA in the case of a mirror ribonucleotide, and "spiegelmer". The nucleotide can be a ribonucleotide or a deoxyribonucleotide and my further comprise at least one sugar, base and or backbone modification. See U.S. Pat. No. 6,586,238. Also, U.S. Pat. No. 6,602,858 discloses nucleic acid catalysts comprising at least one L-nucleotide substitution.

Other modifications include terminal modifications on the 5' and/or 3' part of the oligonucleotides and are also known as capping moieties. Such terminal modifications are selected from a nucleotide, a modified nucleotide, a lipid, a peptide, a sugar and inverted abasic moiety.

An "alkyl moiety or derivative thereof" refers to straight chain or branched carbon moieties and moieties per se or further comprising a functional group including alcohols, phosphodiester, phosphorothioate, phosphonoacetate and also includes amines, carboxylic acids, esters, amides aldehydes. "Hydrocarbon moiety" and "alkyl moiety" are used interchangeably.

"Terminal functional group" includes halogen, alcohol, amine, carboxylic, ester, amide, aldehyde, ketone, ether groups.

Provided are methods and compositions for inhibiting expression of the target gene in vivo. In general, the method includes administering oligoribonucleotides, in particular small interfering RNAs (i.e. siRNA) that target an mRNA transcribed from the target gene in an amount sufficient to down-regulate expression of a target gene by an RNA interference mechanism. In particular, the subject method can be used to inhibit expression of the target gene for treatment of a disease. Provided herein are dsRNA molecules directed to a target gene disclosed herein and useful as therapeutic agents to treat various otic and vestibular system pathologies.

Provided are methods and compositions for inhibiting expression of a hearing loss-associated gene in vivo. Without wishing to be bound to theory, the method includes administering an oligoribonucleotide, in particular a double stranded RNA (such as, for example, siRNA), that target DDIT4 mRNA, or pharmaceutical compositions comprising them, in an amount sufficient to down-regulate expression of a DDIT4 by an RNA interference mechanism. In particular, the subject method can be used to inhibit expression of DDIT4 for treatment of a disease or a disorder or a condition disclosed herein.

In some embodiments the dsRNA is blunt ended, on one or both ends. More specifically, the dsRNA may be blunt ended on the end defined by the 5'-terminus of the first strand and the 3'-terminus of the second strand, or the end defined by the 3'-terminus of the first strand and the 5'-terminus of the second strand.

In other embodiments at least one of the two strands may have an overhang of at least one nucleotide at the 5'-terminus; the overhang may consist of at least one deoxyribonucleotide. At least one of the strands may also optionally have an overhang of at least one nucleotide at the 3'-terminus. The overhang may consist of from about 1 to about 5 nucleotides.

In some embodiments, the antisense strand includes a cleavable or non-cleavable Pi. Without wishing to be bound to theory, the 5' Pi may facilitate loading of the antisense strand into the RISC complex.

In some embodiments, the sense strand includes a capping moiety or a conjugate moiety (z"). Without wishing to be bound to theory, z" may hinder loading of the sense strand into the RISC complex, and/or may facilitate cellular uptake and endosomal escape.

The length of RNA duplex is from about 18 to about 40 ribonucleotides, preferably 19 to 23 ribonucleotides. Further, the length of each strand (oligomer) may independently have a length selected from the group consisting of about 18 to about 40 bases, preferably 18 to 23 bases and more preferably 19, 20 or 21 ribonucleotides.

Additionally, in certain preferred embodiments the complementarity between said first strand and the target nucleic acid is perfect. In some embodiments, the strands are substantially complementary, i.e. having one, two or up to three mismatches between said first strand and the target nucleic acid.

Further, the 5'-terminus of the first strand of the siRNA may be linked to the 3'-terminus of the second strand, or the 3'-terminus of the first strand may be linked to the 5'-terminus of the second strand, said linkage being via a nucleic acid linker typically having a length between 3-100 nucleotides, preferably about 3 to about 10 nucleotides.

The dsRNA molecules disclosed herein possess structures and modifications which impart one or more of increased activity, increased stability, reduced toxicity, reduced off target effect, and/or reduced immune response. The siRNA structures of the present invention are beneficially applied to double stranded RNA useful in preventing or attenuation target gene expression, in particular the target genes discussed herein.

According to one aspect the present invention provides a chemically modified double stranded oligonucleotide comprising at least one modified nucleotide selected from the group consisting of a sugar modification, a base modification and an internucleotide linkage modification. Accordingly, the chemically modified double stranded oligonucleotide compounds of the invention may contain modified nucleotides such as DNA, LNA (locked nucleic acid), ENA (ethylene-bridged nucleic acid), PNA (peptide nucleic acid), arabinoside, PACE, mirror nucleoside, or nucleotides with a 6 carbon sugar. Examples of PACE nucleotides and analogs are disclosed in U.S. Pat. Nos. 6,693,187 and 7,067,641 both incorporated herein by reference. The oligonucleotide may further comprise 2'O-methyl or 2'-fluoro or 2'O-allyl or any other 2' modification, optionally on alternate positions. Other stabilizing modifications, which do not significantly reduce the activity are also possible (e.g. terminal modifications). The backbone of the active part of the oligonucleotides may comprise phosphate-D-ribose entities but may also contain thiophosphate-D-ribose entities, triester, thioate, 2'-5' bridged backbone (also may be referred to as 5'-2'), PACE or any other type of modification. Terminal modifications on the 5' and/or 3' part of the oligonucleotides are also possible. Such terminal modifications may be lipids, peptides, sugars, inverted abasic moieties or other molecules.

The present invention also relates to compounds which down-regulate expression of the genes disclosed herein, particularly to novel ds RNAs, and to the use of these novel dsRNAs in the treatment of various diseases and medical conditions. Particular diseases and conditions to be treated are related to hearing loss or disorders disclosed herein. Lists of siRNA to be used in the present invention are provided in Tables 2A-10D. 21- or 23-mer siRNA sequences can also be generated by 5' and/or 3' extension of the 19-mer sequences disclosed herein. Such extension is preferably complementary to the corresponding mRNA sequence. The dsRNAs of the present invention possess structures and modifications which may increase activity, increase stability, reduce off-target effect, reduce immune response and/or reduce toxicity. The dsRNA structures of the present invention are beneficially applied to double stranded RNA useful in preventing or attenuating expression of one or more of the target genes disclosed herein.

Methods, molecules and compositions of the present invention which inhibit the genes disclosed herein are discussed herein at length, and any of said molecules and/or compositions are beneficially employed in the treatment of a subject suffering from one or more of said conditions.

Where aspects or embodiments of the invention are described in terms of Markush groups or other grouping of alternatives, those skilled in the art will recognize that the invention is also thereby described in terms of any individual member or subgroup of members of the group.

dsRNA and RNA Interference

RNA interference (RNAi) is a phenomenon involving double-stranded (ds) RNA-dependent gene-specific post-transcriptional silencing. Initial attempts to study this phenomenon and to manipulate mammalian cells experimentally were frustrated by an active, non-specific antiviral defense mechanism which was activated in response to long dsRNA molecules (Gil et al., Apoptosis, 2000. 5:107-114). Later, it was discovered that synthetic duplexes of 21 nucleotide RNAs could mediate gene specific RNAi in mammalian cells, without stimulating the generic antiviral defense mechanisms Elbashir et al. Nature 2001, 411:494-498 and Caplen et al. PNAS 2001, 98:9742-9747). As a result, small interfering RNAs (siRNAs), which are short double-stranded RNAs, have been widely used to inhibit gene expression and understand gene function.

RNA interference (RNAi) is mediated by small interfering RNAs (siRNAs) (Fire et al, Nature 1998, 391:806) or microRNAs (miRNAs) (Ambros V. Nature 2004, 431:350-355); and Bartel D P. Cell. 2004 116(2):281-97). The corresponding process is commonly referred to as specific post-transcriptional gene silencing when observed in plants and as quelling when observed in fungi.

A siRNA compound is a double-stranded RNA which down-regulates or silences (i.e. fully or partially inhibits) the expression of an endogenous or exogenous gene/mRNA. RNA interference is based on the ability of certain dsRNA species to enter a specific protein complex, where they are then targeted to complementary cellular RNAs and specifically degrades them. Thus, the RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir, et al., Genes Dev., 2001, 15:188). In more detail, longer dsRNAs are digested into short (17-29 bp) dsRNA fragments (also referred to as short inhibitory RNAs or "siRNAs") by type III RNAses (DICER, DROSHA, etc., (see Bernstein et al., Nature, 2001, 409:363-6 and Lee et al., Nature, 2003, 425:415-9). The RISC protein complex recognizes these fragments and complementary mRNA. The whole process is culminated by endonuclease cleavage of target mRNA (McManus and Sharp, Nature Rev Genet, 2002, 3:737-47; Paddison and Hannon, Curr Opin Mol Ther. 2003, 5(3): 217-24). (For additional information on these terms and proposed mechanisms, see for example, Bernstein, et al., RNA. 2001, 7(11):1509-21; Nishikura, Cell. 2001, 107(4): 415-8 and PCT Publication No. WO 01/36646).

The selection and synthesis of dsRNA compounds corresponding to known genes has been widely reported; see for example Ui-Tei et al., J Biomed Biotechnol. 2006; 65052; Chalk et al., BBRC. 2004, 319(1):264-74; Sioud and Leirdal, Met. Mol Biol.; 2004, 252:457-69; Levenkova et al., Bioinform. 2004, 20(3):430-2; Ui-Tei et al., NAR 2004, 32(3):936-48. For examples of the use of, and production of, modified siRNA see Braasch et al., Biochem., 2003, 42(26): 7967-75; Chiu et al., RNA, 2003, 9(9):1034-48; PCT publications WO 2004/015107 (atugen); WO 02/44321 (Tuschl et al), and U.S. Pat. Nos. 5,898,031 and 6,107,094.

Several groups have described the development of DNA-based vectors capable of generating siRNA within cells. The method generally involves transcription of short hairpin RNAs that are efficiently processed to form siRNAs within cells (Paddison et al. PNAS USA 2002, 99:1443-1448; Paddison et al. Genes & Dev 2002, 16:948-958; Sui et al. PNAS USA 2002, 8:5515-5520; and Brummelkamp et al. Science 2002, 296:550-553). These reports describe methods of generating siRNAs capable of specifically targeting numerous endogenously and exogenously expressed genes.

Studies have revealed that siRNA can be effective in vivo in both mammals and humans. Specifically, Bitko et al., showed that specific siRNAs directed against the respiratory syncytial virus (RSV) nucleocapsid N gene are effective in treating mice when administered intranasally (Nat. Med. 2005, 11(1):50-55). For reviews of therapeutic applications of siRNAs see for example Batik (Mol. Med 2005, 83: 764-773) and Chakraborty (Current Drug Targets 2007 8(3):469-82). outbind://115-0000000E878E010F D307C4FBC345FE996B481C10700C64E741AC0385F45-854C0862DD9778BA000000001C650000C64E741AC03-85F45854C0862DD9778BA0000002537F70000/exchweb/bin/redir.asp?URL=http://www.ncbi.nlm.nih.gov/entrez/utils/fref.fegi?itool=Abstra %20 In addition, clinical studies with short siRNAs that target the VEGFR1 receptor in order to treat age-related macular degeneration (AMD) have been conducted in human patients (Kaiser, Am J Ophthalmol. 2006 142(4):660-8). Further information on the use of siRNA as therapeutic agents may be found in Durcan, 2008. Mol. Pharma. 5(4):559-566; Kim and Rossi, 2008. BioTechniques 44:613-616; Grimm and Kay, 2007, JCI, 117(12): 3633-41.

Chemical Synthesis

The compounds of the present invention can be synthesized by any of the methods that are well-known in the art for synthesis of ribonucleic (or deoxyribonucleic) oligonucleotides. Such synthesis is, among others, described in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Annu Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et. al., in IRL Press 1989 edited by Oliver R. W. A.; Kap. 7: 183-208.

Other synthetic procedures are known in the art e.g. the procedures as described in Usman et al., 1987, J. Am. Chem. Soc., 109, 7845; Scaringe et al., 1990, NAR., 18, 5433; Wincott et al., 1995, NAR. 23, 2677-2684; and Wincott et al., 1997, Methods Mol. Bio., 74, 59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides disclosed herein can be synthesized separately and joined together post-synthetically, for example, by ligation (Moore et al., 1992, Science 256, 9923; Draper et al., International Patent Publication No. WO 93/23569; Shabarova et al., 1991, NAR 19, 4247; Bellon et al., 1997, Nucleosides & Nucleotides, 16, 951; Bellon et al., 1997, Bioconjugate Chem. 8, 204), or by hybridization following synthesis and/or deprotection.

It is noted that a commercially available machine (available, inter alia, from Applied Biosystems) can be used; the oligonucleotides are prepared according to the sequences disclosed herein. Overlapping pairs of chemically synthesized fragments can be ligated using methods well known in the art (e.g., see U.S. Pat. No. 6,121,426). The strands are synthesized separately and then are annealed to each other in the tube. Then, the double-stranded molecules are separated from the single-stranded oligonucleotides that were not annealed (e.g. because of the excess of one of them) by HPLC. In relation to the dsRNA or siRNA fragments disclosed herein, two or more such sequences can be synthesized and linked together for use in the present invention.

The molecules can also be synthesized via tandem synthesis methodology, as described for example in US Patent Publication No. US 2004/0019001 (McSwiggen), wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

The present invention further provides for a pharmaceutical composition comprising two or more siRNA molecules for the treatment of any of the diseases and conditions mentioned herein, whereby said two molecules may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. In one embodiment, the siRNA molecules are comprised of a double-stranded nucleic acid structure as described herein, wherein the two dsRNA molecules are selected from the oligonucleotides described herein. Thus, the siRNA molecules may be covalently or non-covalently bound or joined by a linker to form a tandem siRNA compound. Such tandem dsRNA molecules comprising two siRNA sequences are typically of 38-150 nucleotides in length, more preferably 38 or 40-60 nucleotides in length, and longer accordingly if more than two siRNA sequences are included in the tandem molecule. A longer tandem compound comprised of two or more longer sequences which encode siRNA produced via internal cellular processing, e.g., long dsRNAs, is also envisaged, as is a tandem molecule encoding two or more shRNA. Such tandem molecules are also considered to be a part of the disclosure. A compound comprising two (tandem) or more (RNAistar) dsRNA sequences disclosed herein is envisaged. Examples of such "tandem" or "star" molecules are provided in PCT patent publication no. WO 2007/091269, assigned to the assignee of the present application and incorporated herein by reference in its entirety.

The dsRNA molecules that target DDIT4 may be the main active component in a pharmaceutical composition, or may be one active component of a pharmaceutical composition containing two or more dsRNAs (or molecules which encode or endogenously produce two or more dsRNAs, be it a mixture of molecules or one or more tandem molecules which encode two or more dsRNAs), said pharmaceutical composition further being comprised of one or more additional dsRNA molecule which targets one or more additional gene. Simultaneous inhibition of said additional gene(s) will likely have an additive or synergistic effect for treatment of the diseases disclosed herein.

Additionally, the dsRNA disclosed herein or any nucleic acid molecule comprising or encoding such dsRNA can be linked or bound (covalently or non-covalently) to antibodies (including aptamer molecules) against cell surface internalizable molecules expressed on the target cells, in order to achieve enhanced targeting for treatment of the diseases disclosed herein. For example, anti-Fas antibody (preferably a neutralizing antibody) may be combined (covalently or non-covalently) with any dsRNA. In another example, an aptamer which can act like a ligand/antibody may be combined (covalently or non-covalently) with any dsRNA.

The nucleic acid molecules disclosed herein can be delivered either directly or with viral or non-viral vectors. When delivered directly, the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell. Vectors optionally used for delivery of the compounds of the present invention are commercially available, and may be modified for the purpose of delivery of the compounds of the present invention by methods known to one of skill in the art.

Chemical Modifications

All analogs of, or modifications to, a nucleotide/oligonucleotide may be employed with the present invention, provided that said analogue or modification does not substantially affect the function of the nucleotide/oligonucleotide. The nucleotides can be selected from naturally occurring or synthetic modified bases. Naturally occurring bases include adenine, guanine, cytosine, thymine and uracil. Modified bases of nucleotides are described herein.

In addition, analogues of polynucleotides can be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to enzymatic degradation and to have extended stability in vivo and in vitro. Other modifications that can be made to oligonucleotides include polymer backbones, cyclic backbones, acyclic backbones, thiophosphate-D-ribose backbones, triester backbones, thioate backbones, 2'-5' bridged backbone, artificial nucleic acids, morpholino nucleic acids, locked nucleic acid (LNA), glycol nucleic acid (GNA), threose nucleic acid (TNA), arabinoside, and mirror nucleoside (for example, beta-L-deoxynucleoside instead of beta-D-deoxynucleoside). Examples of dsRNA molecules comprising LNA nucleotides are disclosed in Elmen et al., (NAR 2005, 33(1):439-447).

The nucleic acid compounds of the present invention can be synthesized using one or more inverted nucleotides, for example inverted thymidine or inverted adenine (see, for example, Takei, et al., 2002, JBC 277(26):23800-06).

The term "unconventional moiety" as used herein includes an abasic ribose moiety, an abasic deoxyribose moiety, a deoxyribonucleotide, a modified deoxyribonucleotide, a mirror nucleotide (L-DNA and L-RNA), a non-base pairing nucleotide analog and a nucleotide joined to an adjacent nucleotide by a 2'-5' internucleotide phosphate bond; C3, C4, C5 and C6 moieties; threose nucleic acids (TNA, pyrazolotriazine base modified nucleic acid analogs (Pyr); morpholino; bridged nucleic acids including LNA and ethylene bridged nucleic acids (ENA).

The term "capping moiety" as used herein includes abasic ribose moiety, abasic deoxyribose moiety, modifications of abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'OMe nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; bridging or non bridging methylphosphonate, 5'-mercapto moieties or a phenyl hydrocarbyl moiety, for example THNB.

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate.

Inverted abasic deoxyribose moiety includes inverted deoxyriboabasic; 3',5' inverted deoxyriboabasic 5'-phosphate.

A "mirror" nucleotide is a nucleotide with reversed chirality to the naturally occurring or commonly employed nucleotide, i.e., a mirror image (L-nucleotide) of the naturally occurring (D-nucleotide). The nucleotide can be a ribonucleotide or a deoxyribonucleotide and may further comprise at least one sugar, base and/or backbone modification. U.S. Pat. No. 6,602,858 discloses nucleic acid catalysts comprising at least one L-nucleotide substitution. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU).

In various embodiments of Structure (A2), Z and Z' are absent. In other embodiments Z or Z' is present. In some embodiments each of Z and/or Z' independently includes a C2, C3, C4, C5 or C6 alkyl moiety, optionally a C3 [propane, —(CH2)3-] moiety or a derivative thereof including propanol (C3-OH/C3OH), propanediol, and phosphodiester derivative of propanediol ("C3Pi"). In preferred embodiments each of Z and/or Z' includes two hydrocarbon moieties and in some examples is C3Pi-C3OH or C3Pi-C3Pi. Each C3 is covalently conjugated to an adjacent C3 via a covalent bond, preferably a phospho-based bond. In some embodiments the phospho-based bond is a phosphorothioate, a phosphonoacetate or a phosphodiester bond.

In specific embodiments of Structure (A2) x=y=18 and Z comprises at least one C3 alkyl overhang. In some embodiments the C3-C3 overhang is covalently attached to the 3' terminus of (N)x or (N')y via a covalent linkage, preferably a phosphodiester linkage. In some embodiments the linkage between a first C3 and a second C3 is a phosphodiester linkage. In some embodiments the 3' non-nucleotide overhang is C3Pi-C3Pi. In some embodiments the 3' non-nucleotide overhang is C3Pi-C3Ps. In some embodiments the 3' non-nucleotide overhang is C3Pi-C3OH (OH is hydroxy). In some embodiments the 3' non-nucleotide overhang is C3Pi-C3OH. In preferred embodiments, the 3' overhang on the antisense strand is CH3Pi-CH3Pi.

In various embodiments the alkyl moiety comprises an alkyl derivative including a C3 alkyl, C4 alkyl, C5 alky or C6 alkyl moiety comprising a terminal hydroxyl, a terminal amino, or terminal phosphate group. In some embodiments the alkyl moiety is a C3 alkyl or C3 alkyl derivative moiety. In some embodiments the C3 alkyl moiety comprises propanol, propylphosphate, propylphosphorothioate or a combination thereof. The C3 alkyl moiety is covalently linked to the 3' terminus of (N')y and/or the 3' terminus of (N)x via a phosphodiester bond. In some embodiments the alkyl moiety comprises propanol, propyl phosphate or propyl phosphorothioate. In some embodiments each of Z and Z' is independently selected from propanol, propyl phosphate propyl phosphorothioate, combinations thereof or multiples thereof in particular 2 or 3 covalently linked propanol, propyl phosphate, propyl phosphorothioate or combinations thereof. In some embodiments each of Z and Z' is independently selected from propyl phosphate, propyl phosphorothioate, propyl phospho-propanol; propyl phospho-propyl phosphorothioate; propylphospho-propyl phosphate; (propyl phosphate)3, (propyl phosphate)2-propanol, (propyl phosphate)2-propyl phosphorothioate. Any propane or propanol conjugated moiety can be included in Z or Z'.

The structures of exemplary 3' terminal non-nucleotide moieties are as follows:

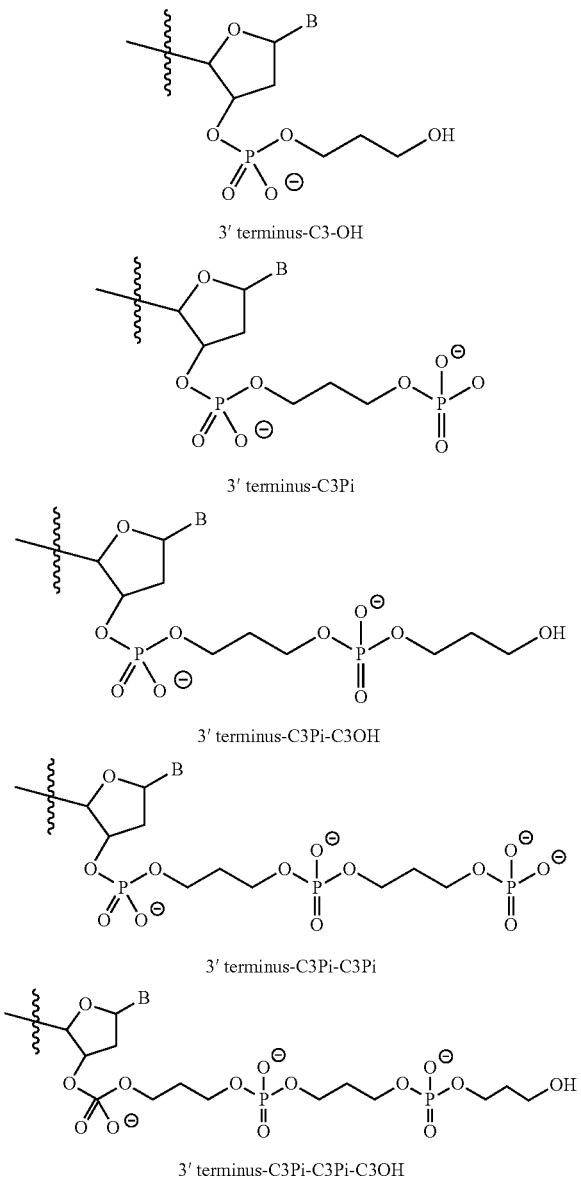

3' terminus-C3-OH

3' terminus-C3Pi

3' terminus-C3Pi-C3OH

3' terminus-C3Pi-C3Pi

3' terminus-C3Pi-C3Pi-C3OH

Phenyl Hydrocarbyl Conjugate

In some embodiments provided are dsRNA molecules that target DDIT4 covalently bound, directly or via a linker, to at least one phenyl hydrocarbyl moiety of general formula I: I

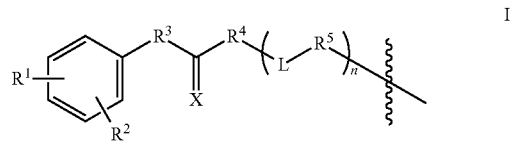

wherein

R$^1$ and R$^2$ each is independently selected from the group consisting of H, halogen, C$_1$-C$_{10}$ hydrocarbyl group, OR$^6$, OCOR$^6$, COOR$^6$, CH$_2$OR$^6$, CHO, COR$^6$, NR$^6$R$^7$ and SR$^6$; or R$^1$ and R$^2$ together with the carbons to which they are attached form a saturated or unsaturated cyclic C$_1$-C$_8$ hydrocarbyl ring optionally interrupted by up to 2 heteroatoms selected from oxygen, nitrogen or sulfur and the ring optionally substituted by up to 3 groups independently selected from the group consisting of halogen, C$_1$-C$_3$ hydrocarbyl group, OR$^6$, OCOR$^6$, COOR$^6$, CH$_2$OR$^6$, CHO, COR$^6$, NR$^6$R$^7$, SR$^6$, =O, =S and =NH;

R$^3$ is a C$_1$-C$_8$ hydrocarbyl group optionally interrupted by up to 2 heteroatoms selected from oxygen, nitrogen or sulfur;

R$^4$ is NH, O, S or CR$^6$R$^7$;

R$^6$ and R$^7$ each is independently selected from the group consisting of H and a C$_1$-C$_4$ hydrocarbyl group;

X is O or S;

n is an integer of 0 to 10; each L in n said (L-R$^5$) groups is independently selected from the group consisting of R$^8$O—, a peptidyl chain of up to 12 amino acid residues, —[CH$_2$—CH$_2$—O]$_m$— and a C$_1$-C$_{12}$ hydrocarbyl group optionally interrupted by up to 2 heteroatoms selected from 0, N or S; R$^8$ is a C$_1$-C$_{12}$ hydrocarbyl group optionally interrupted by up to 2 heteroatoms selected from O, N or S;

m is an integer of 1 to 10;

each R$^5$ in n said (L-R$^5$) groups is independently selected from the group consisting of —P(O)(R$^9$)—O—, —C(O)NH—, —O—; —NH—, —S—, —C(O)—; —C(O)O—; —NHCS—; —NHCO— and a single bond;

R$^9$ is selected from the group consisting of O$^-$, S$^-$, BH$_3^-$, NR$^6$R$^7$ and CH$_3$;

or a pharmaceutically acceptable salt thereof;

wherein the sense strand has sequence identity to a consecutive segment of a mRNA corresponding to a target gene.

In one embodiment, the dsRNA is covalently bound to a compound of formula I wherein X is O, R$^4$ is NH, R$^1$ and R$^2$ form a cyclic C$_4$ ring fused to the phenyl ring of

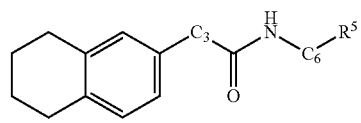

formula I or II, R$^3$ is C$_3$ alkyl, L is a C$_6$ alkyl and provided herein is a 4-phenylbutyric amide derivative 6[(5,6,7,8-tetrahydronaphthalene)butyric amide] (THNB) of the general formula III:

III

In some embodiments 6[(5,6,7,8-tetrahydronaphthalene)butyric amide] (THNB) is linked to the 5' terminus of an oligonucleotide, for example the 5' terminus of a sense strand of a dsRNA and has the general formula IV:

IV

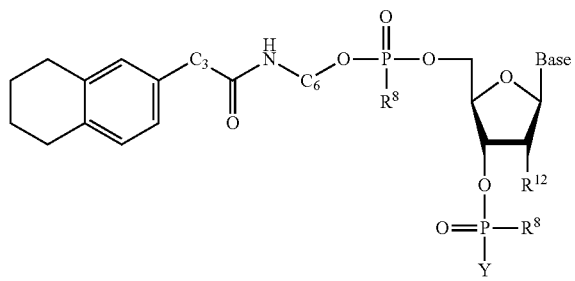

wherein Y is an oligonucleotide of about 16 to 39 nucleotides in length, linked to the 5'O of the adjacent nucleotide;

wherein Base is adenine, guanine, cytosine, uracil, thymidine or an analog thereof; and wherein R$^{12}$ is H, OH, OR$^6$, NR$^6$R$^7$, OR$^6$OR$^7$.

Indications

The double stranded nucleic acid molecules to DDIT4 disclosed herein are useful in therapy in general and in particular in the prevention and or treatment of a variety of diseases and disorders in which the etiology or progression of the disease or disorder is related to DDIT4 expression. Non-limiting examples of such disease and disorders follow.

Neuroprotection

In various aspects provided herein is a method of providing neuroprotection, effecting axonal growth and or stimulation of neural progenitor cells to a subject in need thereof comprising administering to the subject a therapeutically effective dose of a dsRNA disclosed herein that down regulates expression of DDIT4 thereby providing neuroprotection, effecting axonal growth and or stimulation of neural progenitor cells. In some embodiments dsRNA disclosed herein promote growth of axons (e.g. post trauma in eyes or any organ with neurological dysfunction) and/or to promote myelination (e.g. post trauma or demyelination disorders).

In some embodiments the methods disclosed herein comprise providing neuroprotection to a ganglion cell. In some embodiments the ganglion cell is a retinal ganglion cell. In various embodiments the methods comprise promoting axonal growth of a neuroprogenitor cell. In some embodiments the neuroprogenitor cell is a retinal neuroprogenitor cell. In some embodiments the methods comprise providing neuroprotection to a retinal ganglion cell and/or promoting axonal growth of a retinal neuroprogenitor cell.

Atrophy: In some embodiments, the dsRNA molecules disclosed herein are useful in attenuating muscle atrophy, for example muscle atrophy resulting from bone fracture or long term immobilization of muscle.

In other embodiments, the dsRNA molecules disclosed herein are useful in attenuating skin atrophy, for example skin atrophy associated with oxidative stress resulting from steroid treatment, UV exposure or aging.

Eye Diseases: In some embodiments, provided herein is a method of treating a disease, disorder or injury comprising administering to the subject a therapeutically effective dose of a dsRNA disclosed herein that down regulates expression of DDIT4 thereby treating the disease, disorder, or injury is selected from the group consisting of glaucoma, including open angle glaucoma (OAG), diabetic retinopathy (DR), diabetic macular edema (DME), age related macular degeneration (AMD), wet age related macular degeneration (wet AMD) Leber's hereditary optic neuropathy (LHON), Leber's optic atrophy, optic neuritis, retinal artery occlusion, central retinal vein occlusion, brunch retinal vein occlusion, ischemic optic neuropathy, optic nerve injury, retinopathy of prematurity (ROP) or retinitis pigmentosa (RP), retinal ganglion degeneration, macular degeneration, hereditary optic neuropathy, metabolic optic neuropathy, optic neuropathy due to a toxic agent or neuropathy caused by adverse drug reactions or vitamin deficiency, inflammation, ischemia, infection or compression from tumors or aneurysms. In some embodiments the disease, disorder or injury is a result of elevated intraocular pressure (IOP). In some embodiments the disease, disorder or injury is associated with diabetes. In preferred embodiments the eye disease, disorder or injury is glaucoma, DME, optic neuritis and optic neuropathy. In some embodiment the optic neuropathy is selected from non-arteritic anterior ischemic optic neuropathy (NAION), optic neuritis, neuromyelitis optica, dominant optic atrophy, Leber's hereditary optic neuropathy. In some preferred embodiments the disease is glaucoma. In some preferred embodiments the eye disease is DME.

Microvascular disorders: Microvascular disorders include a broad group of conditions that primarily affect the microscopic capillaries and lymphatics and are therefore outside the scope of direct surgical intervention. Microvascular disease can be broadly grouped into the vasospastic, the vasculitis and lymphatic occlusive. Additionally, many of the known vascular conditions have a microvascular element to them. Disorders categorized as "microvascular disorders" may also be classified as for example, kidney, ophthalmic or inflammatory diseases or disorders Microvascular pathologies associated with diabetes: Diabetes is the leading cause of blindness, the number one cause of amputations and impotence, and one of the most frequently occurring chronic childhood diseases. Diabetes is also the leading cause of end-stage renal disease in the United States, with a prevalence rate of 31% compared with other renal diseases. Diabetes is also the most frequent indication for kidney transplantation, accounting for 22% of all transplantations.

In general, diabetic complications can be classified broadly as microvascular or macrovascular disease. Microvascular complications include neuropathy (nerve damage), nephropathy (kidney disease) and vision disorders (e.g. retinopathy, glaucoma, cataract and corneal disease). In the retina, glomerulus, and vasa nervorum, similar pathophysiologic features characterize diabetes-specific microvascular disease (For further information, see Larsen: Williams Textbook of Endocrinology, 10th ed., 2003 Elsevier).

Neuropathy: Neuropathy affects all peripheral nerves: pain fibers, motor neurons, autonomic nerves and therefore necessarily can affect all organs and systems. There are several distinct syndromes based on the organ systems and members affected, but these are by no means exclusive. A patient can have sensorimotor and autonomic neuropathy or any other combination. Despite advances in the understanding of the metabolic causes of neuropathy, treatments aimed at interrupting these pathological processes have been limited by side effects and lack of efficacy. Thus, treatments are symptomatic and do not address the underlying problems. Agents for pain caused by sensorimotor neuropathy include tricyclic antidepressants (TCAs), serotonin reuptake inhibitors (SSRIs) and antiepileptic drugs (AEDs). None of these agents reverse the pathological processes leading to diabetic neuropathy and none alter the relentless course of the illness. The molecules disclosed herein are useful in treating subjects afflicted with neuropathy.

Diabetic neuropathy: Diabetic neuropathies are neuropathic disorders (peripheral nerve damage) that are associated with diabetes mellitus. These conditions usually result from diabetic microvascular injury involving small blood vessels that supply nerves (vasa nervorum). Relatively common conditions which may be associated with diabetic neuropathy include third nerve palsy; mononeuropathy; mononeuropathy multiplex; diabetic amyotrophy; a painful polyneuropathy; autonomic neuropathy; and thoracoabdominal neuropathy and the most common form, peripheral neuropathy, which mainly affects the feet and legs. There are four factors involved in the development of diabetic neuropathy: microvascular disease, advanced glycated end products, protein kinase C, and the polyol pathway.

Diabetic Limb Ischemia and Diabetic foot ulcers: Diabetes and pressure can impair microvascular circulation and lead to changes in the skin on the lower extremities, which in turn, can lead to formation of ulcers and subsequent infection. Microvascular changes lead to limb muscle microangiopathy, as well as a predisposition to develop peripheral ischemia and a reduced angiogenesis compensatory response to ischemic events. Microvascular pathology exacerbates Peripheral Vascular Disease (PVD) (or Peripheral Arterial Disease (PAD) or Lower Extremity Arterial Disease (LEAD)—a MACROvascular complication—narrowing of the arteries in the legs due to atherosclerosis. PVD occurs earlier in diabetics, is more severe and widespread, and often involves intercurrent microcirculatory problems affecting the legs, eyes, and kidneys.

Foot ulcers and gangrene are frequent comorbid conditions of PAD. Concurrent peripheral neuropathy with impaired sensation renders the foot susceptible to trauma, ulceration, and infection. The progression of PAD in diabetes is compounded by such comorbidity as peripheral neuropathy and insensitivity of the feet and lower extremities to pain and trauma.

Coronary Microvascular Dysfunction in Diabetes: The correlation between histopathology and microcirculatory dysfunction in diabetes is well known from old experimental studies and from autopsy, where thickening of the basal membrane, perivascular fibrosis, vascular rarefication, and capillary hemorrhage are frequently found. The molecules disclosed herein are useful in treating subjects afflicted with neuropathy and coronary microvascular dysfunction in non-obstructive coronary artery disease (CAD).

Diabetic nephropathy (Renal dysfunction in patients with diabetes): Diabetic nephropathy encompasses microalbuminuria (a microvascular disease effect), proteinuria and end stage renal disease (ESRD). Diabetes is the most common cause of kidney failure, accounting for more than 40 percent of new cases. Even when drugs and diet are able to control diabetes, the disease can lead to nephropathy and kidney failure. Most people with diabetes do not develop nephropathy that is severe enough to cause kidney failure. About 16 million people in the United States have diabetes, and about 100,000 people have kidney failure as a result of diabetes. The molecules disclosed herein are useful in treating subjects afflicted with diabetic nephropathy.

Diabetic retinopathy: According to the World Health Organization, diabetic retinopathy is the leading cause of blindness in working age adults and a leading cause of vision loss in diabetics. The American Diabetes Association reports that there are approximately 18 million diabetics in the United States and approximately 1.3 million newly diagnosed cases of diabetes in the United States each year.

Diabetic retinopathy is defined as the progressive dysfunction of the retinal vasculature caused by chronic hyperglycemia. Key features of diabetic retinopathy include microaneurysms, retinal hemorrhages, retinal lipid exudates, cotton-wool spots, capillary nonperfusion, macular edema and neovascularization. Associated features include vitreous hemorrhage, retinal detachment, neovascular glaucoma, premature cataract and cranial nerve palsies.

Specifically, apoptosis has been localized to glial cells such as Mueller cells and astrocytes and has been shown to occur within 1 month of diabetes in the STZ-induced diabetic rat model. The cause of these events is multifactorial including activation of the diacylglycerol/PKC pathway, oxidative stress, and non-enzymatic glycosylation. The combination of these events renders the retina hypoxic and ultimately leads to the development of diabetic retinopathy. One possible connection between retinal ischemia and the early changes in the diabetic retina is the hypoxia-induced production of growth factors such as VEGF. The master regulator of the hypoxic response has been identified as hypoxia inducible factor-1 (HIF-1), which controls genes that regulate cellular proliferation and angiogenesis. DDIT4 is responsive to hypoxia-responsive transcription factor hypoxia-inducible factor 1 (HIF-1) and is typically up-regulated during hypoxia both in vitro and in vivo in an animal model of ischemic stroke.

Diabetic Macular Edema (DME): Prevent Blindness America and the National Eye Institute estimate that in the United States there are over 5.3 million people aged 18 or older with diabetic retinopathy, including approximately 500,000 with DME. The CDC estimates that there are approximately 75,000 new cases of DME in the United States each year. DME is a complication of diabetic retinopathy, a disease affecting the blood vessels of the retina. Diabetic retinopathy results in multiple abnormalities in the retina, including retinal thickening and edema, hemorrhages, impeded blood flow, excessive leakage of fluid from blood vessels and, in the final stages, abnormal blood vessel growth. This blood vessel growth can lead to large hemorrhages and severe retinal damage. When the blood vessel leakage of diabetic retinopathy causes swelling in the macula, it is referred to as DME. The principal symptom of DME is a loss of central vision. Risk factors associated with DME include poorly controlled blood glucose levels, high blood pressure, abnormal kidney function causing fluid retention, high cholesterol levels and other general systemic factors. A double stranded RNA molecule that down regulates DDIT4, known as REDD14 or PF-655, is a clinical candidate for the treatment of DME. The dsRNA molecules disclosed herein are useful in treating subjects afflicted with DME.

Microvascular Diseases of the Kidney: The kidney is involved in a number of discreet clinicopathologic conditions that affect systemic and renal microvasculature. Certain of these conditions are characterized by primary injury to endothelial cells, such as: hemolytic-uremic syndrome (HUS) and thrombotic thrombocytopenic purpura (TTP). HUS and TTP are closely related diseases characterized by microangiopathic hemolytic anemia and variable organ impairment. Traditionally, the diagnosis of HUS is made when renal failure is a predominant feature of the syndrome, as is common in children. In adults, neurological impairment frequently predominates and the syndrome is then referred to as TTP. Thrombotic microangiopathy is the underlying pathologic lesion in both syndromes, and the clinical and laboratory findings in patients with either HUS or TTP overlap to a large extent. This has prompted several investigators to regard the two syndromes as a continuum of a single disease entity.

Pathogenesis: Experimental data strongly suggest that endothelial cell injury is the primary event in the pathogenesis of HUS/TTP. Endothelial damage triggers a cascade of events that includes local intravascular coagulation, fibrin deposition, and platelet activation and aggregation. The end result is the histopathological finding of thrombotic microangiopathy common to the different forms of the HUS/TTP syndrome. If HUS/TTP is left untreated, the mortality rate approaches 90%. Supportive therapy—including dialysis, antihypertensive medications, blood transfusions, and management of neurological complications—contributes to the improved survival of patients with HUS/TTP. Adequate fluid balance and bowel rest are important in treating typical HUS associated with diarrhea.

Radiation Nephritis: The long-term consequences of renal irradiation in excess of 2500 rad can be divided into five clinical syndromes:
(i) Acute radiation nephritis occurs in approximately 40% of patients after a latency period of 6 to 13 months. It is characterized clinically by abrupt onset of hypertension, proteinuria, edema, and progressive renal failure in most cases leading to end-stage kidneys.
(ii) Chronic radiation nephritis, conversely, has a latency period that varies between 18 months and 14 years after the initial insult. It is insidious in onset and is characterized by hypertension, proteinuria, and gradual loss of renal function.
(iii) The third syndrome manifests 5 to 19 years after exposure to radiation as benign proteinuria with normal renal function.
(iv) A fourth group of patients exhibits only benign hypertension 2 to 5 years later and may have variable proteinuria. Late malignant hypertension arises 18 months to 11 years after irradiation in patients with either chronic radiation nephritis or benign hypertension. Removal of the affected kidney reversed the hypertension. Radiation-induced damage to the renal arteries with subsequent Reno vascular hypertension has been reported.
(v) A syndrome of renal insufficiency analogous to acute radiation nephritis has been observed in bone marrow transplantation (BMT) patients who were treated with total-body irradiation (TBI).

Retinal microvasculopathy (AIDS retinopathy): The dsRNA molecules disclosed herein are useful in treating subjects afflicted with retinopathies with different etiologies. Retinal microvasculopathy is seen in 100% of AIDS patients and is characterized by intraretinal hemorrhages, microaneurysms, Roth spots, cotton-wool spots (microinfarctions of the nerve fiber layer) and perivascular sheathing.

Bone marrow transplantation (BMT) retinopathy: Bone marrow transplantation retinopathy was first reported in 1983. It typically occurs within six months, but it can occur as late as 62 months after BMT. Risk factors such as diabetes and hypertension may facilitate the development of BMT retinopathy by heightening the ischemic microvasculopathy. There is no known age, gender or race predilection for development of BMT retinopathy. Patients present with decreased visual acuity and/or visual field deficit. Posterior segment findings are typically bilateral and symmetric. Clinical manifestations include multiple cotton wool spots, telangiectasia, microaneurysms, macular edema, hard exudates and retinal hemorrhages. Fluorescein angiography demonstrates capillary nonperfusion and dropout, intraretinal microvascular abnormalities, microaneurysms and macular edema. Although the precise etiology of BMT retinopathy has not been elucidated, it appears to be affected by several factors: cyclosporine toxicity, total body irradiation (TBI), and chemotherapeutic agents. Cyclosporine is a powerful immunomodulatory agent that suppresses graft-versus-host immune response. It may lead to endothelial cell injury and neurological side effects, and as a result, it has been suggested as the cause of BMT retinopathy. However, BMT retinopathy can develop in the absence of cyclosporine use, and cyclosporine has not been shown to cause BMT retinopathy in autologous or syngeneic bone marrow recipients. Cyclosporine does not, therefore, appear to be the sole cause of BMT retinopathy. Total body irradiation (TBI) has also been implicated as the cause of BMT retinopathy. Radiation injures the retinal microvasculature and leads to ischemic vasculopathy.

Glaucoma: Glaucoma is one of the leading causes of blindness in the world. It affects approximately 66.8 million people worldwide. At least 12,000 Americans are blinded by this disease each year (Kahn and Milton, Am J Epidemiol. 1980, 111(6):769-76). Glaucoma is characterized by the degeneration of axons in the optic nerve head, primarily due to elevated intraocular pressure (IOP). One of the most common forms of glaucoma, known as primary open-angle glaucoma (POAG), results from the increased resistance of aqueous humor outflow in the trabecular Meshwork™, causing IOP elevation and eventual optic nerve damage. Other main types of glaucoma are angle closure glaucoma, normal tension glaucoma and pediatric glaucoma. These are also marked by an increase of intraocular pressure (IOP), or pressure inside the eye. Optic nerve damage with a normal IOP, is known as normal tension glaucoma. Secondary glaucoma refers to any case in which another disease causes or contributes to increased eye pressure, resulting in optic nerve damage and vision loss. Mucke (IDrugs 2007, 10(1): 37-41) reviews current therapeutics, including siRNA to various targets for the treatment of ocular diseases, for example, age-related macular degeneration (AMD) and glaucoma.

Macular degeneration: The most common cause of decreased best-corrected vision in individuals over 65 years of age in the US is the retinal disorder known as age-related macular degeneration (AMD). As AMD progresses, the disease is characterized by loss of sharp, central vision. The area of the eye affected by AMD is the Macula—a small area in the center of the retina, composed primarily of photoreceptor cells. So-called "dry" AMD, accounting for about 85%-90% of AMD patients, involves alterations in eye pigment distribution, loss of photoreceptors and diminished retinal function due to overall atrophy of cells. So-called "wet" AMD involves proliferation of abnormal choroidal vessels leading to clots or scars in the sub-retinal space. Thus, the onset of wet AMD occurs because of the formation of an abnormal choroidal neovascular network (choroidal neovascularization, CNV) beneath the neural retina. The newly formed blood vessels are excessively leaky. This leads to accumulation of subretinal fluid and blood leading to loss of visual acuity. Eventually, there is total loss of functional retina in the involved region, as a large disciform scar involving choroids and retina forms. While dry AMD patients may retain vision of decreased quality, wet AMD often results in blindness. (Hamdi & Kenney, Frontiers in Bioscience, e305-314, May 2003). CNV occurs not only in wet AMD but also in other ocular pathologies such as ocular histoplasmosis syndrome, angiod streaks, ruptures in Bruch's membrane, myopic degeneration, ocular tumors and some retinal degenerative diseases.

Ocular Ischemic Syndrome: Patients suffering from ocular ischemic syndrome (OIS) are generally elderly, ranging in age from the 50s to 80s. Males are affected twice as commonly as females. The patient is only rarely asymptomatic. Decreased vision occurs at presentation in 90 percent of cases, and 40 percent of patients have attendant eye pain. There may also be an attendant or antecedent history of transient ischemic attacks or amaurosis fugax. Patients also have significant known or unknown systemic disease at the time of presentation. The most commonly encountered systemic diseases are hypertension, diabetes, ischemic heart disease, stroke, and peripheral vascular disease. To a lesser extent, patients manifest OIS as a result of giant cell arteritis (GCA).

Unilateral findings are present in 80 percent of cases. Common findings may include advanced unilateral cataract, anterior segment inflammation, asymptomatic anterior chamber reaction, macular edema, dilated but non-tortuous retinal veins, mid-peripheral dot and blot hemorrhages, cotton wool spots, exudates, and neovascularization of the disc and retina. There may also be spontaneous arterial pulsation, elevated intraocular pressure, and neovascularization of the iris and angle with neovascular glaucoma (NVG). While the patient may exhibit anterior segment neovascularization, ocular hypotony may occur due to low arterial perfusion to the ciliary body. Occasionally, there are visible retinal emboli (Hollenhorst plaques).

Dry-Eye Syndrome: Dry eye syndrome is a common problem usually resulting from a decrease in the production of tear film that lubricates the eyes. Most patients with dry eye experience discomfort, and no vision loss; although in severe cases, the cornea may become damaged or infected. Wetting drops (artificial tears) may be used for treatment while lubricating ointments may help more severe cases.

Additional Eye Disorders: The molecules and compositions described herein are useful in the treatment of choroidal neovascularization (CNV), which occurs not only in wet AMD but also in other ocular pathologies such as ocular histoplasmosis syndrome, angiod streaks, ruptures in Bruch's membrane, myopic degeneration, ocular tumors and some retinal degenerative diseases.

Hearing Loss: In various embodiments, the double stranded nucleic acid molecules disclosed herein are applied to various conditions of hearing loss. Without being bound by theory, the hearing loss may be due to apoptotic inner ear hair cell damage or loss (Zhang et al., Neuroscience 2003. 120:191-205; Wang et al., J. Neuroscience 23((24):8596-8607), wherein the damage or loss is caused by infection, mechanical injury, loud sound (noise), aging (presbycusis), or chemical-induced ototoxicity.

By "ototoxin" as used herein is meant a substance that through its chemical action injures, impairs or inhibits the activity of the sound receptors component of the nervous system related to hearing, which in turn impairs hearing (and/or balance). Ototoxicity includes a deleterious effect on the inner ear hair cells. Ototoxins include therapeutic drugs including antineoplastic agents, salicylates, loop-diuretics, quinines, and aminoglycoside antibiotics, contaminants in foods or medicinals, and environmental or industrial pollutants. Typically, treatment is performed to prevent or reduce ototoxicity, especially resulting from or expected to result from administration of therapeutic drugs. Preferably a therapeutically effective composition comprising the double stranded nucleic acid molecules disclosed herein is given immediately after the exposure to prevent or reduce the ototoxic effect. More preferably, treatment is provided prophylactically, either by administration of the pharmaceutical composition prior to or concomitantly with the ototoxic pharmaceutical or the exposure to the ototoxin. Incorporated herein by reference are chapters 196, 197, 198 and 199 of The Merck Manual of Diagnosis and Therapy, 14th Edition, (1982), Merck Sharp & Dome Research Laboratories, N.J. and corresponding chapters in the most recent 16th edition, including Chapters 207 and 210) relating to description and diagnosis of hearing and balance impairments.

Ototoxicity is a dose-limiting side effect of antibiotic administration. From 4 to 15% of patients receiving 1 gram per day for greater than 1 week develop measurable hearing loss, which slowly becomes worse and can lead to complete permanent deafness if treatment continues. Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof. Particular antibiotics include neomycin B, kanamycin A, kanamycin B, gentamicin C1, gentamicin C1a, and gentamicin C2, and the like that are known to have serious toxicity, particularly ototoxicity and nephrotoxicity, which reduce the usefulness of such antimicrobial agents (see Goodman and Gilman's The Pharmacological Basis of Therapeutics, 6th ed., A. Goodman Gilman et al., eds; Macmillan Publishing Co., Inc., New York, pp. 1169-71 (1980)).

Ototoxicity is also a serious dose-limiting side-effect for anti-cancer agents. Ototoxic neoplastic agents include but are not limited to vincristine, vinblastine, cisplatin and cisplatin-like compounds and taxol and taxol-like compounds. Cisplatin-like compounds include carboplatin (Paraplatin®), tetraplatin, oxaliplatin, aroplatin and transplatin inter alia and are platinum based chemotherapeutics.

Diuretics with known ototoxic side-effect, particularly "loop" diuretics include, without being limited to, furosemide, ethacrylic acid, and mercurials. Ototoxic quinines include but are not limited to synthetic substitutes of quinine that are typically used in the treatment of malaria. Salicylates, such as aspirin, are the most commonly used therapeutic drugs for their anti-inflammatory, analgesic, antipyretic and anti-thrombotic effects. Unfortunately, they too have ototoxic side effects. They often lead to tinnitus ("ringing in the ears") and temporary hearing loss. Moreover, if the drug is used at high doses for a prolonged time, the hearing impairment can become persistent and irreversible.

In some embodiments a molecule disclosed herein is co-administered with an ototoxin. For example, an improved method is provided for treatment of infection of a mammal by administration of an aminoglycoside antibiotic, the improvement comprising administering a therapeutically effective amount of one or more chemically modified molecules disclosed herein which down-regulate expression of DDIT4, to the subject in need of such treatment to reduce or prevent ototoxin-induced hearing impairment associated with the antibiotic. The double stranded RNA molecules described herein are preferably administered locally within the inner ear.

The methods, chemically modified molecules and pharmaceutical and compositions of the present invention are also effective in the treatment of acoustic trauma or mechanical trauma, preferably acoustic or mechanical trauma that leads to inner ear hair cell loss. With more severe exposure, injury can proceed from a loss of adjacent supporting cells to complete disruption of the organ of Corti. Death of the sensory cell can lead to progressive Wallerian degeneration and loss of primary auditory nerve fibers. The molecules disclosed herein are useful in treating acoustic trauma caused by a single exposure to an extremely loud sound, or following long-term exposure to everyday loud sounds above 85 decibels. The molecules disclosed herein are useful in treating mechanical inner ear trauma, for example, resulting from the insertion of an electronic device into the inner ear. The molecules disclosed herein prevent or minimize the damage to inner ear hair cells associated with the operation.

Another type of hearing loss is presbycusis, which is hearing loss that gradually occurs in most individuals as they age. About 30-35 percent of adults between the ages of 65 and 75 years and 40-50 percent of people 75 and older experience hearing loss. The molecules disclosed herein prevent, reduce or treat the incidence and/or severity of inner ear disorders and hearing impairments associated with presbycusis.

Lung Injury and Respiratory Disorders: In various embodiments the dsRNA molecules described herein are useful for treating or preventing the incidence or severity of acute lung injury, in particular conditions which result from ischemic/reperfusion injury or oxidative stress and for treating chronic obstructive pulmonary disease (COPD). Non-limiting examples of acute lung injuries include acute respiratory distress syndrome (ARDS) due to coronavirus infection or endotoxins, severe acute respiratory syndrome (SARS) and ischemia reperfusion injury associated with lung transplantation.

Chronic obstructive pulmonary disease (COPD), affects more than 16 million Americans and is the fourth highest cause of death in the United States. Cigarette smoking causes most occurrences of the debilitating disease but other environmental factors cannot be excluded (Petty T L. 2003. Clin. Cornerstone, 5-10).

Pulmonary emphysema is a major manifestation of COPD. Permanent destruction of peripheral air spaces, distal to terminal bronchioles, is the hallmark of emphysema (Tuder, et al. Am J Respir Cell Mol Biol, 29:88-97; 2003.). Emphysema is also characterized by accumulation of inflammatory cells such as macrophages and neutrophils in bronchioles and alveolar structures (Petty, 2003).

The pathogenesis of emphysema is complex and multifactorial. In humans, a deficiency of inhibitors of proteases produced by inflammatory cells, such as alpha 1-antitrypsin, has been shown to contribute to protease/antiprotease imbalance, thereby favoring destruction of alveolar extracellular matrix in cigarette-smoke (CS) induced emphysema (Eriksson, S. 1964. Acta Med Scand 175:197-205. Joos, L., Pare, P. D., and Sandford, A. J. 2002. Swiss Med Wkly 132:27-37).

An additional pathogenic factor with regards to COPD pathogenesis is the observed decreased expression of VEGF and VEGFRII in lungs of emphysematous patients (Yasunori Kasahara, et al. Am J Respir Crit Care Med. Vol 163. pp 737-744, 2001). Moreover, inhibition of VEGF signaling using chemical VEGFR inhibitor leads to alveolar septal endothelial and then to epithelial cell apoptosis, probably due to disruption of intimate structural/functional connection of both types of cells within alveoli (Yasunori Kasahara et al. J. Clin. Invest. 106:1311-1319 (2000); Voelkel N F, Cool C D, Eur Respir J Suppl. 2003. 46:28s-32s).

In various embodiments pharmaceutical composition for treatment of respiratory disorders may be comprised of the following compound combinations: chemically modified DDIT4 dsRNA molecules disclosed herein combined with a siRNA compound that targets one or more of the following genes: elastases, matrix metalloproteases, phospholipases, caspases, sphingomyelinase, and ceramide synthase.

Acute respiratory distress syndrome (ARDS), also known as respiratory distress syndrome (RDS) or adult respiratory distress syndrome (in contrast with infant respiratory distress syndrome, IRDS) is a serious reaction to various forms of injuries to the lung. This is the most important disorder resulting in increased permeability pulmonary edema.

ARDS is a severe lung disease caused by a variety of direct and indirect insults. It is characterized by inflammation of the lung parenchyma leading to impaired gas exchange with concomitant systemic release of inflammatory mediators which cause inflammation, hypoxemia and frequently result in failure of multiple organs. This condition is life threatening and often lethal, usually requiring mechanical ventilation and admission to an intensive care unit. A less severe form is called acute lung injury (ALI).

Kidney Diseases and Disorders: The dsRNA molecules disclosed herein are useful in treating or preventing various diseases and disorders that affect the kidney as disclosed herein below. Acute Renal Failure (ARF)

In various embodiments, the dsRNA molecules disclosed herein are used for treating kidney disorders, in particular acute renal failure (ARF) due to ischemia in post surgical patients, in kidney transplant patients, and acute renal failure due to chemotherapy treatment such as cisplatin administration or sepsis-associated acute renal failure.

ARF can be caused by microvascular or macrovascular disease (major renal artery occlusion or severe abdominal aortic disease). The classic microvascular diseases often present with microangiopathic hemolysis and acute renal failure occurring because of glomerular capillary thrombosis or occlusion, often with accompanying thrombocytopenia. Typical examples of these diseases include:

a) Thrombotic thrombocytopenic purpura—The classic pentad in thrombotic thrombocytopenic purpura includes fever, neurological changes, renal failure, microangiopathic hemolytic anemia and thrombocytopenia.

b) Hemolytic uremic syndrome—Hemolytic uremic syndrome is similar to thrombotic thrombocytopenic purpura but does not present with neurological changes.

c) HELLP syndrome (hemolysis, elevated liver enzymes and low platelets). HELLP syndrome is a type of hemolytic uremic syndrome that occurs in pregnant women with the addition of transaminase elevations.

Acute renal failure can present in all medical settings but is predominantly acquired in hospitals. The condition develops in 5 percent of hospitalized patients, and approximately 0.5 percent of hospitalized patients require dialysis. Over the past 40 years, the survival rate for acute renal failure has not improved, primarily because affected patients are now older and have more comorbid conditions. Infection accounts for 75 percent of deaths in patients with acute renal failure, and cardio-respiratory complications are the second most common cause of death. Depending on the severity of renal failure, the mortality rate can range from 7 percent to as high as 80 percent. Acute renal failure can be divided into three categories: Prerenal, intrinsic and postrenal ARF. Intrinsic ARF is subdivided into four categories: tubular disease, glomerular disease, vascular disease (includes microvascular) and interstitial disease.

A preferred use of the double stranded nucleic acid molecules disclosed herein is for the prevention of acute renal failure in high-risk patients undergoing major cardiac surgery or vascular surgery. The patients at high-risk of developing acute renal failure can be identified using various scoring methods such as the Cleveland Clinic algorithm or that developed by US Academic Hospitals (QMMI) and by Veterans' Administration (CICSS).

Pharmaceutical Compositions

Provided are compositions and methods for down-regulation of DDIT4 expression by using small nucleic acid molecules, such as short interfering nucleic acid (siNA), interfering RNA (RNAi), short interfering RNA (siRNA), double-stranded RNA (dsRNA), micro-RNA (miRNA), and short hairpin RNA (shRNA) molecules capable of mediating down-regulation of DDIT4 gene expression or that mediate RNA interference against DDIT4 gene expression.

While it may be possible for the molecules disclosed herein to be administered as the raw chemical, it is preferable to present them as a pharmaceutical composition. Accordingly provided is a pharmaceutical composition comprising one or more of the dsRNA molecules disclosed herein; and a pharmaceutically acceptable carrier. This composition may comprise a mixture of two or more different nucleic acid compounds.

Compositions, methods and kits provided herein may include one or more nucleic acid molecules (e.g., dsRNA) and methods that independently or in combination modulate (e.g., down-regulate) the expression of DDIT4 protein and/or genes encoding DDIT4 protein, proteins and/or genes associated with the maintenance and/or development of diseases, conditions or disorders associated with expression of DDIT4.

The description of the various aspects and embodiments is provided with reference to DDIT4. However, the various aspects and embodiments are also directed to other related DDIT4 transcript variants, and polymorphisms (e.g., single nucleotide polymorphism, (SNPs)) associated with the DDIT4 genes.

Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

Additionally, provided is a method of inhibiting the expression of DDIT4 by at least 20%, by at least 30% by at least 40%, preferably by 50%, 60% or 70%, more preferably by 75%, 80% or 90% as compared to a control comprising contacting an mRNA transcript (e.g. SEQ ID NO:1) of with one or more of the dsRNA molecules disclosed herein.

In one embodiment the molecules, compositions and methods disclosed herein inhibit/down-regulate the DDIT4 gene, whereby the inhibition/down-regulation is selected from the group comprising inhibition/down-regulation of gene function, inhibition/down-regulation of polypeptide and inhibition/down-regulation of mRNA expression.

In one embodiment the nucleic acid compounds, compositions and methods provided herein, inhibit expression of the DDIT4 polypeptide, whereby the inhibition is selected from the group comprising inhibition of function (which may be examined by an enzymatic assay or a binding assay with a known interactor of the native gene/polypeptide, inter alia), down-regulation of protein or inhibition of protein (which may be examined by Western blotting, ELISA or immuno-precipitation, inter alia) and inhibition of mRNA expression (which may be examined by Northern blotting, quantitative RT-PCR, in-situ hybridisation or microarray hybridisation, inter alia).

In one embodiment, the compositions and methods provided herein include a nucleic acid molecule having RNAi activity against DDIT4 mRNA, where the nucleic acid molecule includes a sequence complementary to an RNA having DDIT4 encoding sequence, such as that sequence set forth in SEQ ID NO: 1. In another embodiment, a nucleic acid molecule may have RNAi activity against DDIT4 RNA, where the nucleic acid molecule includes a sequence complementary to an RNA having variant DDIT4 encoding sequence, for example a mutant DDIT4 gene not shown in SEQ ID NO:1 but known in the art to be associated with the onset and/or maintenance and/or development of neurodegeneration and/or other diseases and disorders, for example a SNP.

Delivery and Formulations

The DDIT4 dsRNA molecules disclosed herein may be delivered to the ear by direct application of pharmaceutical composition to the outer ear; by transtympanic injection or by ear drops. In some embodiments the pharmaceutical composition is applied to the ear canal. Delivery to the ear may also be referred to as aural or otic delivery comprising siRNA; a penetration enhancer and a pharmaceutically acceptable vehicle.

Nucleic acid molecules may be delivered to the target tissue by direct application of the naked molecules prepared with a carrier or a diluent.

The terms "naked nucleic acid" or "naked dsRNA" or "naked siRNA" refers to nucleic acid molecules that are free from any delivery vehicle that acts to assist, promote or facilitate entry into the cell, including viral sequences, viral particles, liposome formulations, lipofectin or precipitating agents and the like. For example, dsRNA in PBS is "naked dsRNA".

Nucleic acid molecules disclosed herein may be delivered or administered directly with a carrier or diluent that acts to assist, promote or facilitate entry to the cell, including viral vectors, viral particles, liposome formulations, lipofectin or precipitating agents and the like.

A nucleic acid molecule may include a delivery vehicle, including liposomes, for administration to a subject, carriers and diluents and their salts, and/or can be present in pharmaceutically acceptable formulations. In some embodiments the dsRNA molecules disclosed herein are delivered in liposome formulations and lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al., FEBS Let. 2003, 539:111-114; Xia et al., Nat. Biotech. 2002, 20:1006-1010; Reich et al., Mol. Vision 2003, 9: 210-216; Sorensen et al., J. Mol. Biol. 2003. 327: 761-766; Lewis et al., Nat. Gen. 2002, 32: 107-108 and Simeoni et al., NAR 2003, 31, 11: 2717-2724). siRNA has recently been successfully used for inhibition of gene expression in primates (see for example, Tolentino et al., Retina 24(4):660).

Delivery of naked or formulated RNA molecules to the ear, optionally the inner ear, is accomplished, inter alia, by transtympanic injection or by administration of the desired compound formulated as an ear drop. Otic compositions comprising dsRNA are disclosed in US Publication No. 20110142917, to the assignee of the present application and incorporated herein by reference in its entirety.

Polypeptides that facilitate introduction of nucleic acid into a desired subject are known in the art, e.g. such as those described in US. Application Publication No. 20070155658 (e.g., a melamine derivative such as 2,4,6-Triguanidino Traizine and 2,4,6-Tramidosarcocyl Melamine, a polyarginine polypeptide, and a polypeptide including alternating glutamine and asparagine residues).

The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients disclosed herein and they include liposomes and microspheres. Examples of delivery systems useful in delivering the DDIT4 dsRNA molecules disclosed herein include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

In a particular embodiment, the administration comprises transtympanic administration. In another embodiment the administration comprises topical or local administration. The compounds are administered as eardrops, ear cream, ear ointment, foam, mousse or any of the above in combination with a delivery device. Implants of the compounds are also useful. Liquid forms are prepared as drops. The liquid compositions include aqueous solutions, with and without organic co-solvents, aqueous or oil suspensions, emulsions with edible oils, as well as similar pharmaceutical vehicles. These compositions may also be injected transtympanically. Eardrops may also be referred to as otic drops or aural drops. In a preferred embodiment, the ear drops remain in the ear canal for about 30 min in order to prevent leakage of the drops out of the canal. It is thus preferable that the subject receiving the drops keep his head on the side with the treated ear facing upward to prevent leakage of the drop out of the canal.

Methods for the delivery of nucleic acid molecules are described in Akhtar et al., Trends Cell Bio., 2: 139 (1992); Delivery Strategies for Antisense Oligonucleotide Therapeutics, ed. Akhtar, (1995), Maurer et al., Mol. Membr. Biol., 16: 129-140 (1999); Hofland and Huang, Handb. Exp. Pharmacol., 137: 165-192 (1999); and Lee et al., ACS Symp. Ser., 752: 184-192 (2000); U.S. Pat. Nos. 6,395,713; 6,235,310; 5,225,182; 5,169,383; 5,167,616; 4,959217; 4,925,678; 4,487,603; and 4,486,194 and Sullivan et al., PCT WO 94/02595; PCT WO 00/03683 and PCT WO 02/08754; and U.S. Patent Application Publication No. 2003077829. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see e.g., Gonzalez et al., Bioconjugate Chem., 10: 1068-1074 (1999); Wang et al., International PCT publication Nos. WO 03/47518 and WO 03/46185), poly(lactic-co-glycolic)acid (PLGA) and PLCA microspheres (see for example U.S. Pat. No. 6,447,796 and U.S. Application Publication No. 2002130430), biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules described herein, whether intravitreal, subcutaneous, transtympanic, intramuscular, or intradermal, can take place using standard needle and syringe methodologies, or by needle-free technologies such as those described in Conry et al., Clin. Cancer Res., 5: 2330-2337 (1999) and Barry et al., International PCT Publication No. WO 99/31262. The DDIT4 dsRNA molecules disclosed herein can be used as pharmaceutical agents. Pharmaceutical agents prevent, modulate the occurrence, or treat or alleviate a symptom to some extent (preferably all of the symptoms) of a disease state in a subject. In one specific embodiment, topical and transdermal formulations may be selected.

The dsRNA molecules or pharmaceutical compositions disclosed herein are administered and dosed in accordance with good medical practice, taking into account the clinical condition of the individual subject, the disease to be treated, the site and method of administration, scheduling of administration, patient age, sex, body weight and other factors known to medical practitioners.

In another embodiment the administration comprises topical or local administration such as via eye drops, eardrops or ointment.

Nucleic acid molecules may be complexed with cationic lipids, packaged within liposomes, or otherwise delivered to target cells or tissues. The nucleic acid or nucleic acid complexes can be locally administered to relevant tissues ex vivo, or in vivo through direct dermal application, transdermal application, or injection, with or without their incorporation in biopolymers.

Delivery systems may include surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011).

Nucleic acid molecules may be formulated or complexed with polyethylenimine (e.g., linear or branched PEI) and/or polyethylenimine derivatives, including for example polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives, grafted PEIs such as galactose PEI, cholesterol PEI, antibody derivatized PEI, and polyethylene glycol PEI (PEG-PEI) derivatives thereof (see for example Ogris et al., 2001, AAPA PharmSci, 3, 1-11; Furgeson et al., 2003, Bioconjugate Chem., 14, 840-847; Kunath et al., 2002, Pharmaceutical Research, 19, 810-817; Choi et al., 2001, Bull. Korean Chem. Soc., 22, 46-52; Bettinger et al., 1999, Bioconjugate Chem., 10, 558-561; Peterson et al., 2002, Bioconjugate Chem., 13, 845-854; Erbacher et al., 1999, Journal of Gene Medicine Preprint, 1, 1-18; Godbey et al., 1999., PNAS USA, 96, 5177-5181; Godbey et al., 1999, Journal of Controlled Release, 60, 149-160; Diebold et al., 1999, Journal of Biological Chemistry, 274, 19087-19094; Thomas and Klibanov, 2002, PNAS USA, 99, 14640-14645; Sagara, U.S. Pat. No. 6,586,524 and US Patent Application Publication No. 20030077829).

Nucleic acid molecules may be complexed with membrane disruptive agents such as those described in U.S. Patent Application Publication No. 20010007666. The membrane disruptive agent or agents and the nucleic acid molecule may also be complexed with a cationic lipid or helper lipid molecule, such as those lipids described in U.S. Pat. No. 6,235,310.

Nucleic acid molecules disclosed herein may be administered to the central nervous system (CNS) or peripheral nervous system (PNS). Experiments have demonstrated the efficient in vivo uptake of nucleic acids by neurons. See e.g., Sommer et al., 1998, Antisense Nuc. Acid Drug Dev., 8, 75; Epa et al., 2000, Antisense Nuc. Acid Drug Dev., 10, 469; Broaddus et al., 1998, J. Neurosurg., 88(4), 734; Karle et al., 1997, Eur. J. Pharmacol., 340(2/3), 153; Bannai et al., 1998, Brain Research, 784(1,2), 304; Rajakumar et al., 1997, Synapse, 26(3), 199; Wu-pong et al., 1999, BioPharm, 12(1), 32; Bannai et al., 1998, Brain Res. Protoc., 3(1), 83; and Simantov et al., 1996, Neuroscience, 74(1), 39. Nucleic acid molecules are therefore amenable to delivery to and uptake by cells in the CNS and/or PNS, e.g. neurons, macrophages, white matter axons and endothelial cells.

Delivery systems may include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer. Non-limiting examples of liposomes which can be used with the DDIT4 molecules include the following: (1) CellFectin, 1:1.5 (M/M) liposome formulation of the cationic lipid N,NI,NII,NIII-tetramethyl-N,NI, NII,NIII-tetrapalmit-y-spermine and dioleoyl phosphatidylethanolamine (DOPE) (GIBCO BRL); (2) Cytofectin GSV, 2:1 (M/M) liposome formulation of a cationic lipid and DOPE (Glen Research); (3) DOTAP (N-[1-(2,3-dioleoyloxy)-N,N,N-tri-methyl-ammoniummethylsulfate) (Boehringer Manheim); and (4) Lipofectamine, 3:1 (M/M) liposome formulation of the polycationic lipid DOSPA, the neutral lipid DOPE (GIBCO BRL) and Di-Alkylated Amino Acid (DiLA2).

Delivery systems may include patches, tablets, suppositories, pessaries, gels, aqueous and nonaqueous solutions, lotions and creams, and can contain excipients such as solubilizers and enhancers (e.g., propylene glycol, bile salts and amino acids), and other vehicles (e.g., polyethylene glycol, glycerol, fatty acid esters and derivatives, and hydrophilic polymers such as hydroxypropylmethylcellulose and hyaluronic acid).

Nucleic acid molecules may include a bioconjugate, for example a nucleic acid conjugate as described in Vargeese et al., U.S. Ser. No. 10/427,160; U.S. Pat. Nos. 6,528,631; 6,335,434; 6,235,886; 6,153,737; 5,214,136; 5,138,045.

Compositions, methods and kits disclosed herein may include an expression vector that includes a nucleic acid sequence encoding at least one nucleic acid molecule described herein in a manner that allows expression of the nucleic acid molecule. Methods of introducing nucleic acid molecules or one or more vectors capable of expressing the strands of dsRNA into the environment of the cell will depend on the type of cell and the make up of its environment. The nucleic acid molecule or the vector construct may be directly introduced into the cell (i.e., intracellularly); or introduced extracellularly into a cavity, interstitial space, into the circulation of an organism, introduced orally, or may be introduced by bathing an organism or a cell in a solution containing dsRNA. The cell is preferably a mammalian cell; more preferably a human cell. The nucleic acid molecule of the expression vector can include a sense region and an antisense region. The antisense region can include a sequence complementary to a RNA or DNA sequence encoding DDIT4, and the sense region can include a sequence complementary to the antisense region. The nucleic acid molecule can include two distinct strands having complementary sense and antisense regions. The nucleic acid molecule can include a single strand having complementary sense and antisense regions.

Nucleic acid molecules that interact with target RNA molecules and down-regulate gene encoding target RNA molecules (e.g., DDIT4 mRNA, SEQ ID NO:1) may be expressed from transcription units inserted into DNA or RNA vectors. Recombinant vectors can be DNA plasmids or viral vectors. Nucleic acid molecule expressing viral vectors can be constructed based on, but not limited to, adeno-associated virus, retrovirus, adenovirus, or alphavirus. The recombinant vectors capable of expressing the nucleic acid molecules can be delivered as described herein, and persist in target cells. Alternatively, viral vectors can be used that provide for transient expression of nucleic acid molecules. Such vectors can be repeatedly administered as necessary. Once expressed, the nucleic acid molecules bind and down-regulate gene function or expression, e.g., via RNA interference (RNAi). Delivery of nucleic acid molecule expressing vectors can be systemic, such as by intravenous or intramuscular administration, by local administration, by administration to target cells ex-planted from a subject followed by reintroduction into the subject, or by any other means that would allow for introduction into the desired target cell.

Expression vectors may include a nucleic acid sequence encoding at least one nucleic acid molecule disclosed herein, in a manner which allows expression of the nucleic acid molecule. For example, the vector may contain sequence(s) encoding both strands of a nucleic acid molecule that include a duplex. The vector can also contain sequence(s) encoding a single nucleic acid molecule that is self-complementary and thus forms a nucleic acid molecule. Non-limiting examples of such expression vectors are described in Paul et al., 2002, Nature Biotechnology, 19, 505; Miyagishi and Taira, 2002, Nature Biotechnology, 19, 497; Lee et al., 2002, Nature Biotechnology, 19, 500. Expression vectors may also be included in a mammalian (e.g., human) cell.

An expression vector may encode one or both strands of a nucleic acid duplex, or a single self-complementary strand that self hybridizes into a nucleic acid duplex. The nucleic acid sequences encoding nucleic acid molecules can be operably linked in a manner that allows expression of the nucleic acid molecule (see for example Paul et al., 2002, Nature Biotechnology, 19, 505; Miyagishi and Taira, 2002, Nature Biotechnology, 19, 497; Lee et al., 2002, Nature Biotechnology, 19, 500).

An expression vector may include one or more of the following: a) a transcription initiation region (e.g., eukaryotic pol I, II or III initiation region); b) a transcription termination region (e.g., eukaryotic pol I, II or III termination region); c) an intron and d) a nucleic acid sequence encoding at least one of the nucleic acid molecules, wherein said sequence is operably linked to the initiation region and the termination region in a manner that allows expression and/or delivery of the nucleic acid molecule. The vector can optionally include an open reading frame (ORF) for a protein operably linked on the 5'-side or the 3'-side of the sequence encoding the nucleic acid molecule; and/or an intron (intervening sequences).

A viral construct packaged into a viral particle would accomplish both efficient introduction of an expression construct into the cell and transcription of dsRNA construct encoded by the expression construct.

Methods for oral introduction include direct mixing of a dsRNA with food of the organism, as well as engineered approaches in which a species that is used as food is engineered to express an RNA, then fed to the organism to be affected. Physical methods may be employed to introduce a nucleic acid molecule solution into the cell. Physical methods of introducing nucleic acids include injection of a solution containing the nucleic acid molecule, bombardment by particles covered by the nucleic acid molecule, soaking the cell or organism in a solution of the dsRNA, or electroporation of cell membranes in the presence of the nucleic acid molecule. In one embodiment provided herein is a cell comprising a nucleic acid molecule disclosed herein.

Other methods known in the art for introducing nucleic acids to cells may be used, such as chemical mediated transport, such as calcium phosphate, and the like. Thus the nucleic acid molecules may be introduced along with components that perform one or more of the following activities: enhance RNA uptake by the cell, promote annealing of the duplex strands, stabilize the annealed strands, or other-wise increase inhibition/down-regulation of DDIT4.

Polymeric nanocapsules or microcapsules facilitate transport and release of the encapsulated or bound dsRNA into the cell. They include polymeric and monomeric materials, especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Nucleic acid molecules may be formulated as a microemulsion. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Delivery formulations can include water soluble degradable crosslinked polymers that include one or more degradable crosslinking lipid moiety, one or more PEI moiety, and/or one or more mPEG (methyl ether derivative of PEG (methoxypoly (ethylene glycol)).

Dosages

The useful dosage to be administered and the particular mode of administration will vary depending upon such factors as the cell type, or for in vivo use, the age, weight and the particular animal and region thereof to be treated, the particular nucleic acid and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art.

Suitable amounts of nucleic acid molecules may be introduced and these amounts can be empirically determined using standard methods. Effective concentrations of individual nucleic acid molecule species in the environment of a cell may be about 1 femtomolar, about 50 femtomolar, 100 femtomolar, 1 picomolar, 1.5 picomolar, 2.5 picomolar, 5 picomolar, 10 picomolar, 25 picomolar, 50 picomolar, 100 picomolar, 500 picomolar, 1 nanomolar, 2.5 nanomolar, 5 nanomolar, 10 nanomolar, 25 nanomolar, 50 nanomolar, 100 nanomolar, 500 nanomolar, 1 micromolar, 2.5 micromolar, 5 micromolar, 10 micromolar, 100 micromolar or more.

In general, the active dose of nucleic acid compound for humans is in the range of from 1 ng/kg to about 20-100 milligrams per kilogram (mg/kg) body weight of the recipient per day, preferably about 0.01 mg to about 2-10 mg/kg body weight of the recipient per day, in a regimen of a single dose, a one dose per day or twice or three or more times per day for a period of 1-4 weeks or longer. A suitable dosage unit of nucleic acid molecules may be in the range of 0.001 to 0.25 milligrams per kilogram body weight of the recipient per day, or in the range of 0.01 to 20 micrograms per kilogram body weight per day, or in the range of 0.01 to 10 micrograms per kilogram body weight per day, or in the range of 0.10 to 5 micrograms per kilogram body weight per day, or in the range of 0.1 to 2.5 micrograms per kilogram body weight per day. Dosage may be from 0.01 ug to 1 g per kg of body weight (e.g., 0.1 ug, 0.25 ug, 0.5 ug, 0.75 ug, 1 ug, 2.5 ug, 5 ug, 10 ug, 25 ug, 50 ug, 100 ug, 250 ug, 500 ug, 1 mg, 2.5 mg, 5 mg, 10 mg, 25 mg, 50 mg, 100 mg, 250 mg, or 500 mg per kg of body weight).

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depends upon the host treated and the particular mode of administration. Dosage unit forms generally contain between from about 1 mg to about 500 mg of an active ingredient.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

Pharmaceutical compositions that include the nucleic acid molecule disclosed herein may be administered once daily (QD), twice a day (bid), three times a day (tid), four times a day (qid), or at any interval and for any duration that is medically appropriate. However, the therapeutic agent may also be dosed in dosage units containing two, three, four, five, six or more sub-doses administered at appropriate intervals throughout the day. In that case, the nucleic acid molecules contained in each sub-dose may be correspondingly smaller in order to achieve the total daily dosage unit. The dosage unit can also be compounded for a single dose over several days, e.g., using a conventional sustained release formulation which provides sustained and consistent release of the dsRNA over a several day period. Sustained release formulations are well known in the art. The dosage unit may contain a corresponding multiple of the daily dose. The composition can be compounded in such a way that the sum of the multiple units of a nucleic acid together contain a sufficient dose.

Pharmaceutical Compositions, Kits, and Containers

Also provided are compositions, kits, containers and formulations that include a nucleic acid molecule (e.g., a dsRNA molecule) as provided herein for down-regulating expression of DDIT4 for administering or distributing the nucleic acid molecule to a patient. A kit may include at least one container and at least one label. Suitable containers include, for example, bottles, vials, syringes, and test tubes. The containers can be formed from a variety of materials such as glass, metal or plastic. The container can include nucleic acid sequence(s), and any other component required for relevant laboratory, prognostic, diagnostic, prophylactic and therapeutic purposes. Indications and/or directions for such uses can be included on or with such container, as can reagents and other compositions or tools used for these purposes.

The container can alternatively hold a composition that is effective for treating, diagnosis, prognosing or prophylaxing a condition and can have a sterile access port (for example the container can be an intravenous solution bag or a vial having a stopper pierceable by a hypodermic injection needle). The active agent in the composition preferably comprise a nucleic acid molecule capable of specifically binding DDIT4 mRNA and/or down-regulating the function DDIT4.

A kit may further include a second container that includes a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

Federal law requires that the use of pharmaceutical compositions in the therapy of humans be approved by an agency of the Federal government. In the United States, enforcement is the responsibility of the Food and Drug Administration, which issues appropriate regulations for securing such approval, detailed in 21 U.S.C. §301-392. Regulation for biologic material, including products made from the tissues of animals is provided under 42 U.S.C. §262. Similar approval is required by most foreign countries. Regulations vary from country to country, but individual procedures are well known to those in the art and the compositions and methods provided herein preferably comply accordingly.

As such, compositions, kits and methods disclosed herein may include packaging a nucleic acid molecule disclosed herein that includes a label or package insert. The label may include indications for use of the nucleic acid molecules such as use for treatment or prevention of diseases, disorders, injuries and conditions disclosed herein. The label may include indications for use of the nucleic acid molecules such as use for treatment or prevention of attenuation of neuronal degeneration. Neuronal degeneration includes for example degeneration of the optic nerve, auditory nerve, (also known as the vestibulocochlear nerve or acoustic nerve); the hair cells of the inner ear that transmit information to the brain via the auditory nerve, which consists of the cochlear nerve, and the vestibular nerve, and emerges from the medulla oblongata and enters the inner skull via the internal acoustic meatus (or internal auditory meatus) in the temporal bone, along with the facial nerve. The label may include indications for use of the nucleic acid molecules such as use for treatment or prevention of any other disease or conditions that are related to or will respond to the levels of DDIT4 in a cell or tissue, alone or in combination with other therapies. A label may include an indication for use in reducing and/or down-regulating expression of DDIT4. A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

Those skilled in the art will recognize that other treatments, drugs and therapies known in the art can be readily combined with the nucleic acid molecules herein (e.g. dsNA molecules) and are hence contemplated herein.

Methods of Treatment

In another aspect, provided herein are methods for the treatment of a subject in need of treatment for a disease or disorder associated with the abnormal or abberrant expression of DDIT4, comprising administering to the subject an amount a molecule disclosed herein, which reduces, down regulates or inhibits expression of DDIT4.

In one embodiment, nucleic acid molecules may be used to down-regulate or inhibit the expression of DDIT4 and/or DDIT4 proteins arising from DDIT 4 and/or haplotype polymorphisms that are associated with a disease or condition, (e.g., neurodegeneration). Analysis of DDIT 4 and/or DDIT4 genes, and/or protein or RNA levels can be used to identify subjects with such polymorphisms or those subjects who are at risk of developing traits, conditions, or diseases described herein. These subjects are amenable to treatment, for example, treatment with nucleic acid molecules disclosed herein and any other composition useful in treating diseases related to DDIT4 and/or DDIT4 gene expression. As such, analysis of DDIT4 nd/or protein or RNA levels can be used to determine treatment type and the course of therapy in treating a subject. Monitoring of protein or RNA levels can be used to predict treatment outcome and to determine the efficacy of compounds and compositions that modulate the level and/or activity of certain genes and/or proteins associated with a trait, condition, or disease.

Provided herein is a method of inhibiting the expression of DDIT4 by at least 40%, preferably by 50%, 60% or 70%, more preferably by 75%, 80% or 90% as compared to a control comprising contacting a DDIT4 mRNA transcript with one or more of the molecules disclosed herein.

In one embodiment the compound inhibits the DDIT4 polypeptide, whereby the inhibition is selected from the group comprising inhibition of function (which is examined by, for example, an enzymatic assay or a binding assay with a known interactor of the native gene/polypeptide, inter alia), inhibition of protein (which is examined by, for example, Western blotting, ELISA or immuno-precipitation, inter alia) and inhibition of mRNA expression (which is examined by, for example, Northern blotting, quantitative RT-PCR, in-situ hybridization or microarray hybridization, inter alia).

In additional embodiments, provided is a method of treating a patient suffering from a disease accompanied by an elevated level of a mammalian DDIT4 gene, the method comprising administering to the patient a DDIT4 dsRNA molecule disclosed herein in a therapeutically effective dose thereby treating the patient.

Methods, molecules and compositions which inhibit a mammalian gene or polypeptide are discussed herein at length, and any of said molecules and/or compositions are beneficially employed in the treatment of a patient suffering from any of said conditions. It is to be explicitly understood that known compounds are excluded. Novel methods of treatment using known compounds and compositions fall within the scope of the disclosure.

Further provided is a process of preparing a pharmaceutical composition, which comprises:

providing one or more double stranded molecule disclosed herein; and admixing said molecule with a pharmaceutically acceptable carrier.

In a preferred embodiment, the molecule used in the preparation of a pharmaceutical composition is admixed with a carrier in a pharmaceutically effective dose. In a particular embodiment, the molecules disclosed herein may be conjugated to a steroid, vitamin or to a lipid or to another suitable molecule, e.g. to cholesterol.

Provided are compositions and methods for inhibition of DDIT4 expression by using small nucleic acid molecules as provided herein, such as short interfering nucleic acid (siNA), interfering RNA (RNAi), short interfering RNA (siRNA), double-stranded RNA (dsRNA), micro-RNA (miRNA), ssRNA (single stranded RNAi) and short hairpin RNA (shRNA) molecules capable of down-regulating DDIT4 gene expression, or of mediating RNA interference against DDIT4 gene expression.

In some embodiments, dsRNA specific for DDIT4 can be used in conjunction with other therapeutic agents and/or dsRNA specific for other molecular targets, such as, without being limited to various proapoptotic genes.

In preferred embodiments the subject being treated is a warm-blooded animal and, in particular, mammals including human.

"Treatment" refers to both therapeutic treatment and prophylactic or preventative measures, wherein the object is to prevent a disorder or reduce the symptoms of a disorder, for example, an eye disease or disorder, a hearing disorder or impairment (or balance impairment), or to prevent or reduce cell death or neuron degeneration associated with DDIT4 expression. Those in need of treatment include those already experiencing the disease or condition, those prone to having the disease or condition, and those in which the disease or condition is to be prevented. The DDIT4 dsRNA molecules disclosed herein are administered before, during or subsequent to the onset of the disease or condition.

Without being bound by theory, the disease or disorder may be due to apoptotic cell damage or loss.

In some embodiments combination therapy is preferred. Combination therapy is achieved by administering two or more agents (i.e. two or more dsRNA or at least one dsRNA and at least one another therapeutic agent) each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within one or several hours of each other or within one or several days of each other or within several weeks of each other. In some cases even longer intervals are possible. The two or more agents used in combination therapy may or may not be present within the patient's body at the same time. Combination therapy includes two or more administrations of one or more of the agents used in the combination. For example, if dsRNA1 and dsRNA2 (i.e. wherein dsRNA1 targets gene 1 and dsRNA2 targets gene 2) are used in a combination, one could administer them sequentially in any combination one or more times, e.g., in the order dsRNA1-dsRNA2, dsRNA2-dsRNA1, dsRNA1-dsRNA2-dsRNA1, dsRNA2-dsRNA1-dsRNA2, dsRNA1-dsRNA1-dsRNA2, dsRNA1-dsRNA2-dsRNA2 etc.

Details of certain indications in which the compounds disclosed herein are useful as therapeutics are described herein.

The invention has been described in an illustrative manner, and it is to be understood that the terminology used is intended to be in the nature of words of description rather than of limitation.

Obviously, many modifications and variations are possible in light of the above teachings. It is, therefore, to be understood that within the scope of the appended claims, the invention can be practiced otherwise than as specifically described.

Throughout this application, various publications, including United States Patents, are referenced by author and year and patents by number. The disclosures of these publications and patents and patent applications in their entireties are hereby incorporated by reference into this application in order to more fully describe the state of the art to which this invention pertains.

The present invention is illustrated in detail below with reference to examples, but is not to be construed as being limited thereto.

Citation of any document herein is not intended as an admission that such document is pertinent prior art, or considered material to the patentability of any claim of the present invention. Any statement as to content or a date of any document is based on the information available to applicant at the time of filing and does not constitute an admission as to the correctness of such a statement.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., Molecular cloning: A laboratory manual, Cold Springs Harbor Laboratory, New-York (1989, 1992), and in Ausubel et al., Current Protocols in Molecular Biology, John Wiley and Sons, Baltimore, Md. (1988), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out as in standard PCR Protocols: A Guide To Methods And Applications, Academic Press, San Diego, Calif. (1990). In situ PCR in combination with Flow Cytometry (FACS) can be used for detection of cells containing specific DNA and mRNA sequences (Testoni et al., Blood 1996, 87:3822.) Methods of performing RT-PCR are well known in the art.

Example 1

Identification of DDIT4 Sense Strands and Antisense Strands

Tables 1 and 2 herein below show preferred sense strands and corresponding antisense strands useful in generating dsRNA molecules

TABLE 1

| dsRNA Name | SEQ ID NO | Sense strand (5'>3') | SEQ ID NO | Antisense strand (5'>3') | length |
|---|---|---|---|---|---|
| DDIT4_41 | 3 | CCCUCAGUACUGUAGCAU | 12 | AUGCUACAGUACUGAGGG | 18 |
| DDIT4_43 | 4 | GGCAGCUAUCUUACAGAC | 13 | GUCUGUAAGAUAGCUGCC | 18 |
| DDIT4_46 | 5 | AGAGCUCGGACUGCGAGU | 14 | ACUCGCAGUCCGAGCUCU | 18 |
| DDIT4_55 | 6 | GGGUCUUCCAUCUAGAAC | 15 | GUUCUAGAUGGAAGACCC | 18 |
| DDIT4_59 | 7 | GGUGGAGACUAGAGGCAG | 16 | CUGCCUCUAGUCUCCACC | 18 |
| DDIT4_60 | 8 | CCUCCAAGACAGAGACGA | 17 | UCGUCUCUGUCUUGGAGG | 18 |
| DDIT4_61 | 9 | GGAAGCUCAUUGAGUUGU | 18 | ACAACUCAAUGAGCUUCC | 18 |
| DDIT4_62 | 10 | GCAGCUGCGUUUAAGCCU | 19 | AGGCUUAAACGCAGCUGC | 18 |
| DDIT4_63 | 11 | CAGUACUGUAGCAUGAAA | 20 | UUUCAUGCUACAGUACUG | 18 |

TABLE 2

| dsRNA Name | SEQ ID NO | Sense strand (5'>3') | SEQ ID NO | Antisense strand (5'>3') | length |
|---|---|---|---|---|---|
| DIT4_41a | 21 | CCCUCAGUACUGUAGCAUA | 30 | UAUGCUACAGUACUGAGGG | 18 + 1 |
| DDIT4_43a | 22 | GGCAGCUAUCUUACAGACA | 31 | UGUCUGUAAGAUAGCUGCC | 18 + 1 |

TABLE 2-continued

| dsRNA Name | SEQ ID NO | Sense strand (5'>3') | SEQ ID NO | Antisense strand (5'>3') | length |
|---|---|---|---|---|---|
| DDIT4_46a | 23 | AGAGCUCGGACUGCGAGUA | 32 | UACUCGCAGUCCGAGCUCU | 18 + 1 |
| DDIT4_55a | 24 | GGGUCUUCCAUCUAGAACA | 33 | UGUUCUAGAUGGAAGACCC | 18 + 1 |
| DDIT4_59a | 25 | GGUGGAGACUAGAGGCAGA | 34 | UCUGCCUCUAGUCUCCACC | 18 + 1 |
| DDIT4_60a | 26 | CCUCCAAGACAGAGACGAA | 35 | UUCGUCUCUGUCUUGGAGG | 18 + 1 |
| DDIT4_61a | 27 | GGAAGCUCAUUGAGUUGUA | 36 | UACAACUCAAUGAGCUUCC | 18 + 1 |
| DDIT4_62a | 28 | GCAGCUGCGUUUAAGCCUA | 37 | UAGGCUUAAACGCAGCUGC | 18 + 1 |
| DDIT4_63u | 29 | CAGUACUGUAGCAUGAAAU | 38 | AUUUCAUGCUACAGUACUG | 18 + 1 |

In SEQ ID NO: 30, 31, 34, 36 the "U" in position 1 of the AS is mismatched to "G" in the target mRNA. In SEQ ID NO:32, 35 "U" in position 1 of the AS is mismatched to "C" in the target mRNA. In SEQ ID NO: 33 and 37 the "U" in position 1 of the AS is mismatched to "U" in the target mRNA. In SEQ ID NO:38 "A" in position 1 of the AS is mismatched to "C" in the target mRNA.

Table 3 provides DDIT4 molecules disclosed herein.

TABLE 3

| dsRNA Name | SEQ ID NO | Sense strand (5'>3') | SEQ ID NO | Antisense strand (5'>3') | length |
|---|---|---|---|---|---|
| DDIT4_32 | 39 | CCUCAGUACUGUAGCAUGA | 42 | UCAUGCUACAGUACUGAGG | 19 |
| DDIT4_34 | 40 | CUCAGUACUGUAGCAUGAA | 43 | UUCAUGCUACAGUACUGAG | 19 |
| DDIT4_2 | 41 | UACUGUAGCAUGAAACAAA | 44 | UUUGUUUCAUGCUACAGUA | 19 |
| DDIT4_1 | 45 | GUGCCAACCUGAUGCAGCU | 46 | AGCUGCAUCAGGUUGGCAC | |

Table 4 provides DDIT4 compounds which utilize the oligonucleotide sequences and chemical modifications disclosed herein.

TABLE 4

| Name | Sense 5->3 | AntiSense 5->3 |
|---|---|---|
| DDIT4_41_S2012 | rC; rC; rC; rU; mC; rA; rG; mU; rA; rC; mU; rG; mU; rA; rG; mC; rA; mU; rA; zc3p | mU; rA; mU; rG; rC; rU2p; rA; mC; rA; rG; mU; rA; rC; rU; mG; rA; rG; rG; rG; zc3p; zc3p$ |
| DDIT4_41_S2013 | rC; rC; rC; rU; rC; rA; rG; rU; rA; rC; rU; rG; rU; rA; rG; mC; rA; mU; rA; zc3p | mU; rA; mU; rG; rC; rU2p; rA; mC; rA; rG; mU; rA; rC; rU; mG; rA; rG; rG; rG; zc3p; zc3p$ |
| DDIT4_41_S2071 (inverted deoxyabasic cap) | zidB; rC; rC; rC; rU; rC; rA; rG; rU; rA; rC; rU; rG; rU; rA; rG; mC; rA; mU; rA; zc3p | mU; rA; mU; rG; rC; rU2p; rA; mC; rA; rG; mU; rA; rC; rU; mG; rA; rG; rG; rG; zc3p; zc3p$ |
| DDIT4_41_S2072 (amino C6 cap) | zc6Np; rC; rC; rC; rU; rC; rA; rG; rU; rA; rC; rU; rG; rU; rA; rG; mC; rA; mU; rA; zc3p | mU; rA; mU; rG; rC; rU2p; rA; mC; rA; rG; mU; rA; rC; rU; mG; rA; rG; rG; rG; zc3p; zc3p$ |
| DDIT4_41_S2073 (THNB cap) | zTHNBc6p; rC; rC; rC; rU; rC; rA; rG; rU; rA; rC; rU; rG; rU; rA; rG; mC; rA; mU; rA; zc3p | mU; rA; mU; rG; rC; rU2p; rA; mC; rA; rG; mU; rA; rC; rU; mG; rA; rG; rG; rG; zc3p; zc3p$ |
| DDIT4_41_S2014 | rC; rC; rC; rU; rC; rA; rG; rU; rA; rC; rU; rG; rU; rA; rG2p; rC2p; rA2p; rU2p; rA2p; zc3p | mU; rA; mU; rG; rC; rU2p; rA; mC; rA; rG; mU; rA; rC; rU; mG; rA; rG; rG; rG; zc3p; zc3p$ |
| DDIT4_41_S2015 | rC; rC; rC; rU; mC; rA; rG; mU; rA; rC; mU; rG; mU; rA; rG; mC; rA; mU; rA; zc3p | mU; rA; mU; rG; rC; rU2p; rA; mC; rA; rG; rU; rA; rC; rU; mG; rA; rG; rG; rG; zc3p; zc3p$ |
| DDIT4_41_S2016 | rC; rC; rC; rU; rC; rA; rG; rU; rA; rC; rU; rG; rU; rA; rG; mC; rA; mU; rA; zc3p | mU; rA; mU; rG; rC; rU2p; rA; mC; rA; rG; rU; rA; rC; mU; rG; rA; rG; rG; rG; zc3p; zc3p$ |
| DDIT4_41_S2017 | rC; rC; rC; rU; rC; rA; rG; rU; rA; rC; rU; rG; rU; rA; rG2p; rC2p; rA2p; rU2p; rA2p; zc3p | mU; rA; mU; rG; rC; rU2p; rA; mC; rA; rG; rU; rA; rC; rU; mG; rA; rG; rG; rG; zc3p; zc3p$ |
| DDIT4_2_S500 | rU; mA; rC; mU; rG; mU; rA; mG; rC; mA; rU; mG; rA; mA; rA; mC; rA; mA; rA | mU; rU; mU; rG; mU; rU; mU; rC; mA; rU; rC; mU; rA; mC; rA; mG; rU; mA |
| DDIT4_2_S2031 (inverted deoxyabasic cap) | zidB; mU; rA; rC; mU; rG; mU; rA; rG; mC; rA; mU; rG; rA; rA; mC; rA; rA; rA; zc3p | mU; rU; mU; rG; mU; rU; rU2p; mC; rA; mU; rG; rC; mU; rA; mC; rA; rG; mU; rA; zc3p; zc3p$ |
| DDIT4_2_S2032 | zidB; mU; rA; rC; mU; rG; mU; rA; rG; mC; rA; mU; rG; rA; rA; mC; rA; rA; rA; zc3p | mU; rU; mU; rG; mU; rU; rU2p; mC; rA; mU; rG; rC; mU; rA; mC; rA; rG; mU; rA; zc3p; zc3p$ |
| DDIT4_2_S2033 | zidB; mU; rA; rC; mU; rG; mU; rA; rG; mC; rA; mU; rG; rA; rA; mC; rA; rA; rA; zc3p | mU; rU; mU; rG; mU; rU; rU2p; rU; mC; rA; mU; rG; rC; mU; rA; mC; rA; rG; mU; rA; zc3p; zc3p$ |
| DDIT4_2_S2034 | zidB; mU; rA; rC; mU; rG; mU; rA; rG; rC; mA; rU; mG; rA; rA; rA; mC; rA; rA; rA; zc3p | mU; rU; mU; rG; mU; rU; rU2p; mC; rA; mU; rG; rC; mU; rA; mC; rA; rG; mU; rA; zc3p; zc3p$ |

TABLE 4-continued

| Name | Sense 5->3 | AntiSense 5->3 |
|---|---|---|
| DDIT4_2_S2035 | zidB; mU; rA; rC; mU; rG; mU; rA; rG; rC; mA; rU; mG; rA; rA; rA; mC; rA; rA; rA; zc3p | mU; rU; mU; rG; mU; rU; rU2p; mC; rA; rU; rG; rC; mU; rA; mC; rA; rG; mU; rA; zc3p; zc3p$ |
| DDIT4_2_S2036 | zidB; mU; rA; rC; mU; rG; mU; rA; rG; rC; mA; rU; mG; rA; rA; rA; mC; rA; rA; rA; zc3p | mU; rU; mU; rG; rU; rU2p; rU; mC; rA; rU; rG; rC; mU; rA; mC; rA; rG; mU; rA; zc3p; zc3p$ |
| DDIT4_63_S2008 | mC; rA; rG; mU; rA; rC; mU; rG; mU; rA; rG; mC; rA; mU; rG; rA; rA; rA; rU; zc3p | rA; rU; mU; rU; mC; rA; rU2p; rG; rC; mU; rA; mC; rA; rG; mU; rA; rC; mU; rG; zc3p; zc3p$ |
| DDIT4_63_S2009 | mC; rA; rG; mU; rA; rC; mU; rG; mU; rA; rG; mC; rA; mU; rG; rA; rA; rA; rU; zc3p | rA; rU; mU; rU; mC; rA; rU2p; rG; rC; rU; mA; rC; mA; rG; mU; rA; rC; mU; rG; zc3p; zc3p$ |
| DDIT4_63_S2010 | mC; rA; rG; rU; rA; rC; rU; rG; rU; rA; rG; rC; rA; rU; rG2p; rA2p; rA2p; rA2p; rU2p; zc3p | rA; rU; mU; rU; mC; rA; rU2p; rG; rC; mU; rA; mC; rA; rG; mU; rA; rC; mU; rG; zc3p; zc3p$ |
| DDIT4_63_S2011 | mC; rA; rG; rU; rA; rC; rU; rG; rU; rA; rG; rC; rA; rU; rG2p; rA2p; rA2p; rA2p; rU2p; zc3p | rA; rU; mU; rU; mC; rA; rU2p; rG; rC; rU; mA; rC; mA; rG; mU; rA; rC; mU; rG; zc3p; zc3p$ |
| DDIT4_1_S73 | rG; mU; rG; mC; rC; mA; rA; mC; rC; mU; rG; mA; rU; mG; rC; mA; rG; mC; rU$ | mA; rG; mC; rU; mG; rC; mA; rU; mC; rA; mG; rG; mU; rU; mG; rG; mC; rA; mC$ |
| DDIT4_1_S500 | rG; mU; rG; mC; rC; mA; rA; mC; rC; mU; rG; mA; rU; mG; rC; mA; rG; mC; rU | mA; rG; mC; rU; mG; rC; mA; rU; mC; rA; mG; rG; mU; rU; mG; rG; mC; rA; mC |

Table 5 provides the key to the chemical modifications shown in Table 4.

TABLE 5

| | Modification Description |
|---|---|
| $ | No 3' Phosphate |
| 3mN2p | 3'-O-methyl ribo-nucleotide-2'-phosphate (3'OMe on 2'5' linked ribonuc) |
| 5med | 5'-O-methyl deoxy-nucleotide 3'-phosphate |
| d | deoxyribose-5'-phosphate |
| d | deoxyUridine |
| dB | abasic deoxyribose-3'-phosphate (Tetrahydrofuran) |
| dC(C6N) | Amino-Modifier-C6-dC (dC-derivative; Glen Research) |
| dC(N4al) | deoxy Cytidine N4 Amino linker (ChemGene) |
| dNpac | deoxyribonucleotide-3' phosphonoacetate (PACE) |
| dT(C2N) | Amino-Modifier-C2-dT (dU-derivative; Glen Research) |
| ena | 2'-N,4'-C-Ethylene-bridged nucleosides |
| FITC | Fluorescein isothiocyanate (fluorescent dye) |
| idB | internal_Inverted abasic deoxyribose-5'-phosphate |
| Ld | Mirror deoxy-nucleotide (mirror image DNA) |
| lna | Locked deoxy Nucleic Acid (deoxy) |
| Lr | mirror image RNA |
| m | 2'-O-methyl ribo-nucleotide-3'-phosphate (mA, mC, mG, mU) |
| m5r | 5-Methyl-ribonucleotide (cytidine/uridine) |
| mNpeth | 2'-O-methylnucleotide-3'-ethoxyphosphate |
| mNps | Phosphorothioated 2'-O-methyl base |
| NPr | Ribonucleotide-N3'—P5' |
| p | 5'- Phosphate |
| psiU | Pseudouridine |
| ptd | Pyrazolo-triazine deoxyAdenosine, C-C nucleoside |
| rN2p | ribo-nucleotide-2'-phosphate (2'5' linked) |
| rNps | Phosphorothioated RNA base |
| s | 5' phosphorothioate = non-cleavable Pi |
| tna | Threose Nucleic Acid |
| X | blank |
| y8Oxo-dG | replace with 8-Oxo-dG (Glen Research: 10-1028-xx) |
| yc3p | replace with 3-Hydroxypropane-1-phosphate |
| ydA | replace with deoxyriboAdenosine-3'-phosphate; |
| ydT | replace with deoxyriboThymidine-3'-phosphate; |
| ydU | replace with deoxyUridine |
| yLdA | replace with L-deoxyriboAdenosine-3'-phosphate |
| yLdC | replace with L-deoxyriboCytidine-3'-phosphate |
| yLdG | replace with L-deoxyriboGuanosine-3'-phosphate |
| ymA | replace with 2'-O-methylAdenosine-3'-phosphate; |
| ymC | replace with 2'-O-methylCytidine-3'-phosphate; |
| ymU | replace with 2'-O-methylUridine-3'-phosphate; |
| yrA | replace with riboAdenosine-3'-phosphate; |
| yrC | replace with riboCytidine-3'-phosphate; |
| yrG | replace with riboGuanosine-3'-phosphate; |
| yrU | replace with riboUridine-3'-phosphate; |
| yrU2p | replace with riboUridine-2'-phosphate |
| ytnaA | replace with tnaA |
| ytnaC | replace with tnaC |
| z(c12Np)2 | (C12-Amino-Pi)2-Symmetrical Doubler |
| z(c12p)2 | (C12-Pi)2-Symmetrical Doubler |
| z(c6Np)2 | (C6-Amino-Pi)2-Symmetrical Doubler |

TABLE 5-continued

| | Modification Description |
|---|---|
| zc12Np | Amino-C12-Phosphate |
| zc3p | (CH2)3-Pi = 3-Hydroxypropane-1-phosphate |
| zc3p; zc3p | (CH2)3-Pi x2; = 3-Hydroxypropane-1-phosphate; |
| zc3p; zc3p; zc3p | (CH2)3-Pi x3; = 3-Hydroxypropane-1-phosphate; |
| zc3p; zc3p; zcy3 | (CH2)3-Pi; (CH2)3-Pi; Cyanine Dye |
| zc3p; zc3ps | (CH2)3-Pi; (CH2)-3'phosphorotioate |
| zc3p; zcy3 | (CH2)3-Pi (=3-Hydroxypropane-1-phosphate); Cyanine Dye |
| zc3p; zrB | (CH2)3-Pi; ribo-Abasic-3'-Pi |
| zc3p; zrG | (CH2)3-Pi _rG |
| zc5Np | Amino-C5-Phosphate |
| zc6Np | Amino-C6-Phosphate |
| zc6Np; z(CH2CH2O)3p | NH2—C6-pi_(CH2CH2O)3-pi |
| zc6Np; z(CH2CH2O)6p | NH2—C6-pi_(CH2CH2O)6-pi |
| zc6Np; zc12p | NH2—C6-pi_(CH2)12-pi |
| zc6Np; zc6p | NH2—C6-pi_(CH2)6-pi |
| zc6Np; zrC; zrA | Amino-C6-Phosphate_rCrA |
| zcy3 | Cyanine fluorophore (covalently attached) |
| zcy3; zdT | Cy3_deoxy-Thymidine-3'-Pi covalently attached at 3' terminus |
| zcy5 | Cyanine Dye (Violet Excitation) |
| zdB; zdB | abasic deoxyribose-3'-phosphate x2 |
| zdC(C6N) | Amino-Modifier-C6-dC (dC-derivative; Glen Research) |
| zdC(C6N); zdC(C6N) | Amino-Modifier-C6-dC x2 (dC-derivative; Glen Research) |
| zdC(N4al) | deoxy Cytidine N4 Amino linker (ChemGenes) |
| zdT | deoxy-Thymidine-3'-Phosphate (dT) |
| zdT; zdT | dTdT overhang covalently attached at 3' |
| zdU | cap deoxyUridine |
| zidB | Inverted abasic deoxyribose-5'-phosphate; At 5' = 5'-5' idAb; At 3' = 3'-3' idAb |
| zidT | Inverted-Deoxy-Thymidine-5'-Phosphate |
| ziLd | Inverted L-DNA covalently attached at terminus |
| zirB | Inverted abasic ribose-5'-phosphate |
| zirB; zirB | Inverted abasic ribose-5'-phosphate x2 |
| zirB; zrC; zrA | Inverted abasic ribose-3'-phosphate_rCrA |
| zLdA | L-deoxyriboAdenosine-3'-phosphate |
| zLdC | L-deoxyriboCytidine-3'-phosphate |
| zLdG | L-deoxyriboGuanosine-3'-phosphate |
| zLdT | L-deoxyriboThymidine-3'-phosphate |
| zmC | 2'-O-methylCytidine-3'-phosphate |
| zmU | 2'-O-methyluridine-3'-ethoxyphosphate |
| zmU; zmU | mUmU |
| zRA; zc12Np | Retinoic acid_C12-Amino-Pi |
| zrA; zrG | rArG attached at terminus |
| zRAp | Retinoic acid |
| zRAp; z(CH2CH2O)3p | Retinoic acid-pi_(CH2CH2O)3-pi |
| zRAp; z(CH2CH2O)6p | Retinoic acid-pi_(CH2CH2O)6-pi |
| zRAp; zc12p | Retinoic acid-pi_(CH2)12-Pi |
| zRAp; zc6p | Retinoic acid-pi_(CH2)6-pi |
| zrB; zrB | abasic ribose-3'-phosphate x2 |
| zrC; zrA | rC; rA |
| zrU; zrG | rUrG |
| zrU; zrU | rUrU |
| zVEp | Vitamin E-pi |
| zVEp; z(CH2CH2O)3p | Vitamin E-pi_(CH2CH2O)3-pi |
| zVEp; zc12p | Vitamin E-pi_(CH2)12-pi |
| zVEp; zc6p | Vitamin E-pi_(CH2)6-pi |
| z | Moiety (nucleotide or non-nucleotide) covalently attached to terminus |

In Vitro Testing of dsRNA Molecules

About 1.5-2×105 tested cells (HeLa cells and/or 293T cells and or Be2C cells for dsRNA molecules and NRK52 (normal rat kidney proximal tubule cells) cells and/or NMuMG cells (mouse mammary epithelial cell line) for siRNA targeting the rat/mouse gene) were seeded per well in 6 wells plate (70-80% confluent).

24 hours later, cells were transfected with dsRNA molecules using the Lipofectamine™ 2000 reagent (Invitrogen) at final concentrations of 5 nM or 20 nM. The cells were incubated at 370 C in a CO2 incubator for 72 h.

As positive control for transfection, PTEN-Cy3 labeled dsRNA molecules were used. GFP dsRNA molecules were used as negative control for siRNA activity.

At 72 h after transfection, cells were harvested and RNA was extracted from cells. Transfection efficiency was tested by fluorescent microscopy.

The percent of inhibition of gene expression using specific preferred molecules was determined using qPCR analysis of a target gene in cells expressing the endogenous gene. FIGS. 1A-1F show knock downactivity of molecules disclosed herein. Results are residual activity (e.g. lower value, refers to higher knockdown).

Body Fluid/Cell Stability Assay

The modified compounds disclosed herein are tested for duplex stability in human, rat or mouse plasma or human, rat or mouse serum (to test in model system), or CSF (cerebrospinal fluid; human, mouse or rat), rat or rabbit vitreous fluid, orhuman cell extract, as follows:

For example: dsRNA molecules at final concentration of 7 uM are incubated at 370 C in 100% human serum (Sigma Cat# H4522). (siRNA stock 100 uM diluted in human serum 1:14.29 or human tissue extract from various tissue types.). Five ul (5 ul) are added to 15 ul 1.5×TBE-loading buffer at different time points (for example 0, 30 min, 1 h, 3 h, 6 h, 8 h, 10 h, 16 h and 24 h). Samples are immediately frozen in liquid nitrogen and are kept at −20° C.

Each sample is loaded onto a non-denaturing 20% acrylamide gel, prepared according to methods known in the art. The oligos are visualized with ethidium bromide under UV light.

Figure 2:
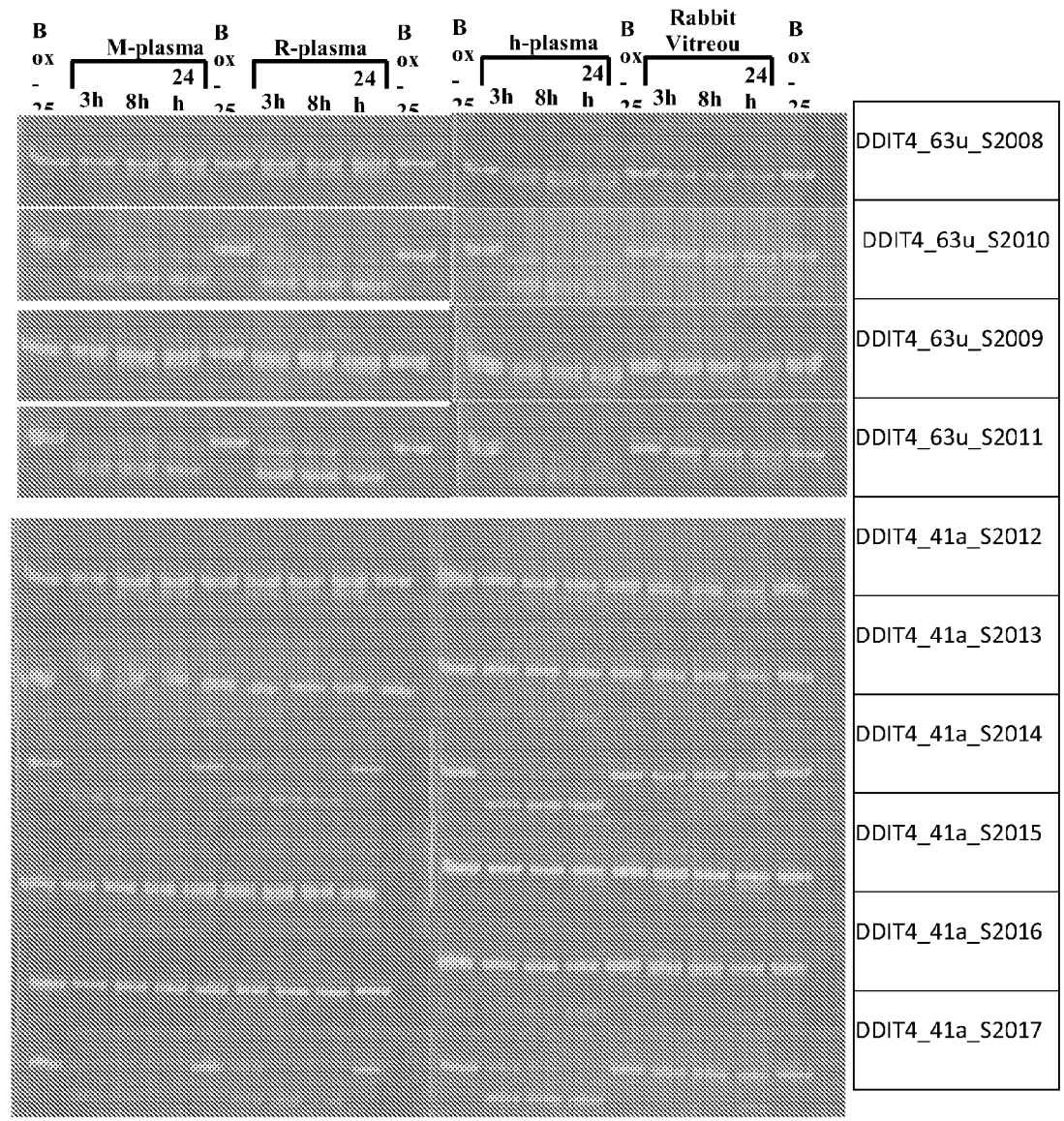
FIG. 2 shows stability of some of the dsRNA molecules disclosed herein in mouse plasma (M-plasma), rat plasma (R-plasma), human plasma (h-plasma) and rabbit vitreous fluid at 3 hr., 8 hr. and 24 hr. compared to 25 ng control dsRNA ("box"). DDIT4_63u_S2009, DDIT4_41a_S2013, _S2015, _S2016 are the most stable molecules in all bodily fluids. Ethidium bromide gel shown.
Figure 3A:
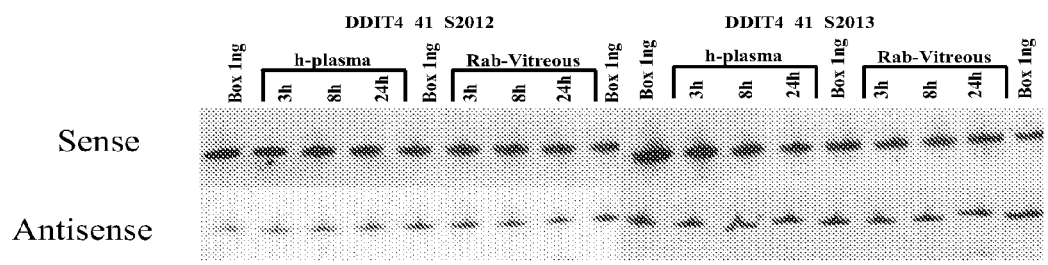
FIGS. 3A-3D show exposures of sense and antisense strand stability in various body fluid.
Figure 3B:
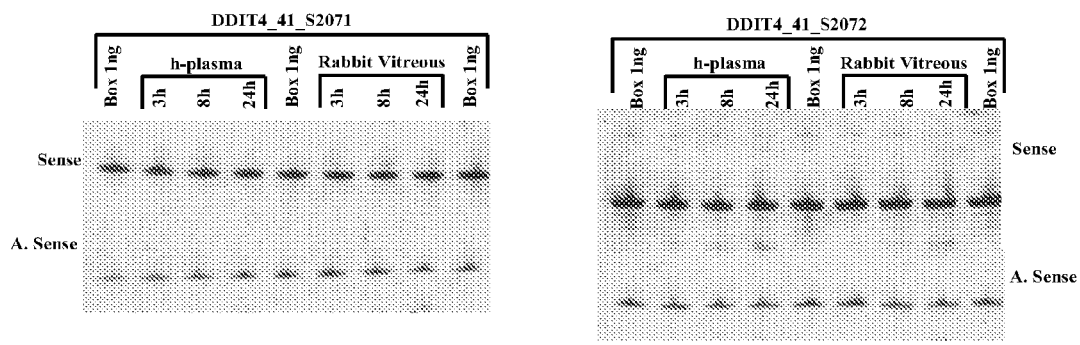
Figure 3C:
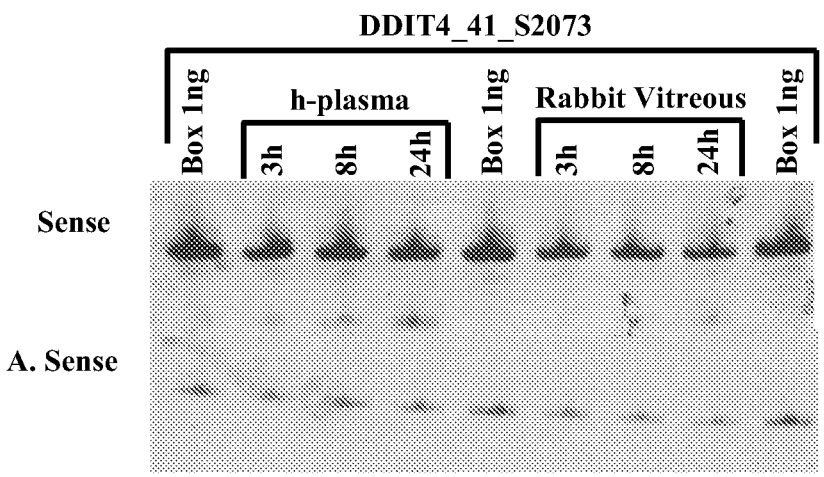
Figure 3D:
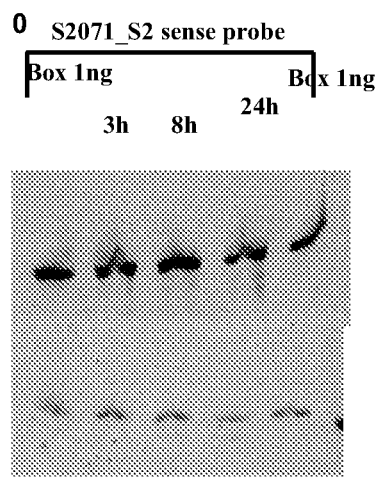

FIG. 2 shows stability of molecules disclosed herein.

Exonuclease Stability Assay

To study the stabilization effect of 3' non-nucleotide moieties on a nucleic acid molecule the sense strand, the antisense strand and the annealed dsRNA duplex are incubated in cytosolic extracts prepared from different cell types.

Extract: HCT116 cytosolic extract (12 mg/ml).

Extract buffer: 25 mM Hepes pH-7.3 at 37° C.; 8 mM MgCl; 150 mM NaCl with 1 mM DTT was added fresh immediately before use.

Method: 3.5 ml of test dsRNA (100 mM), were mixed with 46.5 ml contain 120 mg of HCT116 cytosolic extract. The 46.5 ml consists of 12 ml of HCT116 extract, and 34.5 ml of the extract buffer supplemented with DTT and protease inhibitors cocktail/100 (Calbiochem, setIII-539134). The final concentration of the siRNA in the incubation tube is 7 mM. The sample is incubated at 37° C., and at the indicated time point 5 ml are moved to fresh tube, mixed with 15 ml of 1×TBE-50% Glycerol loading buffer, and snap frozen in Liquid N2. The final concentration of the siRNA in the loading buffer is 1.75 mM (21 ng siRNA/ml). For analyses by native PAGE and EtBr staining 50 ng are loaded per lane. For Northern analyses ing of tested siRNA are loaded per lane.

Innate Immune Response to dsRNA Molecules:

Fresh human blood (at RT) is mixed at 1:1 ratio with sterile 0.9% NaCl at RT, and gently loaded (1:2 ratio) on Ficoll (Lymphoprep, Axis-Shield cat#1114547). Samples are centrifuged at RT (22° C., 800 g) in a swinging centrifuge for 30 minutes, washed with RPMI1640 medium and centrifuged (RT, 250 g) for 10 minutes. Cells are counted and seeded at final concentration of 1.5×106 cell/ml in growth medium (RPMI1640+10% FBS+2 mM L-glutamine+1% Pen-Strep) and incubated for 1 hour at 37° C. before dsRNA treatment. Cells are exposed to the test dsRNAs at different concentrations using the Lipofectamine™2000 reagent (Invitrogen) according to manufacturer's instructions and incubated at 37° C. in a 5% CO2 incubator for 24 hours.

As a positive control for IFN response, cells are treated with either poly(I:C), a synthetic analog of double strand RNA (dsRNA) which is a TLR3 ligand (InvivoGen Cat# tlrl-pic) at final concentrations of 0.25-5.0 μg/mL or to Thiazolaquinolone (CL075), a TLR 7/8 ligand (InvivoGen Cat# tlrl-c75) at final concentrations of 0.075-2 μg/mL. Cell treated with Lipofectamine™2000 reagent are used as negative (reference) control for IFN response.

At about 24 hours following incubation, cells are collected and supernatant is transferred to new tubes. Samples are frozen immediately in liquid nitrogen and secretion of IL-6 and TNF-α cytokines was tested using IL-6, DuoSet ELISA kit (R&D System DY2060), and TNF-α, DuoSet ELISA kit (R&D System DY210), according to manufacturer's instructions. RNA is extracted from the cell pellets and mRNA levels of human genes IFIT1 (interferon-induced protein with tetratricopeptide repeats 1) and MX1 (myxovirus (influenza virus) resistance 1, interferon-inducible protein p78) were measured by qPCR. Measured mRNA quantities are normalized to the mRNA quantity of the reference gene peptidylprolyl isomerase A (cyclophilin A; CycloA). Induction of IFN-signaling is evaluated by comparing the quantity of mRNA from IFIT1 and MX1 genes from treated cells, relative to their quantities non-treated cells. The qPCR results are those that passed QC standards, i.e. the value of the standard curve slope was in the interval [−4, −3], R2 >0.99, no primer dimers. Results that do not pass the QC requirements are disqualified from analysis.

In general, the dsRNAs having specific sequences that were selected for in vitro testing were specific for human and a second species such as rat or rabbit genes. Certain preferred chemically modified duplexes are set forth herein below and in Table 4, hereinabove.

| Duplex name | Sense strand/antisense strand (5' > 3') |
|---|---|
| DDIT4_41a_S2012 | rC; rC; rC; rU; mC; rA; rG; mU; rA; rC; mU; rG; mU; rA; rG; mC; rA; mU; rA; zc3p |
| | mU; rA; mU; rG; rC; rU2p; rA; mC; rA; rG; mU; rA; rC; rU; mG; rA; rG; rG; rG; zc3p; zc3p$ |
| DDIT4_41a_S2013 | rC; rC; rC; rU; rC; rA; rG; rU; rA; rC; rU; rG; rU; rA; rG; mC; rA; mU; rA; zc3p |
| | mU; rA; mU; rG; rC; rU2p; rA; mC; rA; rG; mU; rA; rC; rU; mG; rA; rG; rG; rG; zc3p; zc3p$ |

| Duplex name | Sense strand/antisense strand (5' > 3') |
|---|---|
| DDIT4_41a_S2071 (SEQ ID NOS: 21 and 30) inverted deoxyabasic on 5' sense strand | zidB; rC; rC; rC; rU; rC; rA; rG; rU; rA; rC; rU; rG; rU; rA; rG; mC; rA; mU; rA; zc3p<br>mU; rA; mU; rG; rC; rU2p; rA; mC; rA; rG; mU; rA; rC; rU; mG; rA; rG; rG; rG; zc3p; zc3p$ |
| DDIT4_41a_S2072 SEQ ID NOS: 21 and 30) c6 amino on 5' sense strand | zc6Np; rC; rC; rC; rU; rC; rA; rG; rU; rA; rC; rU; rG; rU; rA; rG; mC; rA; mU; rA; zc3p<br>mU; rA; mU; rG; rC; rU2p; rA; mC; rA; rG; mU; rA; rC; rU; mG; rA; rG; rG; rG; zc3p; zc3p$ |
| DDIT4_41a_S2073 SEQ ID NOS: 21 and 30) THNB on 5' sense strand | zTHNBc6p; rC; rC; rC; rU; rC; rA; rG; rU; rA; rC; rU; rG; rU; rA; rG; mC; rA; mU; rA; zc3p<br>mU; rA; mU; rG; rC; rU2p; rA; mC; rA; rG; mU; rA; rC; rU; mG; rA; rG; rG; rG; zc3p; zc3p$ |

RACE: Rapid Amplification of cDNA Ends.

Figure 5A:
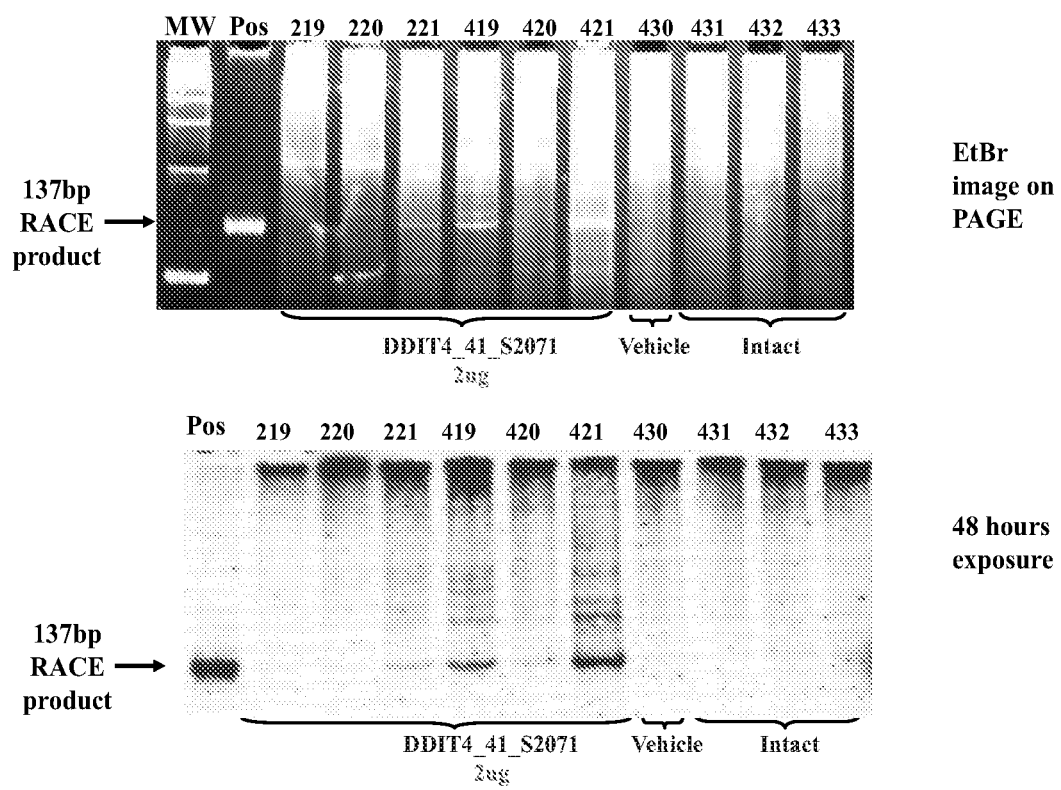
FIGS. 5A-5C show the results of mRNA cleavage in rat retina as shown by RACE of DDIT4_41a_S2071 molecule following intravitreal (IVT) injection, compared to DDIT4_1 (SEQ ID NO:45 and 46) alternating unmodified and 2'OMe modifications with (S500) or without (S073) 3' phosphate, DDIT4_41a_S2071, DDIT4_1S73 or DDIT4_1_S500 were injected bilaterally into rat eyes at 2 ug, 6 ug or 20 g per eye. mRNA cleavage was tested by RACE. RACE amplification product was separated by agarose gel electrophoresis and visualized by Ethidium bromide (EtBr) staining. The separated products were analyzed by Southern blot hybridization as using a probe specific for the predicted RACE cleavage junction. The upper image in each figure shows the EtBr staining and the lower image shows the Hybridization results. The clear bands in both the EtBr and hybridization staining in the samples taken from DDIT4_41a_S2071 treated retina indicate on the specific generation of the proper product predicted for RNAi-mediated cleavage of DDIT4 mRNA in DDIT4_41a_S2071 siRNA injected rat retina.
Figure 5B:
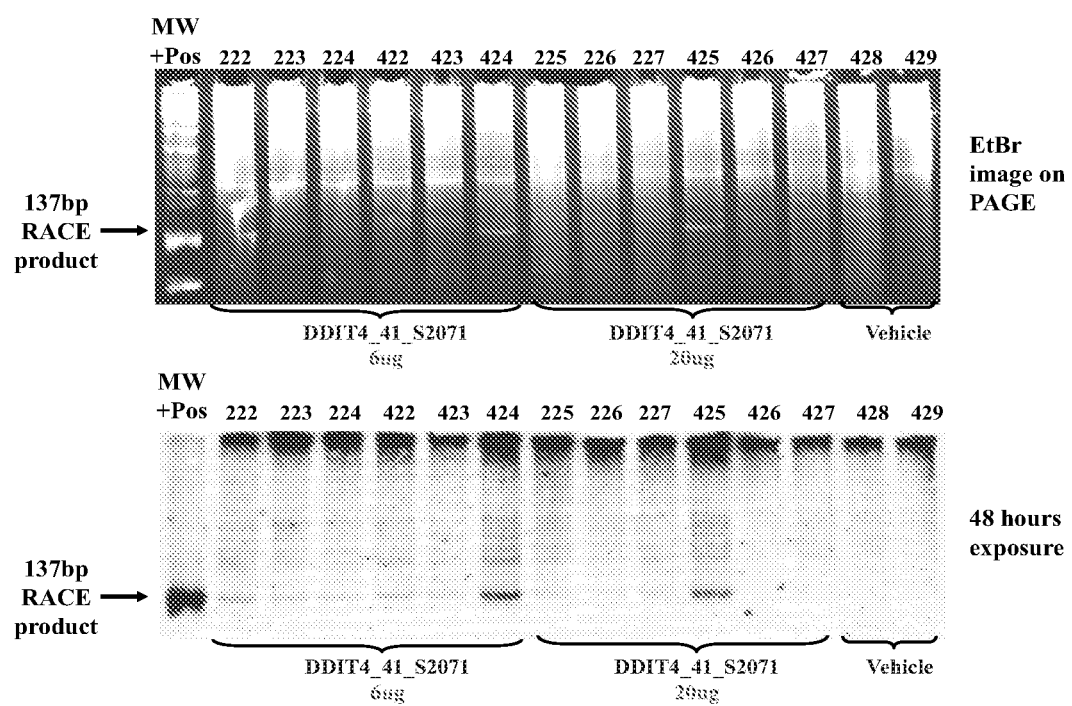
Figure 5C:
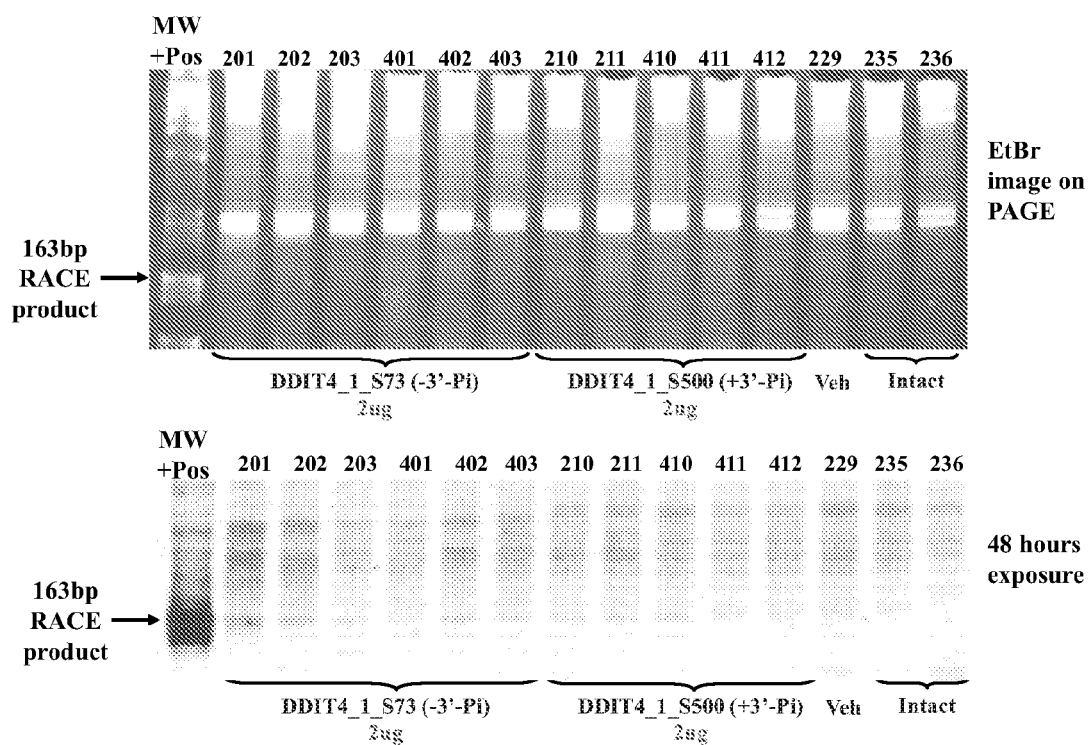

RACE procedure of dsRNA cleaved mRNA is performed according to standard methods known in the art. The RNAi-mediated cleavage of DDIT4 mRNA in the rat eye following IVT administration of the DDIT4_41a_2071 molecule was confirmed by Rapid Amplification of cDNA Ends (RACE). RNAi-mediated cleavage of a target mRNA occurs between nucleotides complementary to bases 10-11 of the siRNA guide strand to produce two mRNA fragments: a 5' fragment representing the region upstream to the cleavage site and the 3'-fragment representing the region downstream to the cleavage site. The presence of the downstream fragment can be detected using the RACE method, which is based on the ligation of an oligonucleotide adapter to the 5' end of this fragment, followed by PCR amplification using adapter-specific forward and gene-specific reverse primers. RNA was extracted from whole retina of rat eyes 24 hours after intravitreal (IVT) injection of 20 μg the siRNA and subjected to RACE analysis. Amplification product was separated by agarose gel electrophoresis and visualized by Ethidium bromide staining. The separated products were analyzed by Southern blot hybridization as using a probe specific for the predicted RACE cleavage junction. Hybridization results indicate the specific generation of the proper product predicted for RNAi-mediated cleavage of DDIT4 mRNA. FIGS. 5A-5C show results of RACE using the DDIT4_41a_S071 molecule disclosed herein.

Example 2

Generation of Sequences for Active dsRNA Molecules to DDIT4 and Production of the siRNAs Using proprietary algorithms and the known sequence of the mRNA of the target genes disclosed herein, the sequences of many potential dsRNA, i.e. siRNAs were generated. A key to the sequence listing is set forth hereinbelow:

SEQ ID NOS:3-11 and 12-20 set forth sense and antisense oligonucleotide sequences, respectively for generating dsRNA useful to down-regulate the expression of DDIT4. Each sense and antisense oligonucleotide sequence is presented in 5' to 3' orientation.

Specifically, SEQ ID NOS:21-29 and 30-48 provide human 19 mer oligonucleotides useful in generating dsRNA molecules to down regulate DDIT4 expression. The oligonucleoitde strands are preferably synthesized using chemically modified nucleotides and unconventional moieties including 2'OMe sugar modified ribonucleotides, 2'5' linked ribo and or deoxyribo nucleotides, TNA, pyrazolotriazine nucleotide analogues, mirror nucleotides, abasic moieties and the like. The molecules may be further covalently attached to conjugate moieties including peptide, lipids, vitamins, antibodies, saccharides etc by post synthesis coupling or by incorporating an agent phophoramidite into the oligonucleotide strand during synthesis.

The oligonucleotide sequences prioritized based on their score in the proprietary algorithm as the best predicted sequences for targeting the human gene expression.

"18+1" refers to a molecule that is 19 nucleotides in length and includes a mismatch to the mRNA target at position 1 of the antisense strand, according to Structure (A2). In preferred embodiments the sense strand is fully complementary to the antisense strand. In some embodiments the sense strand is mismatched to the antisense strand in 1, 2, or 3 positions.

Example 3

On-Target and Off-Target Testing of Double Stranded RNA Molecules

The psiCHECK™ system enables evaluation of the guide strand (GS) (antisense) and the passenger strand (PS) (sense strand) to elicit targeted (on-target) and off-targeted effects, by monitoring the changes in expression levels of their target sequences. Four psiCHECK™-2-based (Promega) constructs were prepared for the evaluation of target activity and potential off-target activity of each test molecule GS and PS strands. In each of the constructs one copy or three copies of either the full target or the seed-target sequence, of test molecule PS or GS, was cloned into the multiple cloning site located downstream of the Renilla luciferase translational stop codon in the 3'-UTR region. The resulting vectors were termed:

GS-CM (guide strand, complete-match) vector containing one copy of the full target sequence (nucleotide sequence fully complementary to the whole 19-base sequence of the GS of the test molecule);

PS-CM (passenger strand, complete-match) vector containing one copy of the full target sequence (nucleotide sequence fully complementary to the whole 19-base sequence of the PS of the test molecule);

GS-SM (guide strand, seed-match) vector containing one copy or three copies of the seed region target sequence (sequence complementary to nucleotides 1-8 of the GS of the test molecule);

PS-SM (passenger strand, seed-match) vector containing one copy of the seed region target sequence (sequence complementary to nucleotides 1-8 of the PS of the test molecule).

Nomenclature:

guide strand: strand of siRNA that enters the RISC complex and guides cleavage/silencing of the complementary RNA sequence seed sequence: Nucleotides 2-8 from the 5' end of the guide strand.

cm (complete match): DNA fragment fully complementary to the guide strand of siRNA. This DNA fragment is cloned in 3'UTR of a reporter gene and serves as a target for the straightforward RNA silencing.

sum (seed match): 19-mer DNA fragment with nucleotides ns 12-18 fully complementary to the ns 2-8 of the guide strand of siRNA. This DNA fragment is cloned in 3'UTR of a reporter gene and serves as a target for the "off-target" silencing.

X1: A single copy of cm or sum cloned in 3'UTR of a reporter gene.

X3 Three copies of cm or sum cloned in 3'UTR of a reporter gene, separated with 4 nucleotides one from another.

Example 4

On-Target and Off-Target Testing of DDIT4 Conjugates

The psiCHECK™ system was used to study on-target and off-target knockdown activity, as described above for Example 3.

The antisense strands of DDIT4_41_S2071, DDIT4_41_S2072, and DDIT4_41_S2073 as detailed in Example 8, as well as of DDIT4_41_S2012 and DDIT4_41_S2013 as described below were prepared. DDIT4_41_S2071, DDIT4_41 S2072, and DDIT4_41 S2073 were tested at concentrations of 0.005 nM, 0.015 nM, 0.045 nM, 0.137 nM, 0.41 nM, 1.23 nM, 3.7 nM, 11.1 nM, 33.3 nM, and 100 nM. DDIT4_41 S2012 and DDIT4_41 S2013 were tested at concentrations of 5 nM. Results of on-target knock-down are presented in Table 6 below, expressed as % residual mRNA.

| | |
|---|---|
| DDIT4_41_S2012 | Sense: rC; rC; rC; rU; mC; rA; rG; mU; rA; rC; mU; rG; mU; rA; rG; mC; rA; mU; rA; zc3p<br>Antisense:<br>mU; rA; mU; rG; rC; rU2p; rA; mC; rA; rG; mU; rA; rC; rU; mG; rA; rG; rG; rG; zc3p; zc3p$ |
| DDIT4_41_S2013 | Sense: rC; rC; rC; rU; rC; rA; rG; rU; rA; rC;<br>rU; rG; rU; rA; rG; mC; rA; mU; rA; zc3p<br>Antisense:<br>mU; rA; mU; rG; rC; rU2p; rA; mC; rA; rG; mU;<br>rA; rC; rU; mG; rA; rG; rG; rG; zc3p; zc3p$ |

TABLE 6

| DUPLEX NAME | CONCENTRATION (nM) | % RESIDUAL mRNA |
|---|---|---|
| DDIT4_41_S2071 | 0.005 | 43 |
|  | 0.015 | 32 |
|  | 0.045 | 24 |
|  | 0.137 | 14 |
|  | 0.41 | 8 |
|  | 1.23 | 6 |
|  | 3.7 | 4 |
|  | 11.1 | 4 |
|  | 33.3 | 3 |
|  | 100 | 3 |
| DDIT4_41_S2072 | 0.005 | 56 |
|  | 0.015 | 37 |
|  | 0.045 | 32 |
|  | 0.137 | 18 |
|  | 0.41 | 14 |
|  | 1.23 | 9 |
|  | 3.7 | 7 |
|  | 11.1 | 6 |
|  | 33.3 | 6 |
|  | 100 | 4 |
| DDIT4_41_S2073 | 0.005 | 66 |
|  | 0.015 | 53 |
|  | 0.045 | 42 |
|  | 0.137 | 30 |
|  | 0.41 | 19 |
|  | 1.23 | 15 |
|  | 3.7 | 7 |
|  | 11.1 | 6 |
|  | 33.3 | 7 |
|  | 100 | 6 |
| DDIT4_41_S2012 | 5 | 11 |
| DDIT4_41_S2013 | 5 | 9 |

Off-target knockdown activity for sense strands of DDIT4_41 S2071 with inverted deoxy abasic cap (idAB); DDIT4_41_S2072 with amino-C6 (Am-C6) cap; and DDIT4_41 S2073 conjugated to THNB was tested at concentrations of 0.005 nM, 0.015 nM, 0.045 nM, 0.137 nM, 0.41 nM, 1.23 nM, 3.7 nM, 11.1 nM, 33.3 nM, and 100 nM. DDIT4_41 S2012 and DDIT4_41 S2013 were tested at concentrations of 5 nM. Results are presented in Table 7 below, expressed as % residual mRNA. As shown in the Table, significantly less knockdown activity was seen with the sense strand as compared to the antisense strand.

TABLE 7

| DUPLEX NAME | CONCENTRATION (nM) | % RESIDUAL mRNA |
|---|---|---|
| DDIT4_41_S2071 | 0.005 | 59 |
|  | 0.015 | 73 |
|  | 0.045 | 68 |
|  | 0.137 | 61 |
|  | 0.41 | 57 |
|  | 1.23 | 41 |
|  | 3.7 | 46 |
|  | 11.1 | 41 |
|  | 33.3 | 42 |
|  | 100 | 33 |
| DDIT4_41_S2072 | 0.005 | 65 |
|  | 0.015 | 73 |
|  | 0.045 | 74 |
|  | 0.137 | 69 |
|  | 0.41 | 75 |
|  | 1.23 | 73 |
|  | 3.7 | 71 |
|  | 11.1 | 67 |
|  | 33.3 | 73 |
|  | 100 | 65 |
| DDIT4_41_S2073 | 0.005 | 78 |
|  | 0.015 | 74 |
|  | 0.045 | 75 |
|  | 0.137 | 75 |
|  | 0.41 | 66 |
|  | 1.23 | 76 |
|  | 3.7 | 72 |
|  | 11.1 | 71 |
|  | 33.3 | 73 |
|  | 100 | 75 |
| DDIT4_41_S2012 | 5 | 42 |
| DDIT4_41_S2013 | 5 | 32 |

Figure 4A:
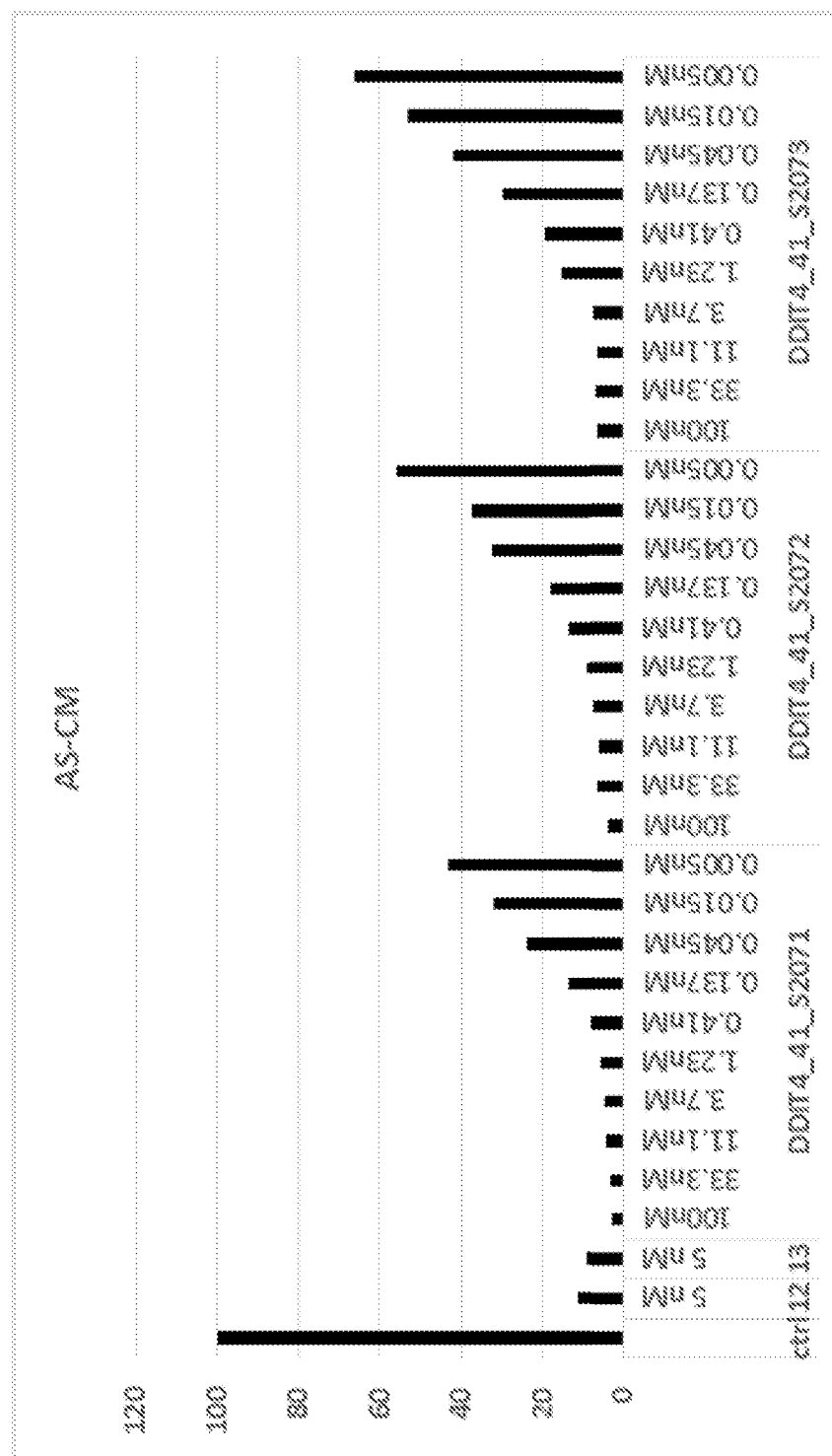
FIGS. 4A and 4B show activity as measured by % residual mRNA for the molecules DDIT4_41a_S2071, DDIT4_41a_S2072 and DDIT4_41a_S2073.
Figure 4B:
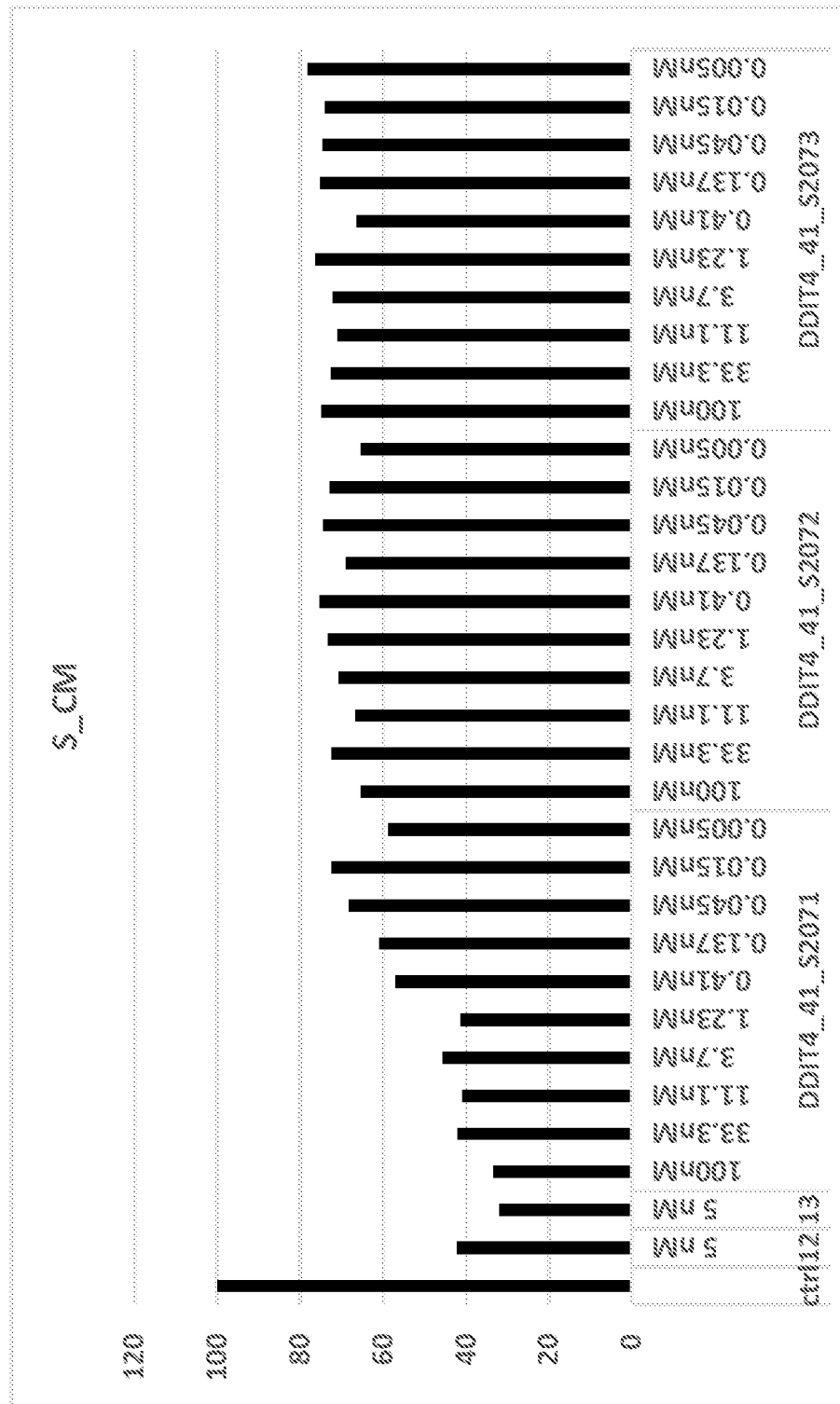

FIGS. 4A and 4B show the data in graphical form.

Example 4

The Effect of Target Gene dsRNA Treatment on Carboplatin-Induced Hair Cell Death in the Cochlea of Chinchilla Eight Chinchillas are pre-treated by direct administration of double stranded DDIT4 molecules in saline to the left ear of each animal. Saline is administered to the right ear of each animal as placebo. Two days following the administration of the double stranded DDIT4 molecules, the animals are treated with carboplatin (75 mg/kg iP). After sacrifice of the chinchillas (two weeks post carboplatin treatment) the % of dead cells of inner hair cells (IRC) and outer hair cells (ONC) is calculated in the left ear (siRNA treated) and in the right ear (saline treated). Since the effect of the siRNA is similar across dose, the data is pooled from the 3 doses. As was previously shown, carboplatin preferentially damages the inner hair cells in the chinchilla at the 75 mg/kg dose while the outer hair cells remain intact. The dsRNA compounds provided herein reduce ototoxin-induced (e.g. carboplatin-induced) inner hair cells loss in the cochlea. Other animal models are also possible.

Example 5

The Effect of dsRNA Treatment on Acoustic-Induced Hair Cell Death in the Cochlea of Chinchilla The activity of the dsRNA DDIT4 molecules described herein in an acoustic trauma model is studied in chinchilla. A group of 7 animals undergo acoustic trauma by exposing them to an octave band of noise centered at 4 kHz for 2.5 h at 105 dB. The left ear of the noise-exposed chinchillas is pre-treated (48 h before the acoustic trauma) with about 30 µg of double stranded DDIT4 molecules in ~10 µL of saline; the right ear is pre-treated with vehicle (saline). The compound action potential (CAP) is a convenient and reliable electrophysiological method for measuring the neural activity transmitted from the cochlea. The CAP is recorded by placing an electrode near the base of the cochlea in order to detect the local field potential that is generated when a sound stimulus, such as click or tone burst, is abruptly turned on. The functional status of each ear is assessed at about 2.5 weeks after the acoustic trauma. Specifically, the mean threshold of the compound action potential recorded from the round window is determined 2.5 weeks after the acoustic trauma in order to determine if the thresholds in the dsRNA-treated ear were lower (better) than the untreated (saline) ear. In addition, the amount of inner and outer hair cell loss is determined in the siRNA-treated and the control ear. The results indicate that dsRNAs provided herein, are capable of reducing acoustic trauma-induced ONC loss in the cochlea.

Example 6

The Effect of dsRNA Treatment on Cisplatin-Induced Hair Cell Death in the Cochlea of Rats Male Wistar Rats are tested for basal auditory brainstem response (ABR) thresholds for signals of clicks, 8, 16 and 32 kHz prior to cisplatin treatment. Following the basal auditory brainstem response testing, cisplatin is administered as an intraperitoneal infusion of 12 mg/kg over 30 minutes. Treated ears receive either 1 ug/4 microliter of dsRNA disclosed herein in PBS (applied directly to the round window membrane). Control ears are treated either with non-related GFP dsRNA or PBS. The dsRNA molecules are administered between 3-5 days prior to cisplatin administration in order to permit protective effect on the cochlea.

The auditory brainstem response (ABR) testing is repeated 3 days after cisplatin administration. The auditory brainstem response thresholds are compared between pre-treatment and post treatment and the shift in thresholds is measured. Higher shift in thresholds following cisplatin treatment is indicative for more severe hair cells loss in the cochlea. After the repeat of auditory brainstem response testing, animals are sacrificed and cochleae are removed and processed for scanning electron microscopy (SEM) to quantify outer hair cell (ONC) loss in the hook region (high frequency region). The % outer hair cell loss is calculated by dividing the number of missing or severely damaged cells by the total number of outer hair cells in the field of the photograph. The results indicate that dsRNAs molecules disclosed herein provide a protective effect to the cochlea when administered prior to ototoxin (e.g.cisplatin) administration.

Example 7

Model Systems of Acute Renal Failure (ARF)

ARF is a clinical syndrome characterized by rapid deterioration of renal function that occurs within days. Without being bound by theory the acute kidney injury may be the result of renal ischemia-reperfusion injury such as renal ischemia-reperfusion injury in patients undergoing major surgery such as major cardiac surgery. The principal feature of ARF is an abrupt decline in glomerular filtration rate (GFR), resulting in the retention of nitrogenous wastes (urea, creatinine) Recent studies, support that apoptosis in renal tissues is prominent in most human cases of ARF. The principal site of apoptotic cell death is the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum.

Testing an active dsRNA molecules is performed using an animal model for ischemia-reperfusion-induced ARF.
Protection Against Ischemia-Reperfusion Induced ARF Ischemia-reperfusion injury is induced in rats following 45 minutes bilateral kidney arterial clamp and subsequent release of the clamp to allow 24 hours of reperfusion. 12 mg/kg of molecules are injected into the jugular vein 30 minutes prior to and 4 hours following the clamp. ARF progression is monitored by measurement of serum creatinine levels before (baseline) and 24 hrs post surgery. At the end of the experiment, the rats are perfused via an indwelling femoral line with warm PBS followed by 4% paraformaldehyde. The left kidneys are surgically removed and stored in 4% paraformaldehyde for subsequent histological analysis. Acute renal failure is frequently defined as an acute increase of the serum creatinine level from baseline. An increase of at least 0.5 mg per dL or 44.2 µmol per L of serum creatinine is considered as an indication for acute renal failure. Serum creatinine is measured at time zero before the surgery and at 24 hours post ARF surgery.

The molecules disclosed herein are tested in the above model system and found to be protective against ischemia reperfusion.

Further, testing active molecules for treating ARF may also be done using sepsis-induced ARF.

Two predictive animal models of sepsis-induced ARF are described by Miyaji et al., 2003, *Ethyl pyruvate decreases sepsis-induced acute renal failure and multiple organ damage in aged mice*, Kidney Int. November; 64(5):1620-31. These two models are lipopolysaccharide administration and cecal ligation puncture in mice, preferably in aged mice.

Example 8

Optic Nerve Crush (ONC)

A rat optic nerve crush (ONC) model experiment is conducted exploring the effects of the molecules disclosed herein on 30 days post ONC survival of retinal ganglion cells (RGC) and regeneration of RGC axons. Groups of 4 rats are treated with bilateral ONC and each pair of eyes receive the same treatment (total n=8 per treatment group) with either PBS (vehicle), or siRNA targeting EGFP (negative control), or the molecules as described herein. siEGFP in monotherapy the animals were injected with 40 ug/eye. All siRNAs are injected at 20 ug/eye In all cases, the final injection volume was 10 ul The study is terminated on Day 24, eyes with optic nerves are enucleated and subjected to histological evaluation of RGC survival and optic nerve axon outgrowth.

In Vivo Study Design: The groups will undergo bilateral ONC. Each pair of eyes will receive the same treatment. siRNA administration for all groups will be via bilateral intravitreal injection (IVT) every 10 days. Termination for groups is 24 or 40 days post ONC.

Evaluation of RGC survival at 24 days post Optic Nerve Crush

For RGC counts, 20×15 µm thick sections of the eye, with the optic nerve clearly visible, ae taken and every $4^{th}$ section is selected and stained for β-III tubulin and DAPI to reveal the RGC (total 50-60 sections per group were evaluated). A linear 250 µm region of the retina either side of the optic nerve is used to count numbers of βIII+RGC/250 µm of retina.

Example 9

Model Systems Relating to Macular Degeneration

The molecules described herein are tested in the following an animal model of Choroidal neovascularization (CNV). This hallmark of wet AMD is induced in model animals by laser treatment.

A) Mouse Model

Choroidal neovascularization (CNV) induction: Choroid neovascularization (CNV), a hallmark of wet AMD, is triggered by laser photocoagulation (532 nm, 200 mW, 100 ms, 75 µm) (OcuLight GL, Iridex, Mountain View, Calif.) performed on both eyes of each mouse on day 0 by a single individual masked to drug group assignment. Laser spots are applied in a standardized fashion around the optic nerve, using a slit lamp delivery system and a cover slip as a contact lens.

Evaluation: For evaluation, the eyes are enucleated and fixed with 4% paraformaldehyde for 30 min at 4° C. The neurosensory retina is detached and severed from the optic nerve. The remaining RPE-choroid-sclera complex is flat mounted in Immu-Mount (Vectashield Mounting Medium, Vector) and covered with a coverslip. Flat mounts are examined with a scanning laser confocal microscope (TCS SP, Leica, Germany). Vessels are visualized by exciting with blue argon laser. The area of CNV-related fluorescence is measured by computerized image analysis using the Leica TCS SP software. The summation of whole fluorescent area in each horizontal section is used as an index for the volume of CNV.

B) Non-Human Primate Model

CNV induction: Choroidal neovascularization (CNV) is induced in male Cynomolgus monkeys by perimacular laser treatment of both eyes prior to dose administration. The approximate laser parameters were as follows: spot size: 50-100 μm diameter; laser power: 300-700 milliwatts; exposure time: 0.1 seconds.

Treatment: Immediately following laser treatment, both eyes of all animals are subjected to a single intravitreal injection. Left eye is dosed with synthetic stabilized siRNA against RTP801, whereas the contralateral eye receives PBS (vehicle).

Molecules disclosed herein are tested in the above animal models of macular degeneration, in which it is shown that RTP801 siRNA molecules are effective in treatment of macular degeneration.

Example 10

Model Systems Relating to Microvascular Disorders

The molecules described herein are tested in animal models of a range of microvascular disorders as described below.

1. Diabetic Retinopathy

DDIT4 (RTP801) promotes neuronal cell apoptosis and generation of reactive oxygen species in vitro. The assignee of the current application also found that in RTP801 knockout (KO) mice subjected to the model of retinopathy of prematurity (ROP), pathologic neovascularization NV was reduced under hypoxic conditions, despite elevations in VEGF, whereas the lack of this gene did not influence physiologic neonatal retinal NV. Moreover, in this model, lack of RTP801 was also protective against hypoxic neuronal apoptosis and hyperoxic vaso-obliteration.

Experiment 1: Diabetes is induced in RTP801 KO and C57/129sv wildtype (WT) littermate mice by intraperitoneal injection of STZ. After 4 weeks, ERG (single white flash, 1.4×10^4 ftc, 5 ms) is obtained from the left eye after 1 hour of dark adaptation. RVP is assessed from both eyes using the Evans-blue albumin permeation technique.

Experiment 2: Diabetes is induced in RTP801 knockout and in control wild type mice with the matched genetic background. For diabetes induction, the mice are injected with streptozotocin (STZ 90 mg/kg/d for 2 days after overnight fast). Animal physiology is monitored throughout the study for changes in blood glucose, body weight, and hematocrit. Vehicle-injected mice serve as controls. The appropriate animals are treated by intravitreal injections of anti-RTP801 siRNA or anti-GFP control siRNA.

Retinal vascular leakage is measured using the Evans-blue (EB) dye technique on the animals. Mice have a catheter implanted into the right jugular vein prior to Evans Blue (EB) measurements. Retinal permeability measurements in both eyes of each animal follows a standard Evans-blue protocol.

Retinopathy of Prematurity

Retinopathy of prematurity is induced by exposing the test animals to hypoxic and hyperoxic conditions, and subsequently testing the effects on the retina. Results show that RTP801 (DDIT4) KO mice are protected from retinopathy of prematurity, thereby validating the protective effect of DDIT4 inhibition.

Microvascular Ischemic Conditions

Animal models useful for assessing ischemic conditions include:

1. Closed Head Injury (CHI)—Experimental TBI produces a series of events contributing to neurological and neurometabolic cascades, which are related to the degree and extent of behavioral deficits. CHI is induced under anesthesia, while a weight is allowed to free-fall from a prefixed height (Chen et al, J. Neurotrauma 13, 557, 1996) over the exposed skull covering the left hemisphere in the midcoronal plane.

2. Transient middle cerebral artery occlusion (MCAO)—a 90 to 120 minutes transient focal ischemia is performed in adult, male Sprague Dawley rats, 300-370 gr. The method employed is the intraluminal suture MCAO (Longa et al., Stroke, 30, 84, 1989, and Dogan et al., J. Neurochem. 72, 765, 1999). Briefly, under halothane anesthesia, a 3-O-nylon suture material coated with Poly-L-Lysine is inserted into the right internal carotid artery (ICA) through a hole in the external carotid artery. The nylon thread is pushed into the ICA to the right MCA origin (20-23 mm). 90-120 minutes later the thread is pulled off, the animal is closed and allowed to recover.

3. Permanent middle cerebral artery occlusion (MCAO)—occlusion is permanent, unilateral-induced by electrocoagulation of MCA. Both methods lead to focal brain ischemia of the ipsilateral side of the brain cortex leaving the contralateral side intact (control). The left MCA is exposed via a temporal craniotomy, as described for rats by Tamura A. et al., *J Cereb Blood Flow Metab.* 1981; 1:53-60. The MCA and its lenticulostriatal branch are occluded proximally to the medial border of the olfactory tract with microbipolar coagulation. The wound is sutured, and animals returned to their home cage in a room warmed at 26° C. to 28° C. The temperature of the animals is maintained all the time with an automatic thermostat.

The molecules described herein are tested in the above animal models of microvascular conditions, in which it is shown that dsRNA to DDIT4 ameliorate the symptoms of microvascular conditions.

Example 11

Model Systems for Neurodegenerative Diseases and Disorders

I. Evaluating the Efficacy of Intranasal Administration of Molecules Disclosed Herein in the APP Transgenic Mouse Model of Alzheimer's Disease.

Animals and Treatment. The study includes twenty-four (24) APP [V717I] transgenic mice (female), a model for Alzheimer's disease (Moechars D. et al., EMBO J. 15(6):

1265-74, 1996; Moechars D. et al., *Neuroscience.* 91(3): 819-30), aged 11 months that are randomly divided into two equal groups (Group I and Group II).

Animals are treated with intranasal administration siRNA (200-400 ug/mice, Group I) and vehicle (Group II), 2-3 times a week, during 3 months.

Administration of siRNA. The route of administration of the siRNA is intranasal instillation, with administration twice weekly, starting from 30 days of age.

Analysis of disease progression. Behavioral and electromyography (EMG) analysis in treated and untreated mice is performed to monitor disease onset and progression. Mice are pre-tested before start of siRNA treatment, followed by weekly assessments. All results are compared statistically. The following tests are performed:

1. Swimming tank test: this test is particularly sensitive at detecting changes in hind-limb motor function (Raoul et al., 2005. *Nat Med.* 11, 423-428; Towne et al, 2008. *Mol Ther.* 16:1018-1025).

2. Electromyography: EMG assessments are performed in the gastrocnemius muscle of the hind limbs, where compound muscle action potential (CMAP) is recorded (Raoul et al., 2005. supra).

Post mortem histopathology. At the disease end-point mice are terminally anaesthetized and spinal cord and hind-limb muscle tissue are collected for histological and biochemical analysis.

Examining motor neuron survival. Transverse sections of lumbar spinal cord are cut using a cryostat and stained with gallocyanin, a nissl stain. From these sections the number of motor neurons in the lumbar spinal cord is counted (Kieran et al., 2007. supra), to determine whether siRNA treatment prevents motor neuron degeneration in $SOD1^{G93A}$ mice.

Examining spinal cord histopathology. Motor neuron degeneration in $SOD1^{G93A}$ mice results in astrogliosis and activation of microglial cells. Here, using transverse sections of lumbar spinal cord the activation of astrocytes and microglial cells is examined using immunocytochemistry to determine whether siRNA treatment reduced or prevented their activation.

Examining muscle histology. Muscles are then processed histologically to examine motor end plate denervation and muscle atrophy (Kieran et al., 2005. J Cell Biol. 169, 561-567).

Although the above examples have illustrated particular ways of carrying out embodiments of the invention, in practice persons skilled in the art will appreciate alternative ways of carrying out embodiments of the invention, which are not shown explicitly herein. It should be understood that the present disclosure is to be considered as an exemplification of the principles of this invention and is not intended to limit the invention to the embodiments illustrated.

Those skilled in the art will recognize, or be able to ascertain using no more than routine experimentation, equivalents of the specific embodiments of the invention described herein. Such equivalents are intended to be encompassed by the following claims.

---

That which is claimed is:

1. A double-stranded nucleic acid molecule capable of targeting DDIT4 mRNA (SEQ ID NO:1), wherein
   (a) the double-stranded nucleic acid molecule includes a sense strand and an antisense strand and wherein each strand is independently 18 to 49 nucleotides in length;
   (b) a 18 to 49 nucleotide sequence of the antisense strand is complementary to a 18 to 49 consecutive nucleotide sequence in the DDIT4 mRNA;
   (c) a 18 to 49 nucleotide sequence of the sense strand is complementary to the antisense strand; and
   (d) the sense strand and the antisense strand comprise oligonucleotide sequence pairs set forth in SEQ ID NOs:3 and 12;
   or a pharmaceutically acceptable salt of such molecule.

2. The double-stranded nucleic acid molecule of claim 1, having a structure (A2) set forth below:

5' $N^1$—(N)x—Z 3' (antisense strand)

3' Z'—$N^2$—(N')y—z" 5' (sense strand)                (A2)

wherein each of $N^2$, N and N' is an unmodified or modified ribonucleotide, or an unconventional moiety;
   wherein each of (N)x and (N')y is an oligonucleotide in which each consecutive N or N' is joined to the adjacent N or N' by a covalent bond;
   wherein each of x and y is independently an integer between 17 and 39;
   wherein $N^2$ is covalently bound to (N')y;
   wherein $N^1$ is covalently bound to (N)x and is mismatched to DDIT4 mRNA (SEQ ID NO:1) or is a deoxyribonucleotide complementary to the DDIT4 mRNA, and is selected from the group consisting of: natural or modified uridine, deoxyribouridine, ribothymidine, deoxyribothymidine, adenosine or deoxyadenosine;
   wherein z" may be present or absent, but if present is a capping moiety or a conjugate moiety covalently attached at the 5' terminus of $N^2$—(N')y;
   wherein each of Z and Z' is independently present or absent, but if present is independently 1-5 consecutive nucleotides, non-nucleotide moieties unconventional moieties or a combination thereof or a drug or vitamin moiety covalently attached at the 3' terminus of the strand in which it is present;
   wherein the sequence of (N')y is complementary to the sequence of (N)x; and wherein the sequence of (N')y comprises a sense strand and (N)x comprises an antisense strand set forth in the oligonucleotide pairs SEQ ID NOs:3 and 12.

3. The double-stranded nucleic acid molecule of claim 2, wherein x=y=18.

4. The double-stranded nucleic acid molecule of claim 3, described as DDIT4_41a, wherein $N^1$—(N)x comprises an oligonucleotide of SEQ ID NO:30 and $N^2$—(N')y comprises an oligonucleotide of SEQ ID NO:21.

5. The double stranded nucleic acid molecule of claim 4, having the structure

```
5'    UAUGCUACAGUACUGAGGG-Z 3'    (antisense SEQ ID NO: 30)
      ||||||||||||||||||
3' Z'-AUACGAUGUCAUGACUCCC-z" 5'   (sense SEQ ID NO: 21)
``` wherein each of A, C, G, U is independently an unmodified or modified ribonucleotide, or an unconventional moiety;

wherein each "|" represents base pairing between the ribonucleotides/unconventional moieties;

wherein each of Z and Z' is independently present or absent, but if present is independently 1-5 consecutive nucleotides, non-nucleotide moieties, unconventional moieties or a combination thereof or a conjugate moiety covalently attached at the 3' terminus of the strand in which it is present; and wherein z" may be present or absent, but if present is a capping moiety or a conjugate moiety covalently attached at the 5' terminus of N2-(N')y; or a pharmaceutically acceptable salt of such molecule.

6. The double stranded nucleic acid molecule of claim 5, wherein the antisense strand (SEQ ID NO:30) comprises one or more 2'OMe sugar modified pyrimidines and or purines, a 2'-5' ribonucleotide in position 5, 6, 7 or 8, and a 3' terminal nucleotide or non-nucleotide overhang.

7. The double stranded nucleic acid molecule of claim 6, wherein the antisense strand (SEQ ID NO:30) comprises 2'OMe sugar modified ribonucleotides at positions (5'>3') 1, 3, 8, 11, and 15, a 2'-5' ribonucleotide at position 6, and a C3Pi-C3OH or C3Pi-C3Pi moiety covalently attached to the 3' terminus.

8. The double stranded nucleic acid molecule of claim 7, wherein the sense strand (SEQ ID NO:21) comprises one or more 2'OMe pyrimidine, a nucleotide or non-nucleotide moiety covalently attached at the 3' terminus and a cap moiety covalently attached at the 5' terminus.

9. The double stranded nucleic acid molecule of claim 8, wherein the sense strand (SEQ ID NO:21) comprises 2'OMe sugar modified ribonucleotides at positions (5'>3') 16 and 18 a C3OH or C3Pi moiety covalently attached at the 3' terminus; and a cap moiety covalently attached at the 5' terminus, wherein the cap moiety is selected from the group consisting of: an inverted abasic deoxyribonucleotide moiety, a C6 amino moiety and a 6[(5,6,7,8-tetrahydronaphthalene)butyric amide] (THNB) moiety.

10. The double stranded nucleic acid molecule of claim 8, wherein the sense strand (SEQ ID NO:21) comprises 2'-5' linked ribonucleotides at positions 15, 16, 17, 18 and 19, a C3OH or C3Pi moiety covalently attached at the 3' terminus and optionally a capping moiety covalently attached at the 5' terminus.

11. The double stranded nucleic acid molecule of claim 5, wherein the antisense strand (SEQ ID NO:30) comprises 2'OMe sugar modified ribonucleotides at positions (5'>3') 1, 3, 8, 11, and 15, a 2'-5' ribonucleotide at position 6, and a C3Pi-C3Pi moiety covalently attached to the 3' terminus; and the sense strand (SEQ ID NO:21) comprises 2'OMe sugar modified ribonucleotides at positions (5'>3') 16 and 18, a C3Pi 3' terminal overhang; and an inverted abasic deoxyribonucleotide moiety covalently attached at the 5' terminus.

12. The double-stranded nucleic acid molecule of claim 2, wherein z" is present and is selected from the group consisting of abasic ribose moiety, abasic deoxyribose moiety, modifications of abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'OMe nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; bridging or non bridging methylphosphonate, 5'-mercapto moieties or a phenyl hydrocarbyl moiety, for example THNB.

13. The double-stranded nucleic acid molecule of claim 12, wherein z" is selected from an inverted deoxyabasic moiety, an amino C6 moiety and THNB.

14. The double-stranded nucleic acid molecule of claim 2, wherein Z' comprises a C3Pi moiety; and wherein Z comprises a C3Pi-C3Pi moiety.

15. The double-stranded nucleic acid molecule of claim 2, wherein the covalent bond is a phosphodiester bond.

16. The double-stranded nucleic acid molecule of claim 1, wherein the nucleic acid molecule comprises one or more modified nucleobases; and wherein said one or more modified nucleobase are independently selected from the group consisting of xanthine, hypoxanthine, 2-aminoadenine, 6-methyl and other alkyl derivatives of adenine and guanine, 2-propyl and other alkyl derivatives of adenine and guanine, 5-thiouracil and cytosine, 5-propenyl uracil and cytosine, 6-aza uracil, cytosine and thymine, 5-uracil (pseudouracil), 4-thiouracil, 8-halo, amino, thiol, thioalkyl, hydroxyl and other 8-substituted adenines and guanines, 5-trifluoromethyl and other 5-substituted uracil and cytosine's, 7-methyl guanine, pyrazolotriazine analogue, and acyclonucleotides.

17. The double-stranded nucleic acid molecule of claim 1, wherein the nucleic acid molecule comprises one or more modifications to the phosphodiester backbone; and wherein said one or more modifications to the phosphodiester backbone are independently selected from the group consisting of a phosphorothioate, 3'-(or -5')deoxy-3'-(or -5')thio-phosphorothioate, phosphorodithioate, phosphoroselenates, 3'-(or -5')deoxy phosphinates, borano phosphates, 3'-(or -5') deoxy-3'-(or 5'-)amino phosphoramidates, hydrogen phosphonates, borano phosphate esters, phosphoramidates, alkyl or aryl phosphonates, and phosphotriester linkages.

18. The double-stranded nucleic acid molecule of claim 1, wherein one or both of the sense strand and/or the antisense strand comprise 1-5 deoxyribonucleotides, 1-5 non-nucleotide moieties, 1-5 unconventional moieties or a combination thereof covalently attached at the 3'-end of the sense strand, the antisense strand or both the sense strand and the antisense strand; and/or wherein one or both of the sense strand and/or the antisense strand comprise a phosphate group at the 5'-end; and/or wherein one or both of the sense strand and/or the antisense strand comprise a phosphate group at the 3'-end.

19. A composition comprising the double-stranded nucleic acid molecule of claim 1 and a pharmaceutically acceptable carrier.

20. A method of treating a disease or disorder in a subject whereby expression of the DDIT4 gene is associated with the etiology or progression of the disease or disorder, comprising administering to the subject a therapeutically effective amount of the composition of claim 19, thereby treating the disease or disorder in the subject.

* * * * *

SEQUENCE LISTING

```
<160> NUMBER OF SEQ ID NOS: 44

<210> SEQ ID NO 1
<211> LENGTH: 1752
<212> TYPE: RNA
<213> ORGANISM: HomoSapiens

<400> SEQUENCE: 1
agggcgcagc aggccaaggg ggaggugcga gcguggaccu gggacgdgguc ugggcggcuc      60 ucggugguug gcacggguuc gcacacccau ucaagcggca ggacgcacuu gucuuagcag     120
uucucgcuga ccgcgcuagc ugcggcuucu acgcuccggc acucugaguu caucagcaaa     180
cgcccuggcg ucuguccuca ccaugccuag ccuuugggac cgcuucucgu cgucguccac     240
cuccucuucg cccucguccu ugccccgaac ucccacccca gaucggccgc cgcgcucagc     300 cuggggcgucg gcgacccggg aggagggguu ugaccgcucc acgagccugg agagcucgga     360 cugcgaguccc cuggacagca gcaacagugg cuucgggccg gaggaagaca cggcuuaccu     420
ggauggggug ucguugcccg acuucgagcu gcucagugac ccugaggaug aacacuugug     480
ugccaaccug augcagcugc ugcaggagag ccuggcccag gcgcggcugg gcucucgacg     540
cccugcgcgc cugcugaugc cuagccaguu gguaagccag gugggcaaag aacuacugcg     600
ccuggccuac agcgagccgu gcggccugcg gggggcgcug cuggacgucu gcguggagca     660
gggcaagagc ugccacagcg ugggccagcu ggcacucgac cccagccugg ugcccaccuu     720
ccagcugacc cucgugcugc gccuggacuc acgacucugg cccaagaucc aggggcuguu     780
uagcuccgcc aacucuccccu uccuccugg cuucagccag ucccugacgc ugagcacugg     840
cuuccgaguc aucaagaaga agcuguacag cucggaacag cugcucauug aggagguguug     900 aacuucaacc ugaggggggcc gacagugccc uccaagacag agcgacuga acuuuuggg     960
```

-continued
uggagacuag aggcaggagc ugagggacug auuccugugg uuggaaaacu gaggcagcca 1020
ccuaaggugg aggugggga auaguguuuc ccaggaagcu cauugaguug ugugcgggug 1080
gcugugcauu ggggacacau accccucagu acuguagcau gaaacaaagg cuuaggggcc 1140
aacaaggcuu ccagcuggau gugugugag cauguaccuu auuauuuuug uuacugacag 1200
uuaacagugg ugugacaucc agagagcagc ugggcugcuc ccgccccagc ccggcccagg 1260
gugaaggaag aggcacgugc ucccucagagc agccggaggg aggggggagg ucggaggucg 1320
uggaggugu uuguguaucu uacuggucug aagggaccaa guguguuugu uguuuguuuu 1380
guaucuuguu uuucugaucg gagcaucacu acugaccugu uguaggcagc uaucuuacag 1440
acgcaugaau guaagaguag gaaggggugg gugucaggga ucacuuggga ucuuugacac 1500
uugaaaaauu acaccuggca gcugcguuua agccuucccc caucguguac ugcagaguug 1560
agcuggcagg ggaggggcug agaggguggg ggcuggaacc ccuccccggg aggagugcca 1620
ucugggucuu ccaucuagaa cuguuuacau gaagauaaga uacucacugu ucaugaauac 1680
acuugauguu caaguauuaa gaccuaugca auauuuuuua cuuuucuaau aaacauguuu 1740
guuaaaacag uu 1752

<210> SEQ ID NO 2
<211> LENGTH: 232
<212> TYPE: PRT
<213> ORGANISM: Homo sapiens

<400> SEQUENCE: 2

Met Pro Ser Leu Trp Asp Arg Phe Ser Ser Ser Ser Thr Ser Ser Ser
1 5 10 15

Pro Ser Ser Leu Pro Arg Thr Pro Thr Pro Asp Arg Pro Pro Arg Ser
20 25 30

Ala Trp Gly Ser Ala Thr Arg Glu Glu Gly Phe Asp Arg Ser Thr Ser
35 40 45

Leu Glu Ser Ser Asp Cys Glu Ser Leu Asp Ser Ser Asn Ser Gly Phe
50 55 60

Gly Pro Glu Glu Asp Thr Ala Tyr Leu Asp Gly Val Ser Leu Pro Asp
65 70 75 80

Phe Glu Leu Leu Ser Asp Pro Glu Asp Glu His Leu Cys Ala Asn Leu
85 90 95

Met Gln Leu Leu Gln Glu Ser Leu Ala Gln Ala Arg Leu Gly Ser Arg
100 105 110

Arg Pro Ala Arg Leu Leu Met Pro Ser Gln Leu Val Ser Gln Val Gly
115 120 125

Lys Glu Leu Leu Arg Leu Ala Tyr Ser Glu Pro Cys Gly Leu Arg Gly
130 135 140

Ala Leu Leu Asp Val Cys Val Glu Gln Gly Lys Ser Cys His Ser Val
145 150 155 160

Gly Gln Leu Ala Leu Asp Pro Ser Leu Val Pro Thr Phe Gln Leu Thr
165 170 175

Leu Val Leu Arg Leu Asp Ser Arg Leu Trp Pro Lys Ile Gln Gly Leu
180 185 190

Phe Ser Ser Ala Asn Ser Pro Phe Leu Pro Gly Phe Ser Gln Ser Leu
195 200 205

Thr Leu Ser Thr Gly Phe Arg Val Ile Lys Lys Lys Leu Tyr Ser Ser
210 215 220

Glu Gln Leu Leu Ile Glu Glu Cys

<210> SEQ ID NO 3
<211> LENGTH: 18
<212> TYPE: RNA
<213> ORGANISM: artificial
<220> FEATURE:
<223> OTHER INFORMATION: Chemically synthesized

<400> SEQUENCE: 3
cccucaguac uguagcau                                                18

<210> SEQ ID NO 4
<211> LENGTH: 18
<212> TYPE: RNA
<213> ORGANISM: artificial
<220> FEATURE:
<223> OTHER INFORMATION: Chemically synthesized

<400> SEQUENCE: 4
ggcagcuauc uuacagac                                                18

<210> SEQ ID NO 5
<211> LENGTH: 18
<212> TYPE: RNA
<213> ORGANISM: artificial
<220> FEATURE:
<223> OTHER INFORMATION: Chemically synthesized

<400> SEQUENCE: 5
agagcucgga cugcgagu                                                18

<210> SEQ ID NO 6
<211> LENGTH: 18
<212> TYPE: RNA
<213> ORGANISM: artificial
<220> FEATURE:
<223> OTHER INFORMATION: Chemically synthesized

<400> SEQUENCE: 6
gggucuucca ucuagaac                                                18

<210> SEQ ID NO 7
<211> LENGTH: 18
<212> TYPE: RNA
<213> ORGANISM: artificial
<220> FEATURE:
<223> OTHER INFORMATION: Chemically synthesized

<400> SEQUENCE: 7 ggguggagacu agaggcag                                               18

<210> SEQ ID NO 8
<211> LENGTH: 18
<212> TYPE: RNA
<213> ORGANISM: artificial
<220> FEATURE:
<223> OTHER INFORMATION: Chemically synthesized

<400> SEQUENCE: 8
ccuccaagac agagacga                                                18

<210> SEQ ID NO 9
<211> LENGTH: 18
<212> TYPE: RNA
<213> ORGANISM: artificial

-continued

```
<220> FEATURE:
<223> OTHER INFORMATION: Chemically synthesized

<400> SEQUENCE: 9
ggaagcucau ugaguugu                                                 18

<210> SEQ ID NO 10
<211> LENGTH: 18
<212> TYPE: RNA
<213> ORGANISM: artificial
<220> FEATURE:
<223> OTHER INFORMATION: Chemically synthesized

<400> SEQUENCE: 10
gcagcugcgu uuaagccu                                                 18

<210> SEQ ID NO 11
<211> LENGTH: 18
<212> TYPE: RNA
<213> ORGANISM: artificial
<220> FEATURE:
<223> OTHER INFORMATION: Chemically synthesized

<400> SEQUENCE: 11
caguacugua gcaugaaa                                                 18

<210> SEQ ID NO 12
<211> LENGTH: 18
<212> TYPE: RNA
<213> ORGANISM: artificial
<220> FEATURE:
<223> OTHER INFORMATION: Chemically synthesized

<400> SEQUENCE: 12
augcuacagu acugaggg                                                 18

<210> SEQ ID NO 13
<211> LENGTH: 18
<212> TYPE: RNA
<213> ORGANISM: artificial
<220> FEATURE:
<223> OTHER INFORMATION: Chemically synthesized

<400> SEQUENCE: 13
gucuguaaga uagcugcc                                                 18

<210> SEQ ID NO 14
<211> LENGTH: 18
<212> TYPE: RNA
<213> ORGANISM: artificial
<220> FEATURE:
<223> OTHER INFORMATION: Chemically synthesized

<400> SEQUENCE: 14
acucgcaguc cgagcucu                                                 18

<210> SEQ ID NO 15
<211> LENGTH: 18
<212> TYPE: RNA
<213> ORGANISM: artificial
<220> FEATURE:
<223> OTHER INFORMATION: Chemically synthesized

<400> SEQUENCE: 15
guucuagaug gaagaccc                                                 18
```

<210> SEQ ID NO 16
<211> LENGTH: 18
<212> TYPE: RNA
<213> ORGANISM: artificial
<220> FEATURE:
<223> OTHER INFORMATION: Chemically synthesized

<400> SEQUENCE: 16
cugccucuag ucuccacc                                                 18

<210> SEQ ID NO 17
<211> LENGTH: 18
<212> TYPE: RNA
<213> ORGANISM: artificial
<220> FEATURE:
<223> OTHER INFORMATION: Chemically synthesized

<400> SEQUENCE: 17
ucgucucugu cuuggagg                                                 18

<210> SEQ ID NO 18
<211> LENGTH: 18
<212> TYPE: RNA
<213> ORGANISM: artificial
<220> FEATURE:
<223> OTHER INFORMATION: Chemically synthesized

<400> SEQUENCE: 18
acaacucaau gagcuucc                                                 18

<210> SEQ ID NO 19
<211> LENGTH: 18
<212> TYPE: RNA
<213> ORGANISM: artificial
<220> FEATURE:
<223> OTHER INFORMATION: Chemically synthesized

<400> SEQUENCE: 19
aggcuuaaac gcagcugc                                                 18

<210> SEQ ID NO 20
<211> LENGTH: 18
<212> TYPE: RNA
<213> ORGANISM: artificial
<220> FEATURE:
<223> OTHER INFORMATION: Chemically synthesized

<400> SEQUENCE: 20
uuucaugcua caguacug                                                 18

<210> SEQ ID NO 21
<211> LENGTH: 19
<212> TYPE: RNA
<213> ORGANISM: artificial
<220> FEATURE:
<223> OTHER INFORMATION: Chemically synthesized

<400> SEQUENCE: 21
cccucaguac uguagcaua                                                19

<210> SEQ ID NO 22
<211> LENGTH: 19
<212> TYPE: RNA
<213> ORGANISM: artificial
<220> FEATURE:
<223> OTHER INFORMATION: Chemically synthesized

```
<400> SEQUENCE: 22
ggcagcuauc uuacagaca                                              19

<210> SEQ ID NO 23
<211> LENGTH: 19
<212> TYPE: RNA
<213> ORGANISM: artificial
<220> FEATURE:
<223> OTHER INFORMATION: Chemically synthesized

<400> SEQUENCE: 23
agagcucgga cugcgagua                                              19

<210> SEQ ID NO 24
<211> LENGTH: 19
<212> TYPE: RNA
<213> ORGANISM: artificial
<220> FEATURE:
<223> OTHER INFORMATION: Chemically synthesized

<400> SEQUENCE: 24
gggucuucca ucuagaaca                                              19

<210> SEQ ID NO 25
<211> LENGTH: 19
<212> TYPE: RNA
<213> ORGANISM: artificial
<220> FEATURE:
<223> OTHER INFORMATION: Chemically synthesized

<400> SEQUENCE: 25
gguggagacu agaggcaga                                              19

<210> SEQ ID NO 26
<211> LENGTH: 19
<212> TYPE: RNA
<213> ORGANISM: artificial
<220> FEATURE:
<223> OTHER INFORMATION: Chemically synthesized

<400> SEQUENCE: 26
ccuccaagac agagacgaa                                              19

<210> SEQ ID NO 27
<211> LENGTH: 19
<212> TYPE: RNA
<213> ORGANISM: artificial
<220> FEATURE:
<223> OTHER INFORMATION: Chemically synthesized

<400> SEQUENCE: 27
ggaagcucau ugaguugua                                              19

<210> SEQ ID NO 28
<211> LENGTH: 19
<212> TYPE: RNA
<213> ORGANISM: artificial
<220> FEATURE:
<223> OTHER INFORMATION: Chemically synthesized

<400> SEQUENCE: 28
gcagcugcgu uuaagccua                                              19

<210> SEQ ID NO 29
```

```
<211> LENGTH: 19
<212> TYPE: RNA
<213> ORGANISM: artificial
<220> FEATURE:
<223> OTHER INFORMATION: Chemically synthesized

<400> SEQUENCE: 29
caguacugua gcaugaaau                                                    19

<210> SEQ ID NO 30
<211> LENGTH: 19
<212> TYPE: RNA
<213> ORGANISM: artificial
<220> FEATURE:
<223> OTHER INFORMATION: Chemically synthesized

<400> SEQUENCE: 30
uaugcuacag uacugaggg                                                    19

<210> SEQ ID NO 31
<211> LENGTH: 19
<212> TYPE: RNA
<213> ORGANISM: artificial
<220> FEATURE:
<223> OTHER INFORMATION: Chemically synthesized

<400> SEQUENCE: 31
ugucuguaag auagcugcc                                                    19

<210> SEQ ID NO 32
<211> LENGTH: 19
<212> TYPE: RNA
<213> ORGANISM: artificial
<220> FEATURE:
<223> OTHER INFORMATION: Chemically synthesized

<400> SEQUENCE: 32
uacucgcagu ccgagcucu                                                    19

<210> SEQ ID NO 33
<211> LENGTH: 19
<212> TYPE: RNA
<213> ORGANISM: artificial
<220> FEATURE:
<223> OTHER INFORMATION: Chemically synthesized

<400> SEQUENCE: 33
uguucuagau ggaagaccc                                                    19

<210> SEQ ID NO 34
<211> LENGTH: 19
<212> TYPE: RNA
<213> ORGANISM: artificial
<220> FEATURE:
<223> OTHER INFORMATION: Chemically synthesized

<400> SEQUENCE: 34
ucugccucua gucuccacc                                                    19

<210> SEQ ID NO 35
<211> LENGTH: 19
<212> TYPE: RNA
<213> ORGANISM: artificial
<220> FEATURE:
<223> OTHER INFORMATION: Chemically synthesized

<400> SEQUENCE: 35
```
uucgucucug ucuuggagg    19

<210> SEQ ID NO 36
<211> LENGTH: 19
<212> TYPE: RNA
<213> ORGANISM: artificial
<220> FEATURE:
<223> OTHER INFORMATION: Chemically synthesized

<400> SEQUENCE: 36
uacaacucaa ugagcuucc    19

<210> SEQ ID NO 37
<211> LENGTH: 19
<212> TYPE: RNA
<213> ORGANISM: artificial
<220> FEATURE:
<223> OTHER INFORMATION: Chemically synthesized

<400> SEQUENCE: 37
uaggcuuaaa cgcagcugc    19

<210> SEQ ID NO 38
<211> LENGTH: 19
<212> TYPE: RNA
<213> ORGANISM: artificial
<220> FEATURE:
<223> OTHER INFORMATION: Chemically synthesized

<400> SEQUENCE: 38
auuucaugcu acaguacug    19

<210> SEQ ID NO 39
<211> LENGTH: 19
<212> TYPE: RNA
<213> ORGANISM: artificial
<220> FEATURE:
<223> OTHER INFORMATION: Chemically synthesized

<400> SEQUENCE: 39
ccucaguacu guagcauga    19

<210> SEQ ID NO 40
<211> LENGTH: 19
<212> TYPE: RNA
<213> ORGANISM: artificial
<220> FEATURE:
<223> OTHER INFORMATION: Chemically synthesized

<400> SEQUENCE: 40
cucaguacug uagcaugaa    19

<210> SEQ ID NO 41
<211> LENGTH: 19
<212> TYPE: RNA
<213> ORGANISM: artificial
<220> FEATURE:
<223> OTHER INFORMATION: Chemically synthesized

<400> SEQUENCE: 41
uacuguagca ugaaacaaa    19

<210> SEQ ID NO 42
<211> LENGTH: 19
<212> TYPE: RNA

```
<213> ORGANISM: artificial
<220> FEATURE:
<223> OTHER INFORMATION: Chemically synthesized

<400> SEQUENCE: 42
ucaugcuaca guacugagg                                                    19

<210> SEQ ID NO 43
<211> LENGTH: 19
<212> TYPE: RNA
<213> ORGANISM: artificial
<220> FEATURE:
<223> OTHER INFORMATION: Chemically synthesized

<400> SEQUENCE: 43
uucaugcuac aguacugag                                                    19

<210> SEQ ID NO 44
<211> LENGTH: 19
<212> TYPE: RNA
<213> ORGANISM: Artificial Sequence
<220> FEATURE:
<223> OTHER INFORMATION: Chemically synthesized

<400> SEQUENCE: 44
uuuguuucau gcuacagua                                                    19
```